US011661601B2

(12) United States Patent
Rigo et al.

(10) Patent No.: US 11,661,601 B2
(45) Date of Patent: May 30, 2023

(54) METHODS FOR MODULATING FMR1 EXPRESSION

(71) Applicants: IONIS PHARMACEUTICALS, INC., Carlsbad, CA (US); THE REGENTS OF THE UNIVERSITY OF MICHIGAN, Ann Arbor, MI (US)

(72) Inventors: Frank Rigo, Carlsbad, CA (US); Peter Todd, Ann Arbor, MI (US); Caitlin Rodriguez, Ann Arbor, MI (US)

(73) Assignees: IONIS PHARMACEUTICALS, INC., Carlsbad, CA (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/982,787

(22) PCT Filed: Mar. 22, 2019

(86) PCT No.: PCT/US2019/023518
§ 371 (c)(1),
(2) Date: Sep. 21, 2020

(87) PCT Pub. No.: WO2019/183440
PCT Pub. Date: Sep. 26, 2019

(65) Prior Publication Data
US 2021/0002642 A1 Jan. 7, 2021

Related U.S. Application Data

(60) Provisional application No. 62/740,285, filed on Oct. 2, 2018, provisional application No. 62/646,803, filed on Mar. 22, 2018.

(51) Int. Cl.
*C12N 15/113* (2010.01)
(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/351* (2013.01)
(58) Field of Classification Search
CPC .............. C12N 15/113; C12N 2310/11; C12N 2310/315; C12N 2310/321; C12N 2310/3341; C12N 2310/341; C12N 2310/351
See application file for complete search history.

(56) References Cited

U.S. PATENT DOCUMENTS

| | | |
|---|---|---|
| 3,687,808 A | 8/1972 | Merigan, Jr. et al. |
| 4,415,732 A | 11/1983 | Caruthers et al. |
| 4,469,863 A | 9/1984 | Ts O et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | Mcgeehan et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |

(Continued)

FOREIGN PATENT DOCUMENTS

| WO | 2002028878 A1 | 4/2002 |
|---|---|---|
| WO | 2007056113 A2 | 5/2007 |

(Continued)

OTHER PUBLICATIONS

PCT Search Report and Written Opinion prepared for PCT/US2019/023518, completed Jul. 15, 2019.
PCT International Search Report for PCT/US 19/23518; Completed Jul. 30, 2019.
Branch, Andrea D., "A Good Antisense Molecule is Hard to Find," 1998, Elsevier Science Ltd., pp. 45-50.
Chin, Andrew, "On the Preparation and Utilization of Isolated and Purified Oligonucleotides," Mar. 9, 2002, University of North Carolina School of Law, (1 page).
Crooke, S.T., "Basic Principles of Antisense Therapeutics," 1998, Chapter 1 pp. 1-50.

(Continued)

*Primary Examiner* — J. E. Angell
(74) *Attorney, Agent, or Firm* — Barnes & Thornburg LLP

(57) ABSTRACT

Provided are methods for increasing the amount or activity of FMR1 RNA, and in certain instances of increasing the amount of FMRP protein, in an animal Such methods are useful to prevent or ameliorate at least one symptom of a Fragile X-Spectrum disorder. Such Fragile X-Spectrum disorders include FXS, FXTAS, and FXPOI.

20 Claims, No Drawings
Specification includes a Sequence Listing.

(56) References Cited

U.S. PATENT DOCUMENTS

| | | |
|---|---|---|
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | Mcgee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts O et al. |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel |
| 7,101,993 B1 | 9/2006 | Cook et al. |
| 7,250,496 B2 * | 7/2007 | Bentwich .............. G16B 15/10 536/23.1 |
| 7,262,177 B2 | 8/2007 | Ts'O et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 9/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze |

(56) References Cited

U.S. PATENT DOCUMENTS

| | | | |
|---|---|---|---|
| 2013/0130378 A1 | 5/2013 | Manoharan et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2016/0281175 A1 | 9/2016 | Weinhusel et al. |

FOREIGN PATENT DOCUMENTS

| | | |
|---|---|---|
| WO | WO2007056113 | 5/2007 |
| WO | 2017015575 A1 | 1/2017 |
| WO | WO2017015575 | 1/2017 |
| WO | 2017075038 A1 | 5/2017 |
| WO | 2019183440 A1 | 9/2019 |

OTHER PUBLICATIONS

Crooke, S.T., "Antisense Drug Technology" 2008, pp. 1-414.

Egli, Martin, et al., "Synthesis Improved Antisense Activity and Structural Rationale for the Divergent RNA Affinities of 3'-Fluoro Hexitol Nucleic Acid (FHNA and Ara-FHNA) Modified Oligonucleotides," Oct. 19, 2011 pp. 6-21.

Gautschi, Oliver, et al., "Activity of a Novel bcl-2/bcl-xL-Bispecific Antisense Oligonucleotide Against Tumors of Diverse Histologic Origins," Mar. 21, 2001, Journal of the National Cancer Institute, vol. 93, No. 6, pp. 463-471.

Hagerman, Paul, MD, PhD, "Fragile X-Associated Tremor/Ataxia Syndrome (FXTAS): Pathology and Mechanisms," Jul. 2013, ACTA Neuropathol, pp. 1-30.

Maher, Louis J., III et al., Comparative hybrid arrest by tandem antisense oligodeoxyribonucleotides or oligodeosy-ribonucleoside methylphosphnates in a cell-free system. 1988, Nucelic Acids Research, vol. 16 No. 8, pp. 1-18.

NC 00002311, *Homo sapiens* chromosome X, GRCH38.P13 Primary Assembly, May 16, 2021 (2 pages).

"Nucleic Acids, Linkers and Primers," New Englad Biolabs, (3 pages).

Nelson, David L., et al., "The Unstable Repeats—Three Evolving Faces of Neurological Disease," Mar. 6, 2013, Neuron, pp. 1-35.

Reynolds, Angela, et al., "Rational siRNA design for RNA interference," Nature Biotechnology, Mar. 2004, vol. 22, No. 3, pp. 326-330.

Rodriguez, Caitlin M., et al. "A native function for RAN translation and CGG repeats in regulating fragile X protein synthesis," Nature Neuroscience, vol. 23, Mar. 2020, pp. 386-397.

Sanghvi, Yogesh S., "Heterocyclic Base Modifications in Nucleic Acids and Their Applications in Antisense Oligonucleotides, Chapter 15," 1993, CRC Press, Inc. pp. 274-285.

Seth, Punit P., et al., "Short Antisense Oligonucleotides with Novel 2'-4' Conformationaly Restricted Nucleoside Analogues Show Improved Potency without Increased Toxicity in Animals," J. Med. Chem., 2009,pp. 10-13.

Todd, PeterK., et al., "CGG Repeat Associated Translation Mediates Neurodegeneration in Fragile X Tremor Ataxia Syndrome," Neuron, May 8, 2013, pp. 1-28.

Woolf, Tod M., et al., "Specificity of antisense oligonucleotides in vivo," Aug. 1992, Proc. Natl. Acad. Sci vol. 89, pp. 7305-7309.

Wright SE, et al., Antisense Oligonucleotides block RAN translation, enhance FMRP, and reduce toxicity in Fragil X human neurons, Poster (1 page).

Boivin et al., "Potential pathogenic mechanisms underlying Fragile X Tremor Ataxia Syndrome: RAN translation and/or RNA gain-of-function?" European Journal of Medical Genetics (2018) 61: 674-679.

Derbis et al., "Quantitative Evaluation of Toxic Polyglycine Biosynthesis and Aggregation in Cell Models Expressing Expanded CGG Repeats" Frontiers in Genetics (2018) 9: 1-13.

Extended EP Search Report for 19772559.1 dated Nov. 25, 2021.

Glineburg et al., "Repeat-associated non-AUG (RAN) translation and other molecular mechanisms in Fragile X Tremor Ataxia Syndrome" Brain Research (2018) 1693:43-54.

Liu et al. "Rescue of Fragile X Syndrome Neurons by DNA Methylation Editing of the FMR1 Gene" Cell (2018) 172: 979-992.

Rodriguez et al., "The Role of Upstream Open Reading Frames in Regulating Neuronal Protein Synthesis" Dissertation (2018) University of Michigan.

Sellier et al., "Translation of Expanded CGG Repeats into FMRpolyG is Pathogenic and May Contribute to Fragile X Tremor Ataxia Syndrome" Neuron (2017) 93: 331-347.

Tabet et al., "CUG initiation and frameshifting enable production of dipeptide repeat proteins from ALS/FTD C9ORF72 transcripts" Nature Comm (2018) 152: 1-14.

\* cited by examiner

METHODS FOR MODULATING FMR1 EXPRESSION

CROSS-REFERENCE TO RELATED APPLICATIONS

This application is a national stage entry under 35 USC § 371 of PCT International Application Number PCT/US2019/023518, filed Mar. 22, 2019, which claims priority under 35 U.S.C. § 119(e) to U.S. Provisional Application Ser. No. 62/646,803 filed on Mar. 22, 2018, and U.S. Provisional Application Ser. No. 62/740,285 filed on Oct. 2, 2018, the entire disclosures of which are incorporated herein by reference.

SEQUENCE LISTING

The present application is being filed along with a Sequence Listing in electronic format. The Sequence Listing is provided as a file entitled BIOL0326USL2SEQ_ST25.txt, created on Mar. 19, 2019, which is 128 KB in size. The information in the electronic format of the sequence listing is incorporated herein by reference in its entirety.

STATEMENT OF GOVERNMENT SUPPORT

This invention was made with government support under R01NS086810 and F31NS090883 awarded by National Institute of Health. The government has certain rights in the invention.

FIELD

Provided are compositions and methods for reducing Repeat Associated Non-AUG (RAN) translation products and increasing FMR1 RNA and FMRP synthesis, in a cell or an animal. Such compositions and methods are useful to prevent or ameliorate at least one symptom or hallmark of a fragile X-spectrum disorder. Such fragile X-spectrum disorders include Fragile X Syndrome (FXS), Fragile X-Associated Tremor/Ataxia Syndrome (FXTAS), and Fragile-X-Associated Premature Ovarian Failure (FXPOI).

BACKGROUND

Fragile X-Spectrum disorders are caused by varying length CGG repeats at the FMR1 locus, with FXS being caused by repeat expansions containing more than 200 CGG repeats, and FXTAS and FXPOI being caused by shorter, so-called premutation repeats, containing 55-200 CGG repeats. The normal, non-disease associated repeat length is approximately 30 repeats. FMR1 encodes FMRP, an RNA-binding protein that plays a central role in regulating activity-dependent protein translation at synapses by suppressing translation of bound transcripts. Levels of FMRP in FXS can be impaired through two distinct mechanisms: hyper-methylation of cytosine residues leading to heterochromatin formation and transcriptional silencing at the FMR1 locus, or decreased translational efficiency as CGG repeats impair ribosomal scanning through the 5'-UTR. FXTAS patients tend to have unmethylated repeats that enhance FMR1 transcription, leading to neuronal inclusions (Nelson, Orr, and Warren, The unstable repeats-three evolving faces of neurological disease, Neuron, 2013)(Hagerman, Fragile X-associated tremo/ataxia syndrome (FXTAS): pathology and mechanisms, Acta Neuropathol., 2013).

RAN translation from CGG repeats can lead to the formation of homopolymeric polyglycine, polyalanine, and polyarginine proteins. Polyglycine is the most predominant product of RAN translation initiating at CGG repeats and forms intranuclear neuronal inclusions in the brains of FXTAS patients and in the ovaries of FXPOI patients (Todd, et. al., CGG Repeat-associated translation mediates neurodegeneration in the fragile X tremor ataxia syndrome, Neuron, 2013).

Currently there is a lack of acceptable options for treating fragile X-spectrum disorders such as Fragile X Syndrome (FXS), fragile X-associated tremor/ataxia syndrome (FXTAS), and fragile-X-associated premature ovarian failure (FXPOI). It is therefore an object herein to provide compositions and methods for the treatment of such disorders.

SUMMARY OF THE INVENTION

Provided are compositions and methods for reducing Repeat Associated Non-AUG (RAN) translation products and increasing FMRP synthesis, in a cell or an animal. In certain embodiments, the animal has a fragile X-spectrum disorder. In certain embodiments, such fragile X-spectrum disorders include FXS, FXTAS, and FXPOI. In certain embodiments, compounds useful for reducing RAN translation products and increasing FMRP synthesis are oligomeric compounds or modified oligonucleotides. In certain embodiments, the oligomeric compound comprises a modified oligonucleotide.

Also provided are methods useful for ameliorating at least one symptom or hallmark of a fragile X-spectrum disorder. In certain embodiments, the fragile X-spectrum disorder is FXS, FXTAS, or FXPOI. In certain embodiments symptoms include intellectual disability; physical abnormalities, such as prominent ears; anxiety; depression; ataxia; tremor; memory loss; peripheral neuropathy; occult primary ovarian insufficiency; and polycystic ovarian syndrome. In certain embodiments, amelioration of these symptoms results in increased intellect, lack of physical abnormality, reduced anxiety, reduced depression, improved movement, improved memory, reduced pain or numbness in limbs, improved ovarian function, and normalization of menses. In certain embodiments, hallmarks include neuron death and presence of RAN translation products, such as polyglycine, polyalanine, and polyarginine proteins.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).). Unless otherwise indicated, a 2'-deoxynucleoside comprises a deoxyribosyl sugar moiety having the β-D stereochemical 'configuration.

As used herein, "administering" means providing a pharmaceutical agent to an animal. "Administered prior to the detection of the at least one symptom" is prophylactic administration and means providing the pharmaceutical agent to an animal before a symptom of a fragile X-spectrum disorder is apparent through clinical diagnosis.

As used herein, "animal" means a human or non-human animal.

As used herein, "antisense activity" means any detectable and/or measurable change attributable to the hybridization of an antisense compound to its target nucleic acid. In certain embodiments, antisense activity is an increase in the expression or amount of a target nucleic acid or protein encoded by such target nucleic acid compared to target nucleic acid levels or target protein levels in the absence of the antisense compound.

As used herein, "ameliorate" or "amelioration" in reference to a treatment means improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, symptoms are neuronal death and presence of RAN translation products, such as polyglycine, polyalanine, and polyarginine proteins.

As used herein, "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions.

Complementary nucleobases means nucleobases that are capable of forming hydrogen bonds with one another. Complementary nucleobase pairs include, but unless otherwise specified are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to an oligonucleotide means that the oligonucleotide is complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

As used herein, "increasing the expression or amount" refers to enhanced expression or greater amount relative to the expression or amount in an untreated or control sample.

As used herein, "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate linkage" means a modified internucleoside linkage in which one of the non-bridging oxygen atoms of a phosphodiester internucleoside linkage is replaced with a sulfur atom.

As used herein, "MOE" means O-methoxyethyl. "2'-MOE" means a —OCH$_2$CH$_2$OCH$_3$ group at the 2' position of a furanosyl ring.

As used herein, "fragile X-spectrum disorder" means a condition marked by large (greater than 55) CGG nucleotide repat expansions in the 5' UTR of the FMR1 gene on the X chromosome. Fragile X-spectrum disorders include Fragile X Syndrome (FXS), Fragile X-associated Tremor/Ataxia Syndrome (FXTAS), and Fragile X-associated Premature Ovarian Failure (FXPOI). FXS is the leading monogenic cause of autism and intellectual disability. FXTAS is an age-related neurodegenerative disease characterized by gait difficulties, action tremor, and dementia with executive dysfunction and, in some cases, Parkinsonism and peripheral neuropathy. FXPOI is the most common inherited cause of early menopause.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase.

A universal base is a modified nucleobase that can pair with any one of the five unmodified nucleobases. As used herein, "nucleobase sequence" means the order of contiguous nucleobases (i.e. no additional nucleobases are present between those that are contiguous) in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e. no additional nucleosides are present between those that are linked).

As used herein, "O-methyl" means methoxy. "2'-O-methyl" means a —OCH$_3$ group at the 2' position of a furanosyl ring.

As used herein, "oligomeric compound" means a compound comprising an oligonucleotide and optionally one or more additional features, such as a conjugate group or terminal group. An oligomeric compound may be paired with a second oligomeric compound or may be unpaired. A "singled-stranded oligomeric compound" is an unpaired oligomeric compound. A "duplexed oligomeric compound" is an oligomeric compound paired with a second oligomeric compound; this is an "oligomeric duplex."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "Repeat Associated Non-AUG (RAN) translation products" means the synthesis products from translational initiation of a nucleotide repeat expansion in the absence of a normal ORF or AUG start codon. For example, RAN translation of the CGG repeat expansion in the 5' UTR of FMR1 results in synthesis of polyglycine, polyalanine, and polyarginine proteins.

As used herein, "salts" mean physiologically and pharmaceutically acceptable salts of oligomeric compounds or oligonucleotides (including modified oligonucleotides), i.e., salts that retain the desired biological activity of the parent oligomeric compound or oligonucleotide (including modified oligonucleotides) and do not impart undesired toxicological effects thereto.

As used herein, "standard cell assay" means the assay described in Example 3 and reasonable variations thereof.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. Modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid" means a nucleic acid to which an oligomeric compound or oligonucleotide (including a modified oligonucleotide) is designed to hybridize.

As used herein, "therapeutically effective amount" means an amount of a pharmaceutical agent that provides a therapeutic benefit to an animal. For example, a therapeutically effective amount improves a symptom of a disease.

Numbered Embodiments

The present disclosure provides the following non-limiting numbered embodiments:

Embodiment 1

An oligomeric compound comprising a modified oligonucleotide consisting of 10-30 linked nucleosides and having a nucleobase sequence comprising at least 12, 13, 14, 15, 16, 17, or 18 nucleobases of any of SEQ ID NOS: 11-16.

Embodiment 2

An oligomeric compound comprising a modified oligonucleotide consisting of 10-30 linked nucleosides and having a nucleobase sequence complementary to at least 8, at least 9, at least 10, at least 11, at least 12, at least 13, at least 14, at least 15, at least 16, at least 17, or at least 18 contiguous nucleobases of an equal length portion of nucleobases 3001-3042 of SEQ ID NO: 1.

Embodiment 3

The oligomeric compound of embodiment 1 or embodiment 2, wherein the modified oligonucleotide has a nucleobase sequence that is at least 80%, 85%, 90%, 95%, or 100% complementary to the nucleobase sequence of SEQ ID NO: 1, when measured across the entire nucleobase sequence of the modified oligonucleotide.

Embodiment 4

The oligomeric compound of any of embodiments 1-3, wherein the modified oligonucleotide comprises at least one modified nucleoside.

Embodiment 5

The oligomeric compound of embodiment 4, wherein the modified oligonucleotide comprises at least one modified nucleoside comprising a modified sugar moiety.

Embodiment 6

The oligomeric compound of embodiment 5, wherein the modified oligonucleotide comprises at least one modified nucleoside comprising a bicyclic sugar moiety.

Embodiment 7

The oligomeric compound of embodiment 6, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 8

The oligomeric compound of any of embodiments 4-7, wherein the modified oligonucleotide comprises at least one modified nucleoside comprising a non-bicyclic modified sugar moiety.

Embodiment 9

The oligomeric compound of embodiment 8, wherein the modified oligonucleotide comprises at least one modified nucleoside comprising a non-bicyclic modified sugar moiety comprising a 2'-MOE modified sugar or 2'-O-methyl modified sugar.

Embodiment 10

The oligomeric compound of any of embodiments 4-9, wherein the modified oligonucleotide comprises at least one modified nucleoside comprising a sugar surrogate.

Embodiment 11

The oligomeric compound of embodiment 10, wherein the modified oligonucleotide comprises at least one modified nucleoside comprising a sugar surrogate selected from morpholino and PNA.

Embodiment 12

The oligomeric compound of any of embodiments 1-11, wherein the modified oligonucleotide is a gapmer.

Embodiment 13

The oligomeric compound of any of embodiments 1-12, wherein the modified oligonucleotide comprises at least one modified internucleoside linkage.

Embodiment 14

The oligomeric compound of embodiment 13, wherein each internucleoside linkage of the modified oligonucleotide is a modified internucleoside linkage.

Embodiment 15

The oligomeric compound of embodiment 13 or 14 wherein the modified internucleoside linkage is a phosphorothioate internucleoside linkage.

Embodiment 16

The oligomeric compound of embodiment 13 or 15 wherein the modified oligonucleotide comprises at least one phosphodiester internucleoside linkage.

Embodiment 17

The oligomeric compound of any of embodiments 13, 15, or 16, wherein each internucleoside linkage is either a phosphodiester internucleoside linkage or a phosphorothioate internucleoside linkage.

Embodiment 18

The oligomeric compound of any of embodiments 1-17, wherein the modified oligonucleotide comprises at least one modified nucleobase.

Embodiment 19

The oligomeric compound of embodiment 18, wherein the modified nucleobase is a 5-methyl cytosine.

Embodiment 20

The oligomeric compound of any of embodiments 1-19, wherein the modified oligonucleotide consists of 12-30, 12-22, 12-20, 14-20, 15-25, 16-18, 16-20, 18-22 or 18-20 linked nucleosides.

Embodiment 21

The oligomeric compound of any of embodiments 1-20, wherein the modified oligonucleotide consists of 16 or 18 linked nucleosides.

Embodiment 22

The oligomeric compound of any of embodiments 1-21 consisting of the modified oligonucleotide.

Embodiment 23

The oligomeric compound of any of embodiments 1-21 comprising a conjugate group comprising a conjugate moiety and a conjugate linker.

Embodiment 24

The oligomeric compound of embodiment 23, wherein the conjugate group comprises a GalNAc cluster comprising 1-3 GalNAc ligands.

Embodiment 25

The oligomeric compound of embodiment 23 or 24, wherein the conjugate linker consists of a single bond.

Embodiment 26

The oligomeric compound of embodiment 24, wherein the conjugate linker is cleavable.

Embodiment 27

The oligomeric compound of embodiment 23, 24, or 26, wherein the conjugate linker comprises 1-3 linker-nucleosides.

Embodiment 28

The oligomeric compound of any of embodiments 23-27, wherein the conjugate group is attached to the modified oligonucleotide at the 5'-end of the modified oligonucleotide.

Embodiment 29

The oligomeric compound of any of embodiments 23-27, wherein the conjugate group is attached to the modified oligonucleotide at the 3'-end of the modified oligonucleotide.

Embodiment 30

The oligomeric compound of any of embodiments 1-29 comprising a terminal group.

Embodiment 31

The oligomeric compound of any of embodiments 1-30 wherein the oligomeric compound is a singled-stranded oligomeric compound.

Embodiment 32

The oligomeric compound of any of embodiments 1-26 or 28-30, wherein the oligomeric compound does not comprise linker-nucleosides.

Embodiment 33

An oligomeric duplex comprising an oligomeric compound of any of embodiments 1-30 or 32.

Embodiment 34

An antisense compound comprising or consisting of an oligomeric compound of any of embodiments 1-32 or an oligomeric duplex of embodiment 33.

Embodiment 35

A chirally enriched population of oligomeric compound of embodiment 1 or embodiment 2, wherein the population is enriched for oligomeric compounds comprising at least one particular phorphorothioate internucleoside linkage having a particular stereochemical configuration.

Embodiment 36

The chirally enriched population of embodiment 35, wherein the population is enriched for oligomeric compounds comprising at least one particular phorphorothioate internucleoside linkage having the (Sp) configuration.

Embodiment 37

The chirally enriched population of embodiment 35, wherein the population is enriched for oligomeric compounds comprising at least one particular phorphorothioate internucleoside linkage having the (Rp) configuration.

Embodiment 38

The chirally enriched population of embodiment 35, wherein the population is enriched for oligomeric compounds having a particular, independently selected stereochemical configuration at each phosphorothioate internucleoside linkage.

Embodiment 39

The chirally enriched population of embodiment 38, wherein the population is enriched for modified oligomeric compounds having the (Sp) configuration at each phosphorothioate internucleoside linkage.

Embodiment 40

The chirally enriched population of embodiment 38, wherein the population is enriched for oligomeric compounds having the (Rp) configuration at each phosphorothioate internucleoside linkage.

Embodiment 41

The chirally enriched population of embodiment 38, wherein the population is enriched for oligomeric compounds having the (Rp) configuration at one particular phosphorothioate internucleoside linkage and the (Sp) configuration at each of the remaining phosphorothioate internucleoside linkages.

Embodiment 42

The chirally enriched population of embodiment 35 or embodiment 38 wherein the population is enriched for oligomeric compounds having at least 3 contiguous phosphorothioate internucleoside linkages in the Sp, Sp, and Rp configurations, in the 5' to 3' direction.

Embodiment 43

A chirally enriched population of oligomeric compounds of any of embodiments 1-32, wherein all of the phosphorothioate internucleoside linkages of the modified oligonucleotide are stereorandom.

Embodiment 44

A pharmaceutical composition comprising an oligomeric compound of any of embodiments 1-32 or an oligomeric duplex of embodiment 33 and a pharmaceutically acceptable carrier or diluent.

Embodiment 45

A method of increasing the amount of FMR1 RNA in cells or tissues comprising contacting the cells or tissues with the oligomeric compound of any of embodiments 1-32, the oligomeric duplex of embodiment 33, the antisense compound of embodiment 34, or the pharmaceutical composition of embodiment 35.

Embodiment 46

A method of increasing the amount of FMRP in cells or tissues comprising contacting the cells or tissues with the oligomeric compound of any of embodiments 1-32, the oligomeric duplex of embodiment 33, the antisense compound of embodiment 34, or the pharmaceutical composition of embodiment 35.

Embodiment 47

A method of decreasing the amount of RAN translation products in cells or tissues comprising contacting the cells or tissues with the oligomeric compound of any of embodiments 1-32, the oligomeric duplex of embodiment 33, the antisense compound of embodiment 34, or the pharmaceutical composition of embodiment 44.

Embodiment 48

The method of embodiment 47, wherein the RAN translation product is any of as polyglycine, polyalanine, and polyarginine.

Embodiment 49

A method of preserving neurons in an animal in need thereof comprising administering to the animal the pharmaceutical composition of embodiment 44.

Embodiment 50

A method comprising administering to an animal having a Fragile X-Spectrum disorder the oligomeric compound of any of embodiments 1-32, the oligomeric duplex of embodiment 33, the antisense compound of embodiment 34, or the pharmaceutical composition of embodiment 44; wherein the administering preserves neurons.

Embodiment 51

The method of embodiment 50, wherein the fragile X-spectrum disorder is FXS, FXTAS, or FXPOI.

Embodiment 52

The method of embodiment 50 or embodiment 51, wherein the oligomeric compound, oligomeric duplex, antisense compound, or pharmaceutical composition is administered prior to the detection of the at least one symptom of a fragile X-spectrum disorder.

Embodiment 53

The method of any of embodiments 50-52, wherein the amount of total FMR1 RNA is increased in the animal.

Embodiment 54

The method of any of embodiments 50-53, wherein the amount of total FMRP protein is increased in the animal.

Embodiment 55

The method of any of embodiments 50-54, wherein the amount of RAN translation products is reduced in the animal.

Embodiment 56

The method of embodiment 55, wherein the RAN translation product is any of as polyglycine, polyalanine, and polyarginine.

Embodiment 57

The method of any of embodiments 50-56, wherein the animal is a human.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'—OCH$_3$ ("OMe" or "O-methyl"), and 2'-O(CH$_2$)$_2$OCH$_3$("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, $OCH_3$, and $OCH_2CH_2OCH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399, 845, Bhat et al., U.S. Pat. No. 7,569,686, Swayze et al., U.S. Pat. No. 7,741,457, and Swayze et al., U.S. Pat. No. 8,022, 193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., J. Org. Chem., 2009, 74, 118-134), 4'-$CH_2$—$C(=CH_2)$-2' and analogs thereof (see e.g., Seth et al., U.S. Pat. No. 8,278, 426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$, alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)=C(R_b)$—, —$C(R_a)=N$—, —$C(=NR_a)$—, —$C(=O)$—, —$C(=S)$—, —O—, —$Si(R_a)_2$—, —$S(=O)_n$—, and —$N(R_a)$—;

wherein:
x is 0, 1, or 2;
n is 1, 2, 3, or 4;
each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)$—H), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)$—H), substituted acyl, a heterocycle radical, a substituted heterocycle radical, $C_1$-$C_{13}$ aminoalkyl, substituted $C_1$-$C_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794, 499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/ 014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

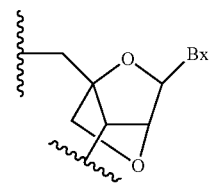

LNA (β-D-configuration)
bridge = 4'-$CH_2$—O-2'

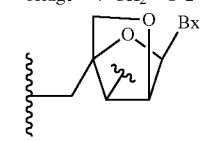

α-L-LNA (α-L-configuration)
bridge = 4'-$CH_2$—O-2'

α-L-methyleneoxy (4'-$CH_2$—O-2') or α-L-LNA bicyclic nucleosides have been incorporated into oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

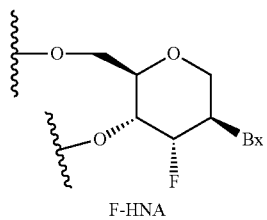

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005, 906; F-HNA can also be referred to as a F-THP or 3'-fluoro tetrahydropyran), and nucleosides comprising additional modified THP compounds having the formula:

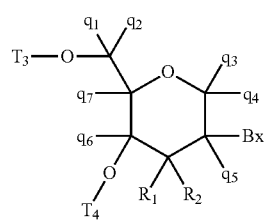

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

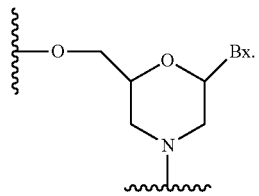

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—CH$_2$—N(CH$_3$)—O—CH$_2$—), thiodiester, thionocarbamate (—O—C(═O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

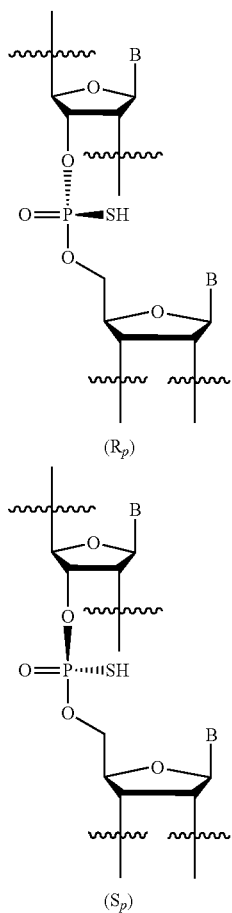

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O—5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, oligomeric compounds described herein are complementary to a target nucleic acid comprising a single-nucleotide polymorphism (SNP). In certain such embodiments, the oligomeric compound is capable of modulating expression of one allele of the SNP-containing target nucleic acid to a greater or lesser extent than it modulates another allele. In certain embodiments, an oligomeric compound hybridizes to a (SNP)-containing target nucleic acid at the single-nucleotide polymorphism site.

In certain embodiments, oligomeric compounds are at least partially complementary to more than one target nucleic acid. For example, oliogomeric compounds described herein may mimic microRNAs, which typically bind to multiple targets.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. FMR1

In certain embodiments, oligomeric compounds comprise or consist of any oligonucleotide comprising a region that is complementary to a target nucleic acid, wherein the target nucleic acid is FMR1. In certain embodiments, FMR1 nucleic acid has the sequence set forth in the complement of GENBANK Accession No. NC_000023.11 truncated from 147909001 to 147954000 (SEQ ID NO: 1).

In certain embodiments, contacting a cell with an oligonucleotide complementary to SEQ ID NO: 1 increases the amount of FMR1 RNA. In certain embodiments, contacting a cell with an oligonucleotide complementary to SEQ ID NO: 1 increases the amount of total FMRP. In certain embodiments, contacting a cell with an oligomeric compound complementary to SEQ ID NO: 1 ameliroates one or more symptoms or hallmarks of fragile X-spectrum disorder. In certain embodiments symptoms or hallmarks include intellectual disability; physical abnormalities, such as prominent ears; anxiety; depression; ataxia; tremor; memory loss; peripheral neuropathy; occult primary ovarian insufficiency; polycystic ovarian syndrome; neuron death; reduced levels of FMR1 RNA; reduced levels of FMRP; and presence of RAN translation products, such as polyglycine, polyalanine, and polyarginine proteins. In certain embodiments, amelioration of these symptoms results in increased intellect, lack of physical abnormality, reduced anxiety, reduced depression, improved movement, improved memory, reduced pain or numbness in limbs, improved ovarian function, normalization of menses, neuron preservation, increased levels of FMR1 RNA, increased levels of FMRP, and lack of (or reduced levels of) RAN translation products, such as polyglycine, polyalanine, and polyarginine proteins.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in CNS tissue, including neurons.

VI. Certain Pharmaceutical Compositions

In certain embodiments, described herein are pharmaceutical compositions comprising one or more oligomeric compounds or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS. In certain embodiments, a pharmaceutical composition comprises one or more oligomeric compound and artificial cerebrospinal fluid (aCSF). In certain embodiments, a pharmaceutical composition consists of one or more oligomeric compound and sterile aCSF. In certain embodiments, the sterile aCSF is pharmaceutical grade aCSF.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, oligomeric compounds and modified oligonucleotides described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

A Reporter System for RAN Translation

Repeat-Associated Non-AUG (RAN) translation produces homopolymeric or dipeptide repeat-containing proteins from nucleotide repeat expansions in the absence of a canonical AUG start site. RAN translation can occur in multiple reading frames on the same repeat and occurs in RNA regions typically thought of as non-coding, including 5'-UTRs (Kearse, et. al., "CGG Repeat-Associated Non-AUG Translation Utilizes a Cap-Dependent Scanning Mechanism of Initiation to Produce Toxic Proteins", Molecular Cell, 2016). In order to elucidate the mechanisms of translation initiation and translation efficiency at RAN translation sites within the 5'-UTR of FMR1, a luciferase reporter system was developed. The reporter system has been described in detail in Kearse, et. al., 2016.

In this system, the gene for nanoluciferase, a fluorescent protein that can be easily measured in cells by conventional methods, is fused to the repeat-containing 5'-UTR of FMR1. Nanoluciferase is fused to the 5'-UTR of FMR1 in different reading frames, as indicated in the table below. Reporter genes were constructed with two versions of the 5'UTR of FMR1, one containing a normal, non-symptomatic repeat length of 25 CGG repeats, and one containing a "premutation" repeat length of 90 CGG repeats, associated with FXTAS and FXPOI.

When nanolucifease is fused to the 5'-UTR of FMR1 in-frame, (CGG)$_n$ FMRP-nLuc, the reporter system "reports" on the expression of full-length Fragile-X-Mental Retardation Protein, FMRP; that is, if a given treatment would increase FMRP expression in a cell, the same treatment will increase nanoluciferase expression in cells containing a (CGG)$_n$FMRP-nLuc reporter. When nanoluciferase is fused to the 5'-UTR of FMR1 with a +1 frame shift, the reporter system "reports" on RAN translation that would lead to expression of polyglycine; that is, if a given treatment would decrease polyglycine in a cell, the same treatment will decrease nanoluciferase expression in cells containing a +1 (CGG)$_n$RAN-nLuc reporter.

In a variation of the nanoluciferase reporter system, a green fluorescent protein (GFP) protein was also attached to the 5'-UTR of FMR1 with a +1 frame shift. For this construct, expression of GFP correlates to RAN translation that represents the expression of polyglycine. A different variation of this reporter system has a fluorescent Venus protein attached to the 5'-UTR of FMR1 with a +1 frame shift. For this construct, expression of Venus correlates to RAN translation that represents the expression of polyglycine.

The gene constructs also contain the conventional FLAG tag (Einhauer and Jungbauer, "The FLAG™ peptide, a versatile fusion tag for the purification of recombinant proteins", Journal of Biochemical and Biophysical Methods, 2001) on the 3' end. The FLAG tag is commonly used for protein detection by western blot or protein purification with antibodies directed to the FLAG tag.

TABLE 1

Reporter constructs

| Reporter Name | Reporter description | 5' UTR CGG repeats | Report product | SEQ ID NO |
|---|---|---|---|---|
| (CGG)$_{25}$ FMRP-nLuc | 5'-UTR FMR1(25) -exon1 of FMRP-nanoluciferase-3xFLAG | 25 | FMRP | 4 |

TABLE 1-continued

Reporter constructs

| Reporter Name | Reporter description | 5' UTR CGG repeats | Report product | SEQ ID NO |
|---|---|---|---|---|
| (CGG)$_{90}$ FMRP-nLuc | 5'-UTR FMR1(90) -exon1 of FMRP-nanoluciferase-3xFLAG | 90 | FMRP | 5 |
| +1 (CGG)$_{25}$ RAN-nLuc | 5'-UTR FMR1(25) in +1 frame-nanoluciferase- 3xFLAG | 25 | polyglycine | 6 |
| +1 (CGG)$_{90}$ RAN-nLuc | 5'-UTR FMR1(90) in +1 frame-nanoluciferase- 3xFLAG | 90 | polyglycine | 7 |
| +1 (CGG)$_{90}$ RAN-nLuc-3'UTR | 5'-UTR FMR1(90) in +1 frame-nanoluciferase- 3xFLAG-PEST-3'UTR FMR1 | 90 | polyglycine, rapidly degrading protein | 8 |
| AUG-nLUC-Pest | nanoluciferase-PEST | n/a | AUG translation, rapidly degrading protein | 9 |
| +1 (CGG)$_{100}$ RAN-GFP | 5'UTR FMR1(100) in +1 frame-GFP | 100 | polyglycine | 10 |
| +1 (CGG)$_{90}$-RAN-Venus | 5'UTR FMR1(90) in +1 frame-Venus | 90 | polyglycine | 18 |

Example 2

Effect of Modified Oligonucleotides on RAN Translation In Vitro

Modified oligonucleotides complementary to a human Fragile X Mental Retardation 1 (FMR1) nucleic acid were tested for their effects on RAN translation products in vitro in cells containing a normal length repeat, with 25 CGG repeats in the 5'UTR of FMR1.

Experimental Procedure

HEK293 cells were plated at 1.3×10$^4$ cells/well and transfected with 100 ng CGG$_{25}$-FMRP-nLuc RNA or +1(CGG)$_{25}$-RAN-nLuc RNA using Lipefectamine© 2000 (ThermoFisher) for 7 hours. Media was changed and modified oligonucleotide was transfected at 100 nM with Lipofectamine© RNAiMAX (ThermoFisher) for 17 hours. Cells were lysed in 200 μL of Glo Lysis buffer (Promega), and nanoluciferase levels were detected using a 1:1 addition of prepared NanoGlo reagent (Promega) and analyzed on a 96-well GloMax plate reader (Promega). The levels of nanoluciferase in CGG$_{25}$-FMRP-nLuc expressing cells correspond to expression of full-length FMRP protein. The levels of nanoluciferase in +1(CGG)$_{25}$-RAN-nLuc transfected cells correspond to expression of the toxic RAN translation product polyglycine.

Modified Oligonucleotides

Modified oligonucleotides targeted to near-AUG start sites in the 5'UTR of human FMR1 were synthesized. Each nucleoside of the modified oligonucleotides in the table below comprises a 2'-O-methyl ribosyl sugar moiety and each internucleoside linkage between each nucleoside is a phosphorothioate internucleoside linkage. Compound ID Nos: 1006609-1006614 are complementary to the 5' UTR of FMR1, GENBANK NC_000023.11 truncated from 147909001 to 147954000 (SEQ ID NO: 1), and 761933 is a control oligonucleotide that is not complementary to FMR1. Each nucleoside of 761933 comprises a 2'-O-methyl group and each internucleoside linkage between each nucleoside is a phosphorothioate internucleoside linkage. The 5'UTR of FMR1 contains three near-AUG sites where RAN translation can be initiated, two of which are in the +1 frame (leading to translation of polyglycine) and one of which is in the 0 frame (leading to translation of FMRP with a N-terminal polyarginine extension, polyarginine-FMRP) (Kearse, 2016). Modified oligonucleotides 1006609-1006614 were designed such that the three most 5' nucleosides of the modified oligonucleotides overlapped with one of these three start sites, indicated in the "frame" column in the table below.

TABLE 2

Modified oligonucleotides

| Compound ID No. | SEQ ID No: 1 Start | SEQ ID No: 1 Stop | Sequence (5' to 3') | Frame | SEQ ID NO |
|---|---|---|---|---|---|
| 1006609 | 2976 | 2993 | CGTCGGCCCGCCGCCCGC | 0 ACG | 11 |
| 1006610 | 2978 | 2993 | CGTCGGCCCGCCGCCC | 0 ACG | 12 |
| 1006611 | 3001 | 3018 | CGTCACCGCCGCCGCCCG | +1 RAN ACG | 13 |
| 1006612 | 3003 | 3018 | CGTCACCGCCGCCGCC | +1 RAN ACG | 14 |
| 1006613 | 3025 | 3042 | CACGCCCCTGGCAGCGG | +1 RAN GUG | 15 |
| 1006614 | 3027 | 3042 | CACGCCCCTGGCAGC | +1 RAN GUG | 16 |
| 761933 | N/A | N/A | CATTGTTTTTGTCTTCC | control | 17 |

Results

Addition of Compound ID No. 1006611 to cells transfected with CGG$_{25}$-FMRP-nLuc RNA increased nLuc expression relative to untreated control. Percent relative nLuc activity represents the increase of full-length FMRP in cells with a normal-length CGG repeat and indicates that Compound ID No. 1006611 is effective in increasing FMRP synthesis.

TABLE 3

Relative nLuc Activity

| Compound ID No. 1006611 | % Relative nLuc Activity |
|---|---|
| 0 nM | 100.0 |
| 100 nM | 130.7 |

Relative nLuc activity was measured in cells transfected with +1(CGG)$_{25}$ RAN-nLuc-3' UTR, representing a normal-length CGG repeat, and 100 nM modified oligonucleotide. Numbers in the table below are normalized to the activity observed with the control oligonucleotide 761933. A reduction in nanoluciferase activity represents a reduction in RAN translation that would result in polyglycine and indicates that Compound ID Nos. 1006011 and 1006013 are effective in reducing RAN translation.

TABLE 4

Relative nLuc Activity

| Compound ID No. | % Relative nLuc Activity |
|---|---|
| None (control) | 88 |
| 761933 (control) | 100 |
| 1006011 | 42 |
| 1006013 | 25 |

Example 3

Effect of Modified Oligonucleotides on Endogenous FMR1 RNA Expression and FMRP Synthesis Expression In Vitro Modified oligonucleotides complementary to a human FMR1 nucleic acid at the two start sites for polyglycine (nucleobase 3001 and 3025 of SEQ ID NO: 1) were tested for their effects on FMR1 RNA and FMRP in HEK293 cells.
Experimental Procedure
Endogenous FMR1 expression in HEK293 cells was analyzed by quantifying RNA after treatment with 1006611 at 100 nM and 250 nM concentrations. HEK293 cells were transfected with a mixture of modified oligonucleotide and Lipofectamine© RNAiMAX. After approximately 24 hours, RNA was isolated from the cells and FMR1 RNA levels were measured by quantitative real-time PCR. The sequence of the forward primer was CATGAAGATT-CAATAACAGTTGC (SEQ ID NO: 2) and the reverse primer was CACTTTAGCTAACCACCAACA (SEQ ID: 3). Results are presented in the tables below as normalized FMR1 RNA level, relative to untreated control cells (these conditions describe a "Standard Cell Assay").
Endogenous FMRP expression in HEK293 cells, which contain fewer than 25 CGG repeats, was analyzed by Western blot after treatment with 1006611 at a 100 nM concentration. HEK293 cells were transfected with a mixture of modified oligonucleotide and Lipofectamine© RNAiMAX. After approximately 24 hours, cells were lysed in RIPA buffer with cOmplete™ protease inhibitors (Sigma). Lysates were heated at 90° C. in SDS buffer for 5 minutes, and resolved on 8% SDS-PAGE gel. FMRP was detected using anti-FMRP antibody ab17722(abcam). Western blots were quantified using ImageJ and normalized with GADPH.
Results
As shown below, Compound ID No. 1006611 each increased human FMR1 RNA relative to untreated control and indicates that Compound ID No. 1006611 is effective in increasing FMRP synthesis.

TABLE 5

Relative FMR1 RNA

| Compound ID No./ Dose 1006611 (nM) | Relative FMRI RNA Expression |
|---|---|
| 0 | 100.0 |
| 100 | 110.0 |
| 250 | 216.1 |

As shown below, Compound ID Nos. 1006611 and 1006613 increased the amount of FMRP in a dose dependent manner relative to untreated control as measured by quantified Western blot.

TABLE 6

Relative FMRP Abundance

| Compound ID No./Dose (nM) | Relative FMRP Abundance | | | | |
|---|---|---|---|---|---|
| | 0 | 25 | 50 | 75 | 100 |
| 761933 | 100 | 96 | n.d. | 123 | 103 |
| 1006609 | 100 | 100 | n.d. | 101 | 96 |
| 1006610 | 100 | 101 | n.d. | 88 | 102 |
| 1006611 | 100 | 118 | n.d. | 154 | 175 |
| 1006612 | 100 | 149 | n.d. | 127 | 115 |
| 1006613 | 100 | 119 | n.d. | 128 | 140 |
| 1006611 + 1006613 | 100 | n.d. | 93 | 55 | 58 | n.d. means no data.

Example 4

Effect of Modified Oligonucleotide 1006611 on FMRP Synthesis in Human Fibroblasts Compound ID No. 1006611 was transfected into wild-type human fibroblasts at 25, 75, and 100 nM for 24 hours and FMRP was analyzed by Western blot as in Example 2. An increase in FMRP synthesis was observed at all tested concentrations relative to untreated control.

TABLE 7

Relative FMRP Expression in Fibroblasts

| Compound ID No./ Dose 1006611 (nM) | Relative FMRP Abundance |
|---|---|
| 0 | 100 |
| 25 | 138 |
| 75 | 170 |
| 100 | 127 |

Example 5

Effect of Modified Oligonucleotides on RAN Translation in Cells with Disease-Associated Repeat Lengths HEK293 cells were plated on a 96 well plate and co-transfected with 100 nM modified oligonucleotide (Compound ID No. 1006611 or Compound ID No. 761833) and 50 µg reporter RNA (+1 (CGG)$_{90}$-nLuc-3'UTR or AUG-nLuc-PEST) and pGL4.13 (firefly luciferase reporter) using Lipofectamine©2000. AUG-nLuc-PEST is a construct that does not contain any of the FMR1 gene. Instead, it is a positive control for standard AUG-initiated translation of nanoluciferase attached to a PEST signal for more rapid protein degradation. pGL4.13 is a firefly luciferase reporter, which is used as a control for protein expression levels in the HEK293 cells. After 24 hours, levels of expression of nanoluciferase were measured as described above. Levels of expression of firefly luciferase were measured using prepared ONE-Glo reagent in place of NanoGlo and were used to normalize levels of nanoluciferase for total protein expression. The ratio of nLuc:FFLuc in AUG-nLuc-PEST cells treated with modified oligonucleotides reflects the effect of compounds on standard AUG-initiated translation. The ratio of nLuc:FFLuc in +1 (CGG)$_{90}$-nLuc-3'UTR cells treated with modified oligonucleotides reflects the effect of the compounds on RAN translation in the +1 frame in cells containing a premutation, FTAXS and FXPOI-associated CGG repeat length. RAN translation in the +1 frame leads to polyglycine expression.

No change in the ratio of nLuc:firefly luciferase was observed in AUG-nLuc-PEST control cells or in +1 (CGG)$_{90}$-nLuc-3'UTR cells treated with control oligonucleotide 761933. The ratio of nLuc:firefly luciferase was significantly reduced in +1 (CGG)$_{90}$-nLuc-3'UTR cells treated with 1006611 relative to samples treated with control 761933, representing a reduction in the production of polyglycine in these cells.

TABLE 8

Relative expression of nanoLuciferase and Firefly Luciferase

| Reporter DNA | Compound ID No. | % nLuc:FFLuc |
| --- | --- | --- |
| AUG-nLuc-Pest | 761933 | 100 |
| AUG-nLuc-Pest | 1006611 | 81.8 |
| +1 (CGG)$_{90}$-nLuc-3'UTR | 761933 | 100 |
| +1 (CGG)$_{90}$-nLuc-3'UTR | 1006611 | 34.6 |

Example 6

Effect of Modified Oligonucleotides on RAN Translation in Cells with Disease-Associated Repeat Lengths HEK293 cells were plated on a 24-well plate and transfected with 250 ng+1 (CGG)$_{100}$-nLuc-3'UTR RNA for 3 hours, and then the media was changed and cells were treated with 100 nM Compound ID No. 1006611 or control 761833. Media was changed at 24 hours and cells were lysed in 200 µL RIPA buffer 48 hours after treatment with oligonucleotides. Protein was run on a western blot as described in Example 1 and probed for Flag (mouse anti-flag, Sigma, F1804) and tubulin (mouse anti-tubulin, DSHB, 12G10). Expression of flag-tagged protein in this system represents RAN translation leading to the production of polyglycine. Treatment with 1006611 reduced the production of flag-tagged protein relative to samples treated with control 761933, representing reduced polyglycine.

TABLE 9

Relative Expression of Flag-tagged protein:tubulin

| Compound ID No. | Flag:Tubulin Ratio |
| --- | --- |
| 761933 | 100 |
| 1006611 | 60.5 |

Example 7

Effect of Modified Oligonucleotides on Neuronal Death in Cells with Disease-Associated Repeat Lengths DIV4 primary mixed cortical neurons (rat hippocampus) were transfected with 100 ng mApple and 100 mg+1 (CGG)$_{100}$-RAN-GFP RNA or GFP RNA with Lipofectamine©2000. The mApple RNA was used to normalize GFP signals. Modified oligonucleotides were added immediately after transfection at 1 µM and maintained at this concentration throughout the experiment. Automated longitudinal microscopy was used to track neuronal cell death over 10 days. Neurons treated with +1 (CGG)$_{100}$-RAN-GFP had significantly higher cumulative risk of death than those treated with GFP alone. Treatment of neurons with Compound ID No. 1006611 in combination with +1 (CGG)$_{100}$-RAN-GFP reduces this risk compared to neurons treated with control 761833. Results in the table below are presented relative to treatment with the control oligonucleotide and GFP-only plasmid.

TABLE 10

Relative Neuronal Death in Cortical Neurons

| Compound ID No./ transfected plasmid | Hazard Ratio |
| --- | --- |
| 761833/GFP | 1.0 (reference group) |
| 1006611/GFP | 0.88 |
| 761833/(CGG)$_{100}$-RAN-GFP | 2.48 |
| 1006611/(CGG)$_{100}$-RAN-GFP | 2.14 |

Example 8

Effect of Modified Oligonucleotides in Induced Pluripotent Stem Cells iPSC Cell Line Derivation & Neuronal Differentiation Induced pluripotent stem cells (iPSC) were derived from a previously established FMR1 patient fibroblast cell line, TC43-97, as well as control normal fibroblasts containing ~30 CGG repeats. TC43-97 contains a fully unmethylated FMR1 promoter with ~250-600 CGG repeats. Fibroblasts were cultured in DMEM, 10% FBS, 1×L-glutamax (Fisher), 1 mM MEM non-essential aminoacids (Fisher), at 37° C. and 5% CO$_2$. For episomal reprogramming, 1×10$^6$ fibroblasts were collected after Trypsin treatment and mixed with a set of plasmids pCXLE-hOCT3/shP53, -hSK, -hUL (Addgene), then electroporated with Neon® device (condition: 1650 Volts, 10 mm width, and 3 pulses). Induced fibroblasts were plated onto 6 well plates at density of 0.5-1×10$^4$ cells/well and switched 1 day later to a PSC medium mTeSR1 (StemCell Technologies). IPSC colonies appeared and were manually picked and passaged onto new matrigel coated 12-well plates, and continually grown with mTeSR1. IPSCs were passaged weekly using 0.5 mM EDTA and culture medium supplemented with 10 µM Y-27632 ROCK inhibitor (EMD Millipore) for 24 hours. After 5-10 passages the cells were evaluated for pluripotency by immunocytochemistry (ICC) and embryoid body differentiation. FMR1 RNA levels were detected with RT-PCR as described above.

For treatment with modified oligonucleotides, undifferentiated iPSCs were plated as small colonies on MatriGel-coated plates in TeSR-E8 containing 10 µM Rock Inhibitor and grown overnight. Media was replaced with TeSR-E8 the next day. Cells were allowed to recover for at least 4 hours and media was replaced again just prior to treatment. Oligonucleotides (0-100 nM) and RNAiMax (4.5 µl per 100 µl of prepared complexes) were diluted in Opti-MEM reduced serum media, incubated together for 5 mM at room temperature, and added to cells. Cells were harvested 24 hours after treatment.

Results

FMR1 RNA levels were normalized to 18S ribosomal subunit and compared between control iPSC cells and TC43-97 cells. As shown below, TC43-97 cells express less FMR1 RNA as compared to Control iPSC cells.

TABLE 11

Relative FMR1 RNA

| Cell Line | Relative FMR1 RNA level |
|---|---|
| Control iPSC | 100 |
| TC43-97 | 86 |

FMR1 RNA levels were normalized to 18S ribosomal subunit and compared between and TC43-97 cells and in TC43-97 cells treated with 100 nM 1006611. Results are presented relative to control iPSC RNA.

TABLE 12

Relative FMR1 RNA

| Cell Line | Relative FMR1 RNA level |
|---|---|
| TC43-97 | 100 |
| TC43-97 + 100 nM 1006611 | 158 |

FMRP levels, measured by quantitative Western blot as described above and reported relative to GADPH, are reduced in the TC43-97 iPSC cell line compared to the control iPSC cell line.

TABLE 13

Relative FMRP in TC43-97 cells

| Cell Line | % Relative FMRP Abundance |
|---|---|
| Control iPSC | 100 |
| TC43-97 | 11.4 |

Treatment of both control iPSC and TC43-97 iPSC with 1006611 leads to a dose-dependent increase in FMRP, indicating that treatment with a modified oligonucleotide targeted to the upstream +1 near-AUG RAN start site can increase FMRP in both normal human fibroblasts and human fibroblasts containing large FXS-associated CGG repeats.

TABLE 14

Relative FMRP after treatment with 1006611

| | | % Relative FMRP Abundance | | | |
|---|---|---|---|---|---|
| | Dose 1006611 | 0 nM | 50 nM | 75 nM | 100 nM |
| Cell Line | Control iPSC | 100 | 114 | 132 | 151 |
| | TC43-97 | 100 | 122 | 150 | 137 |

Example 9

Effect of Modified Oligonucleotides on Neurons Derived from iPSC Experimental Procedures Neural induction was performed using a dual-SMAD inhibition protocol, as described in Shi, Y., Kirwan, P. & Livesey, F. J. Directed differentiation of human pluripotent stem cells to cerebral cortex neurons and neural networks. *Nature protocols* 7, 1836-1846, doi:10.1038/nprot.2012.116 (2012) with some modifications. In brief, two wells of a 6-well plate were grown to approximately 80% confluence, dissociated with EDTA, and plated into a single well of a MatriGel-coated 6-well plate with TeSR-E8 containing 10 µM Rock Inhibitor (Y-27632). The cells were confluent the next day and neural differentiation was induced using neural maintenance media (referred here as 3N) containing 1 µM dorsomorphin and 10 µM SB431542. The cells were cultured for 12-14 days with daily media changes. Neuroepithelial sheets were then combed into large clumps, passaged, and maintained on MatriGel-coated plates in rosette media (3N containing 20 ng/ml FGF) with daily media changes until neural rosettes appeared. Rosettes were manually picked and dissociated into single cells using Accutase. Neural progenitors were plated onto MatriGel-coated plates, grown in neural expansion media (3N containing 20 ng/ml FGF and 20 ng/ml EGF) with media changes every other day, and passaged as needed using Accutase. For differentiation into neurons, neural progenitors were plated at a density of approximately $1.5 \times 10^5$ cells/mL in neural expansion media on PLO-laminin coated plates or coverslips, allowed to grow for 24 hours, and switched to neural maintenance media. Neurons were maintained for up to 6 weeks with half media changes every other day and a full media change supplemented with 1 µg/ml laminin every 10 days.

For iPSC-derived neurons, 150 nM oligonucleotide was diluted in neural maintenance media and added to 6-week old neurons one day after a full media change. Media was changed 24 hours after treatment. Neurons were maintained as above and harvested 6 days after treatment. Western blots were performed as described in Example 2 and normalized to GADPH.

Results

Treatment of iPSC-derived neurons from control or TC43-87 cell lines with 150 nM 1006611 leads to an increase in FMRP, while treatment of iPSC-derived neurons from the control cell line with the control 761933 does not lead to an increase in FMRP. The upstream +1 near-AUG RAN start site can increase FMRP in both normal human neurons and human neurons containing large FXS-associated CGG repeats.

TABLE 15

Relative FMRP Abundance

| Cell Line | Treatment | Relative FMRP abundance |
|---|---|---|
| Control neurons | Untreated | 100 |
| | 150 nM 761933 | 117 |
| | 150 nM 1006611 | 141 |
| TC43-97 neurons | Untreated | 100 |
| | 150 nM 1006611 | 156 |

Example 10

Effect of Modified Oligonucleotides on Immunofluorescence Microscopy of iPSC-Derived Neurons Neurons from the TC43-97 cell line and control fibroblasts were derived as in Example 6. Control fibroblasts contain ~30 CGG repeats, a length not associated with any disease state. Neurons were treated with 150 nM 1006611 or untreated. Cells were washed 2× in PBS containing 1 mM $MgCl_2$ and 0.1 mM $CaCl_2$ (PBS-MC) prior to fixing for 15 minutes with 4% paraformaldehyde/4% sucrose in PBS-MC and permeabilizing for 5 minutes in 0.1% Triton-X in PBS-MC. Cells were then stained for FMRP and the neuronal marker TUJ1 (mouse anti-tuj1, Covance, MMS-435P). FMRP expression is represented as corrected total cell fluorescence (CTCF). The average CTCF is binned for every 5 cells analyzed within a condition, the average of every bin is taken within that condition, and reported as a percentage relative to the Control neuron/0 nM group. This is reported in Table 16 below. The average intensity of both TUJ1 and FMRP for control neurons and TC43-97 neurons was also analyzed. TUJ1 intensity reflects the number of neuronal cells, and as can be seen in Table 17 below, was similar across treatment conditions. FMRP average intensity represents the amount of FMRP in the cells. These results suggest that treatment of neurons containing FXS-disease associated CGG repeat lengths with 1006611 can return FMRP levels to those observed in control neurons containing normal, non-disease associated CGG repeat lengths.

TABLE 16

Normalized FMRP fluorescence, average

| Condition | % Normalized FMRP fluorescence |
|---|---|
| TC43-97 neurons, untreated | 19.2 |
| TC43-97 neurons + 150 nM 1006611 | 55.6 |
| Control neurons | 100.0 |

TABLE 17

TUJ1 and FMRP Average Intensity

| Condition | TUJ1 Average Intensity | FMRP Average Intensity |
|---|---|---|
| TC43-97 neurons, untreated | 504.6 | 199.4 |
| TC43-97 neurons + 150 nM 1006611 | 496.2 | 429.1 |
| Control neurons | 553.5 | 453.6 |

Example 11

Effect of Modified Oligonucleotides on Immunofluorescence Microscopy of iPSC-Derived Neurons Neurons from the TC43-97 cell line were derived as in Example 6. Neurons were treated with 150 nM 1006611 or untreated. Cells were washed 2× in PBS containing 1 mM $MgCl_2$ and 0.1 mM $CaCl_2$ (PBS-MC) prior to fixing for 15 minutes with 4% paraformaldehyde/4% sucrose in PBS-MC and permeabilizing for 5 minutes in 0.1% Triton-X in PBS-MC. Cells were then stained for polyglycine. FMR polyglycine expression is represented as corrected total cell fluorescence (CTCF). The average CTCF is binned for every 5 cells analyzed within a condition, the average of every bin is taken within that condition. TC43-97 neurons+150 nM control 761933 condition included 93 cells and TC43-97 neurons+150 nM 1006611 included 194 cells. These results suggest that treatment of neurons containing a long (~250-600) CGG repeat at the FMR1 locus with a modified oligonucleotide complementary to the +1 RAN ACG site in the 5'UTR reduces the levels of of the RAN translation product polyglycine.

TABLE 18

FMR polyglycine

| Condition | CTCF (%) |
|---|---|
| TC43-97 neurons + 150 nM control 761933 | 100.0 |
| TC43-97 neurons + 150 nM 1006611 | 71.0 |

Example 12

Effect of Modified Oligonucleotides on RAN Translation in Cells with Disease-Associated Repeat Lengths in Reurons Primary rat hippocampal neurons were plated on a glass bottom, 35 mm MatTek plate and transfected with 2.5 μg+1 $(CGG)_{90}$RAN-Venus DNA at DIV5. Reporter gene+1 $(CGG)_{90}$RAN-Venus RNA is described in Example 1. Expression of the fluorescent protein Venus correlates to RAN translation that would lead to the expression of polyglycine in the absence of the Venus reporter protein.

Cells were treated with 1 μM Compound ID No. 1006611 or control 761833 directly following transfection. Cells were imaged after 5 days. Fluorescent signal corresponding to the expression of Venus in each neuron was measured. Approximately 40 cells were counted per each condition, and the control treatment was normalized to 100%. As shown in the table below, compound ID No. 1006611 reduced levels of the RAN translation product polyglycine as compared to the negative control.

TABLE 19

Normalized RAN fluorescence

| Compound ID No./ transfected plasmid | Normalized RAN fluorescence (%) |
|---|---|
| 761833/Venus | 100 |
| 1006611/Venus | 72.9 |

What is claimed is:

1. An oligomeric compound comprising a modified oligonucleotide consisting of 16-30 linked nucleosides and having a nucleobase sequence comprising at least 16, 17, or 18 nucleobases of any of SEQ ID NOS: 13-16.

2. An oligomeric compound comprising a modified oligonucleotide consisting of 16-30 linked nucleosides and having a nucleobase sequence complementary to at least 16, at least 17, or at least 18 contiguous nucleobases of an equal length portion of nucleobases 3001-3042 of SEQ ID NO: 1.

3. An oligomeric duplex comprising an oligomeric compound of claim 1.

4. An antisense compound comprising or consisting of an oligomeric compound of claim 1.

5. A chirally enriched population of oligomeric compounds of claim 1, wherein the population is enriched for oligomeric compounds comprising at least one particular phorphorothioate internucleoside linkage having a particular stereochemical configuration.

6. A chirally enriched population of oligomeric compounds of claim 1, wherein all of the phosphorothioate internucleoside linkages of the modified oligonucleotide are stereorandom.

7. A pharmaceutical composition comprising an oligomeric compound of claim 1 and a pharmaceutically acceptable carrier or diluent.

8. A method of increasing the amount of FMR1 RNA in cells or tissues comprising contacting the cells or tissues with an oligomeric compound of claim 1.

9. A method of increasing the amount of FMRP protein in cells or tissues comprising contacting the cells or tissues with an oligomeric compound of claim 1.

10. A method of decreasing the amount of a RAN translation product in cells or tissues comprising contacting the cells or tissues with an oligomeric compound of claim 1.

11. A method of preserving neurons in an animal in need thereof comprising administering to the animal a pharmaceutical composition of claim 7.

12. A method comprising administering to an animal having a Fragile X-Spectrum disorder an oligomeric compound of claim 1; wherein the administering preserves neurons.

13. The method of claim 12, wherein the Fragile X-Spectrum disorder is FXS, FXTAS, or FXPOI.

14. The method of claim 12, wherein the oligomeric compound is administered prior to detection of at least one symptom of a Fragile X-Spectrum disorder.

15. The method of claim 12, wherein the amount of total FMR1 RNA is increased in the animal.

16. The method of claim 12, wherein the amount of total FMRP protein is increased in the animal.

17. The method of claim 12, wherein the amount of a RAN translation product is reduced in the animal.

18. The method of claim 17, wherein the RAN translation product is any of polyglycine, polyalanine, and polyarginine.

19. The method of claim 12, wherein the animal is a human.

20. A pharmaceutical composition comprising an oligomeric compound of claim 2 and a pharmaceutically acceptable carrier or diluent.

* * * * *

SEQUENCE LISTING

<160> NUMBER OF SEQ ID NOS: 18

<210> SEQ ID NO 1
<211> LENGTH: 45000
<212> TYPE: DNA
<213> ORGANISM: Homo sapien

<400> SEQUENCE: 1

| | | | | | | |
|---|---|---|---|---|---|---|
| gtcttctgtg | ctgagaactg | tcagagaggg | tacaacagtg | gacagtgact | gcagggatac | 60 |
| cagcgaagaa | gttgctgcca | taatgcaggt | aagagaatgg | aagcttggac | tatggtttta | 120 |
| gctgagcaaa | tgatcagaaa | cagagtctgg | attctacaat | gatttgctga | tggatctgat | 180 |
| gtgtgaaaga | gggtcaaaat | gtctcagttt | taggcttgag | caacgaactg | gaaggcagga | 240 |
| gctgcctgta | acgagagaca | ggagagaaag | agagagagag | agagaggact | ttggaagagc | 300 |
| aggctcatga | tcaggcctga | gctcagtgtc | tgaattcagg | taagctatct | tgaaagggga | 360 |
| aatatcaaaa | gctagagatc | agagtaaggc | tgagactcag | agtcaagtgg | ggaagactaa | 420 |
| gttgcagtat | gtactggcag | tgaagataag | tatttattca | ttcattgaac | ataccttgaa | 480 |
| atcaaccact | tttaatgtgc | cagggacaca | agatagaaaa | agcatttgc | cctgtctgga | 540 |
| aggtactaat | aatccaataa | ggaaaacaga | aatataaata | aattattcta | gtacactaac | 600 |
| catcatagta | gaggtattca | acatttgttg | agtctctgct | atatgccaag | cagtgtaatg | 660 |
| aggaagcaga | gggtatgcac | aaagttctac | aagagcacaa | aataagttct | ggcaaaggtt | 720 |
| tgtaaagaca | ttcacaaggg | ttttcaccac | agtatgactt | cagggagttg | gcagtaacct | 780 |
| agatgcccga | tcagtaggga | tatgtatgaa | taaaatttct | ggcatactcg | gtagcaaact | 840 |
| aggtgtacac | acagcaatgt | gggtatagct | caaaaacaga | ctgttgagta | aaacagtggg | 900 |
| aaatagagat | ttacagtcca | ataccatctc | tgtaaatgca | agaggcataa | acaaaacatt | 960 |
| atctgtgtta | aattatcaag | gatctctatc | gaacatattg | cagcttgtgt | ctagaagaat | 1020 |
| gagagtgggg | atcgagaaag | atgaggaaaa | aataatataa | acactataaa | ataatgtaaa | 1080 |
| caaggaccct | gtagggactg | atatgacaat | gtgctgaaaa | ttgaggagca | aagttaactc | 1140 |
| tctgtacctg | agataaaata | actagctaat | aggaatccag | ctgaaaacct | taaggtgcag | 1200 |
| ggcctctatg | gggcccagga | aggatgtgta | gagacatgaa | cggatgaaag | tgcatcacag | 1260 |
| gttcagggaa | caacacaggt | tgagtgtggc | ttgtagtaaa | aatggttgtg | aagagttgac | 1320 |
| atattttaa | gccctgggta | aattgaacaa | cagcttacac | ttggagggt | ataatcattc | 1380 |
| taatcaatgt | gtcccctttt | actataatac | attggagttg | cagctaatgc | tctgctccca | 1440 |
| ttcagcctat | gatgagattc | tctttcagcc | ctattgggtt | cttggcctca | tgtgactact | 1500 |
| ccaaagaccc | tagtccaaaa | ggtctttcct | gtttgctatg | gccttgagga | atgtggccct | 1560 |
| agatccaccg | ctttaaagct | ggagttccac | cagcagcaac | atcctctcat | tctgggcac | 1620 |
| ctgcctgggg | caggtcatcc | tgcctctgcc | aactcagtgc | tattagttaa | ctctcacctg | 1680 |
| ccatattcca | gctggaatca | tctcccctc | tccaccccag | actaggtcat | gttccgccat | 1740 |
| catggaagcg | cctattcttc | ataccccta | tcacagctgc | aactactcat | ttacttgtct | 1800 |
| gacaatttga | tttatgtcca | cctactttgc | taggtactaa | gttcaatgct | ggcagtcgtt | 1860 |
| tcttcttttt | ttttctttc | tgttttgctc | accgatttct | cgttagcact | tagcacagtg | 1920 |
| tctggcacac | gatagatgct | ccgtcaactt | ctcagttgga | taccagcatc | ccgaagggaa | 1980 |
| catgattaa | ggcagctata | agcacggtgt | aaaaacagga | ataagaaaaa | gttgaggttt | 2040 |
| gtttcacagt | ggaatgtaaa | gggttgcaag | gaggtgcatc | ggcccctgtg | gacaggacgc | 2100 |

```
atgactgcta cacacgtgtt caccccaccc tctggcacag ggtgcacata cagtagggc    2160
agaaatgaac ctcaagtgct taacacaatt tttaaaaaat atatagtcaa gtgaaagtat    2220
gaaaatgagt tgaggaaagg cgagtacgtg ggtcaaagct gggtctgagg aaaggctcac    2280
attttgagat cccgactcaa tccatgtccc ttaaagggca cagggtgtct ccacagggcc    2340
gcccaaaatc tggtgagaga gggcgtagac gcctcacctt ctgcctctac gggtcacaaa    2400
agcctgggtc accctggttg ccactgttcc tagttcaaag tcttcttctg tctaatcctt    2460
caccccctatt ctcgccttcc actccacctc ccgctcagtc agactgcgct actttgaacc    2520
ggaccaaacc aaaccaaacc aaaccaaacc aaaccagacc agacaccccc tcccgcggaa    2580
tcccagagag gccgaactgg gataaccgga tgcatttgat ttcccacgcc actgagtgca    2640
cctctgcaga aatgggcgtt ctggccctcg cgaggcagtg cgacctgtca ccgcccttca    2700
gccttcccgc cctccaccaa gcccgcgcac gcccggcccg cgcgtctgtc tttcgacccg    2760
gcaccccggc cggttcccag cagcgcgcat gcgcgcgctc ccaggccact tgaagagaga    2820
gggcggggcc gaggggctga gcccgcgggg ggagggaaca gcgttgatca cgtgacgtgg    2880
tttcagtgtt tacacccgca gcgggccggg ggttcggcct cagtcaggcg ctcagctccg    2940
tttcggtttc acttccggtg gagggccgcc tctgagcggg cggcgggccg acggcgagcg    3000
cgggcggcgg cggtgacgga ggcgccgctg ccaggggggcg tgcggcagcg cggcggcggc    3060
ggcggcggcg gcggcggcgg aggcggcggc ggcggcggcg gcggcggcgg ctgggcctcg    3120
agcgcccgca gcccacctct cggggcgggg ctcccggcgc tagcagggct gaagagaaga    3180
tggaggagct ggtggtggaa gtgcggggct ccaatggcgc tttctacaag gtacttggct    3240
ctagggcagg cccccatcttc gcccttcctt ccctcccttt tcttcttggt gtcggcggga    3300
ggcaggcccg ggccctctt cccgagcacc gcgcctgggt gccagggcac gctcggcggg    3360
atgttgttgg gagggaagga ctggacttgg ggcctgttgg aagccctctc ccgactccga    3420
gaggccctag cgcctatcga aatgagagac cagcgaggag agggttctct ttcggcgccg    3480
agccccgccg gggtgagctg gggatgggcg agggccggcg gcaggtacta gagccgggcg    3540
ggaagggccg aaatcggcgc taagtgacgg cgatggctta ttccccctttt cctaaacatc    3600
atctcccagc gggatccggg cctgtcgtgt gggtagttgt ggaggagcgg ggggcgcttc    3660
agccgggccg cctcctgcag cgccaagagg gcttcaggtc tcctttggct tctcttttcc    3720
ggtctagcat tgggacttcg gagagctcca ctgttctggg cgagggctgt gaagaaagag    3780
tagtaagaag cggtagtcgg caccaaatca caatggcaac tgattttag tggcttctct    3840
ttgtggattt cggaggagat tttagatcca aaagtttcag gaagacccta acatggccca    3900
gcagtgcatt gaagaagttg atcatcgtga atattcgcgt cccccttttt gttaaacggg    3960
gtaaattcag gaatgcacat gcttcagcgt ctaaaaccat tagcagcgct gctacttaaa    4020
aattgtgtgt gtgtgtttaa gtttccaaag acctaaatat atgccatgaa acttcaggta    4080
attaactgag agtatattat tactagggca tttttttttt aactgagcga aaatattttt    4140
gtgcccctaa gaacttgacc acatttcctt tgaatttgtg gtgttgcagt ggactgaatt    4200
gttgaggctt tatataggca ttcatgggtt tactgtgctt tttaaagtta caccattgca    4260
gatcaactaa caccttttcag ttttaaaagg aagatttaca aatttgatgt agcagtagtg    4320
cgtttgttgg tatgtaggtg ctgtataaat tcatctataa attctcattt ccttttgaat    4380
gtctataacc tctttcaata atatcccacc ttactacagt attttggcaa tagaaggtgc    4440
```

```
gtgtggaagg aaggctggaa aatagctatt agcagtgtcc aacacaattc ttaaatgtat    4500
tgtagaatgg cttgaatgtt tcagacagga cacgtttggc tataggaaaa taaacaattg    4560
actttattct gtgtttacca attttatgaa gacatttgga gatcagtata tttcataaat    4620
gagtaaagta tgtaaactgt tccatacttt gagcacaaag ataaagcctt ttgctgtaaa    4680
aggaggcaaa aggtaacccc gcgtttatgt tcttaacagt ctcatgaata tgaaattgtt    4740
tcagttgact ctgcagtcaa aattttaatt tcattgattt tattgatcca taatttcttc    4800
tggtgagttt gcgtagaatc gttcacggtc ctagattagt ggttttggtc actagatttc    4860
tggcactaat aactataata catatacata tatatgtgtg agtaacggct aatggttagg    4920
caagattttg attgacctgt gatataaact tagattggat gccactaaag tttgcttatc    4980
acagagggca agtagcacat tatggccttg aagtacttat tgttctcttc cagcaactta    5040
tgatttgctc cagtgatttt gcttgcacac tgactggaat ataagaaatg ccttctattt    5100
ttgctattaa ttccctcctt ttttgttttg ttttgtaacg aagttgttta acttgaaggt    5160
gaatgaagaa taggttggtt gccccttagt tccctgagga gaaatgttaa tacttgaaca    5220
agtgtgtgtc agacaaattg ctgttatgtt tatttaatta agtttgattt ctaagaaaat    5280
ctcaaatggt ctgcactgat ggaagaacag tttctgtaac aaaaaagctt gaaattttta    5340
tatgacttat aatactgctg tgagttttaa aagtaaagca aagtaaaact gagttgcttg    5400
tccagtggga tggacaggaa agatgtgaaa taaaaaccaa tgaaaaatga actgctgtgg    5460
agaagtgtta catttatgga aaaagaaata ggaaccttgt tcatcaaatt gatagaaaag    5520
cttttaaaac taaacaaatc aaacaacttg agtataatgg aattcagact ttgatttgcc    5580
taacataacc accatatttg caaggacagc tctctatctt ctggtgttta ttcttaaaaa    5640
cttaaaagtt agatttagcg atcaccagag ccactacttt tatgcttagg tatttgtttg    5700
acttagaaaa aattggtcac gtgtaccact ttatagtgcc ctgcaggtgt taagatatga    5760
aggcactttg acttacacct cataaaatct ttacaaagta ttttctaaat gaataatgat    5820
gaaataaagt ctttattcta ggtgcatctg ccccacataa tttgttttct tggactaga    5880 agttttgatg tgttgagaat ggtaatgaat taactccatt ttaaatgtag aatgcgtatc    5940
actccaatat gaatgcccta atgaatccta agatttgtag gttttgtgta ctagtatgaa    6000
aattactaaa gatggaaaaa tcacatgttg gagacataag atacaaacct ttttgttttc    6060
tgaaaataca acctctgatt tctgattcct tgttgtaata tggtgtaatt atactagatt    6120
gtaattttgt tgttagatta acttttttta agttcagtgt ttgaggacag actttcattt    6180
ggttagtagt attatggcag ctagcagcta aatatgataa agtgtacaat caaaaggata    6240
tttttaatga agatattagt ggtctaacat gtcatttcag atacatagct gaaatgtagt    6300
aaaatcagtt ttactacaaa taaacttgca taaggtttat aaatttataa gtttataaat    6360
caacttgggt aaagtgtaaa taacttgca ctcgtggttt ctctgaagtc tcctgagcta    6420
actttgcata aaggtgttat tctgtacttc gaggaagtga attattgggg tcaaccacat    6480 ttttttttcct tcctacagtc tgattgccct tttagttttt taggatcttt gtggctgcat    6540 cattttccc cttttgaact gtgcattttc taaccccata cttaaatatt ctcataacct    6600
ccaaattatt aattagatgc aacattcagt ggtatattac tggagtttct gatttctgcc    6660
cactatagga atgtgcttcc tgagaagatt gggatcgtga ttataataat agttaacagg    6720
ggatgagtac tttctaggtg ccaggcactg ttctctctga tacttatttt gatgtattgt    6780
tgttattccc attcttaaa tgatgcacag agaggttagg taagtgactt actaccaagt    6840
```

```
gtcagggcca ttaagggtca ggattctgaa ttcctgaaat gatgaaattt agcttgaaga    6900
aattggtttg atttcctgct tagttttcaa tttcatggtg gtctttgatt gtattttgtg    6960
ctataacact gccttagcat cctataacta tagttacagt gttatattac cattttttat    7020
tgttaataca aagccatcat gaaataattc agtttatgtg ccagctttt ttgttactaa     7080
ttcttgaacc ttggcgctgt acttcttcat gtggatgcct gttaaggaaa gataaagtta    7140
gaaatctttg accctgctag gaaatttgtc tttgttatat tgggagctca taaaactgaa    7200
gtattcaaaa gttagaatac atacacacaa gaaaaattag taactaattt aataatgttt    7260
tctttgcaca tgtctctgtt gtcttttggt cagagtgaag ctaaatgtgt ttttcacata    7320
atttgtagcc tatatgaagt cctggacatg tggtatggtt ggaaggactg ttgatgaggt    7380
ttattgtctc tctttattct tttatgttgt tagtgtcccc atacaacggg gcgggggggag   7440
tggggacaaa atgataactt gctttatata tgaagccttg ggtttgaatc atactgttat    7500
cacatttcct atgtccctat cctgtctcct gcaggttttc tttcttggtt ttctttttg     7560
gttttctttc ttcctttctt cctttctttt cctttctttc cttctttcct tttttctttc    7620
cttttctttt ttcctttctt tccttcattt ctctccttg ctcctttagt ttgtttcttt     7680
gtttctttgg tttgtttctt tgtttctttg gtttgtttct ttgtttcttt agtttgtttc    7740
tttgtttctt tgtttctttc aacaggtctc actgtcgccc aggttggagt gcagtggtgg    7800
gatctcagct cactgcaacc tccacctctc gggttcaagc cagtctcatg cttcagcctt    7860
ccgggtagct gagattacag gcatgtgcca ccattcctgg ctattttttg cattttagt     7920
agagatgagg tttcgccatg ttggccaggc tgatctcaag ttatctgcct gcctcagccc    7980
tccaaagtgc tggaattaca ggcatgagac accgggtcca gcttccagca ggttttcttt    8040
aggagggata ttttacaatg ctgtaagttt ttcctaacga gaattatcat agcactacat    8100
gttctgtctt cagtaagtga tacaagctta ctgatgatgt tgtagttatg ttcattggtg    8160
gtcgggtgta cattgaaact ttaacacata atagcctctc ctgtgagcag tggttcctgt    8220
tggtaagata ctttactaag ggaaggaatg tgaggtgtcg ctggggagag tttacccaaa    8280
taaggatgga ctttctgtct ttgtttcatc agtcctggta atagaatgtt tgaatagata    8340
gctctaggca ttacatactt tcataaatat gattattgta attacctctt tggcccagtt    8400
gctagtaaat tagggacccc ttaatgattt atttcctgtt tattcaccct gatgaagaac    8460
ttgtatctct tttaaactgt actttatcgc ctttctcaaa ttccaagatt ctcatcacat    8520
tttttttctt cccaaactct aaataacctt ttaatattaa gtatctttgt ggaaacattg    8580
tttctttttt ctatcccaat ttttaaagct ttttaaaaa aagagtgct tttgttggga      8640
tgtacatttt ccaaatgcaa aaacatttat gattctgtgt ctcttataaa atatgacact    8700
ctctactttt ctctcatta tttagtgcca cctatgtgtg taatttcatt acccacagca     8760
gtcttaggag gctggtcgag ttccttattt gcagatgagg aatctgaggt ccagagatca    8820
cttcttggtg agagtctcac agctattaag tattagagcc aagattttga acgtaggtct    8880
gattcacagc aaaaccgtta accactaagt acactgactc cagtaagagc cctagtcctc    8940
acccaataca ctttaattcc cctgtgcatt cattcaaatt cattgaattt gctgcctttg    9000
gaaacctctc aggaacctcc tcaacctctc ttctctacag acatcagctt tgcctgatag    9060
gtagggatca tagcaaaaca cagttttcca aggtggtgat aggtgagtg atagtgctct     9120
ggagatggcc aaagaaggaa ggtatgagtg tatctgtggg tgggtgagtg gtggataagg    9180
```

-continued

```
ggaaggacag agccaaaagc gacggctatt ggaaaaacta tgatgagaaa caggaagatg      9240
gaaccttgtt ggaattagtg aaagacctta gaattcacag gaggtatttg tccttcacgc      9300
gagtgtagac caaacgtaac ctatgagttt cttttattcc acttattaaa gcagcaacca      9360
aaggtattat ataccttctg tattcactta aaatgactga ttttgaaaaa gtcatgcaaa      9420
catccattta cagataagcc tcattaactc aaaggcagtg gccctgttgg gctctgatga      9480
ttactcaaac catttctgac actctgacac tacatccgga aatcatccgg aaatgcattc      9540
agagcctgca aaagcttttt tttttttttt tttttttttt gaatagctac agcacttgca      9600
gatcttcctc ctttgagaga atatttgatt ttaggaaata agcaaatgta gataagtatg      9660
attcaactgg gcaataactt ttaggcaaag agaaaaaaac aaaatatagc aatgtagtaa      9720
taaggctgat attatagtgc ttttatgatg agtctgaaaa cagtctccaa catttgtaaa      9780
tgttttaaat cgggtctgtc tactacagta gcccttaagc catatgtagc tattgagcac      9840
ttgacatgtt gcaagagtga attggagact gattttaatt ttatttaatt ttaatgtaag      9900
tagtcgcaca tgacccgtgg ctactatggt agatggcata gttttagaca agggcagtag      9960
tcttgggtag atacttgatt tacttagaac atttctttac ctagctgtaa caaggttcta     10020
atagctgatt aaaggacaac attttttagca tgtaatatac agtaaggaac taatgttaat     10080
tactgccaag atgtataaac attatgaaac cttaacaag gatgaacaca gaagcagtgg      10140
cccttctttg taaataaggg gtcagttact tcctaatagg tgtcttagtt ttagttaata     10200
atctaatagc accccccaaaa agcaaactgt taatttgtta ttagccatcc tgtaaagaca     10260
agggagaaat cggggccagg agagtcctct ttcccattct ccataatttt tacgacctat     10320
agaaataaga gcctaagagt gaccagttcc tgcaacctaa ctcaaaatta ggcctctctg     10380
ttgaagtaat agtgaggcaa acaatcccctt gaagcactgg ggcatgcacc cttatgaaat     10440
ctaataattc taaaatatca ttggcagtat taagctagag ttctcaaaat atgctgtaga     10500
aaatattggt catttaaata tagctgagta aaaataagca agatcaaaat gataagaaaa     10560
tgttgatttc tccccttttg aaccagtaac taactataag ggtatatacc catgcttaac     10620
ttaaaaataa ttatttagcc accttgggta tagcacaaca tatggatgcc attatagtcc     10680
accttgatct tacaaggaag ctttctttta gcgtagcttt acttttattt aagcattatt     10740
gaagaagctt ggtatctctg tttaagttgc ttctgtatca gtgttttcca gggccctgtc     10800
tcagcttcca tagtttttct taagagcagc taattaatgc ttcactccat atgctttaat     10860
ttgatatttt gggaagtttc attttttaaa ataatctttt tatatcatag gcctttgaag     10920
acatatttgt ttacaaagac atctgcattg aaccatttgt tttaaaaac atgtatcggg     10980 catgttctat ataccagaaa ctatgccatt tactgaggac accgaagtta gagaatggtc     11040
ttaatccgaa ctagttattg tctcactatc caatatggat atcaaacatt cagcgtcatg     11100
aggatttact actgtgtttt ctcccaagag ttttataatt ttagctctta tatttaggtc     11160
tttgatgcat attcattgat ttttttttgt atgcagtatg aggtaaaggt tgaaacgtat     11220 tcttttttgca tgtgggtgtc cacttgtccc agcttcattt tttgaaaaca ctatactttc     11280
cccattgaat tgtcttggct tctttgttga caaggattt attatttctg ccacaaccca     11340
gctgtttctc actgtctaaa cctttatgcc tgctgccccg taggcttagt ggaatgcctc     11400
tccatcctcc actctctttt gtttagctag tacttcctta tcctttaagg ggtcagtagg     11460
aacctcacct tcttcagtat gttttccttt gtcttatcaa cctaccacca tcacccacac     11520
acataccttt tccctaaggc tgggatagga acctcttagg caatgatcta tttgataagt     11580
```

```
actcactgag ttcatactag acactctgca gtatatccgt aaatgaagta aaacctgaca   11640 ccacccctcag aaaacttact gttagtgaga aaatgggcta taataataga gtggggtaag  11700
tttattgtag ggataagcat aggatgctat gagaatgcag aggacaggaa tttaacctag   11760
acttctcagt tctcccgttg aagttgacat ctgaactgaa atctggaaga ccagtaaagag 11820 atagctatgt aaaagagggg aaggacaat aggaagaag gaatggagag aggcccagaa    11880
actacagagt atggcacaag tagtttagca ttgttgggtc acaaattcta aggatatgaa  11940
agataaagtt gaagaagtgg tggggctggg gaggacagct cctgtagagc cttttacagc  12000
gggagaagga gtttggctat ggtcctgcag gcagggagaa accactgaag gggagaaaca  12060
tacagaataa atttgagtaa gaagcttaaa tctccccaag cccttttaaa ataaattaag  12120
atataaagcc tttgggtttc tttatgcttt gtcctattct tctaattgtc caaaacaaaa  12180
caaaaacctt cctttctgt acctattaaa aggttaattt tataaagtta cagacagcat   12240
gctgattaaa gaattcttga taattagcta ttttgtctgt ctttgtgtag attactaaca   12300
attgtgtcat cagattaaa agatctaaac ctctggactt tatatatttt ttctacaagt   12360
actgtgagat tgagaactta attcaactct agtaactgga cttttagtg ttgtttgcag    12420 catatgattg ttaaagaaag tttagtatat ttgtgtgtgc gtatatatat atatatagat   12480
agatagatag atttgaggtt atatttaatc attgactatt ggtattctaa gattttaagg   12540
agagaaaggt aggttacaat atatggctga tatatggttc tggaacaatt ttcttagttt  12600
tcagtaattc tacctaaaat gtacgtccag ctttgcactc actaccacat tgtaattttcc 12660 agtatacttg tctattttc gagatgttga aatctgtgga gaattttttc tcatgtttag    12720
tgttttagct atgtttatct ctagggtata gcacatacaa ggtggcaata tagatgtgct   12780
taatgaataa aatgatcttc aaaaactgac cttcatttga agttctattt tattcataaa   12840
cacataaaac gtttggtatc actgtaaaat ttaactaaaa acaaaaacta tcttttaagct 12900 cacaagttaa tttaacgttt tttcttacac aggcatttgt aaaggatgtt catgaagatt   12960
caataacagt tgcatttgaa aacaagtaag tgtctcgtta tataatttta atgatgaggt   13020
tctttaatat tttatgctaa ttctactctt catttttttaa aaattcaagt ccagtttgag  13080
tgcttttcag gaatggatct tcatgttact gactgagaag tttctgaaca actcagtatt   13140
aaactaatgg aatgactgtt tctgctaatg tcctggaggt cccttattgt atggtattga   13200
tccttacgtc ttaattccct tgaatgtgaa gaaagaaacc agagagtctt gtgtattagt    13260
aactggaagt tcgcatagga gtatttgtaa attttaaaaa gatagtaatg aaaagattca    13320
tgggtattgc taaaaagttg tatgtgagtt ctttaacatt aaatctaaaa ctgatggttt    13380
tagttgtcta gtatatttta tggaaacagt catgttacc tattatctga ttttttttaa    13440
tgtttcatat gttcagcaat agcagtagct gatctttct gttctctttt gctagatgaa    13500
gaaataaaaa cagtcatagg cctaggaata ttaactgtat gaaagcatca atagtataga    13560
tgttaacatt ttattggaga acacaagtct cttgactaaa tgttttgaat gctaataaag   13620 gctatttttca gggtagctgt tggtaagatt gtaaagtaca tataaactcc ttagtcaaag  13680
tgtagatgtg gctatgatct taggattta ctaaactctg atggatggtt aacagttatc    13740
atttttttgg ctcttatata ccaagaaaat taataatata tcaaaagcag gctgcaaatc   13800
tatagagaca gaaagtagat tagtgattgc ttgtgctggg gctggtgggg agaacatagc   13860
taaagagtac aggattttg tgtgtgtggc aatgaaaatg ttgtaaaatt gactggtaat    13920
```

```
tattgcacat aactgtaaac cttctataaa ccattgaatt gtacatttaa attgatgaat    13980
tataatgata tgtggattat gtctgctaaa atgtagtatg tgacccaggc atactgagca    14040
ataaatacac acatcttgct tctaaagttt aaaaccaggc ctgtgtttca gtgtctagaa    14100
aatatatttc ataattgaac ttagcagatt cttttggcta gcaacaggac aaagtagtat    14160
ccttagatgc ctgaaacacg tgtaggggga cagagataaa aggattaaaa gcatctaacc    14220
ctatttctgg ctctggacta ataatcgcag accaaaatac aagtttgaat agtagaatac    14280 cttttccctga atacataaag ccaaaagttt tagtatttgt ctcttcgctg tttcatatat    14340
ccatggctat gcaatagaca acagcatcac accaacagag gaatctttga taacttggag    14400 ggtattttt tcttacaatt atacacttta tctacttact tacatcacta ggtaaatgct    14460
gtttcccata aagggagagt tgtctttatt tgctactctt ttagtttttc ctgtagtcta    14520
taatctaaag tgttaagcaa acactcattt cctctatgca tttaagaatt tgtctagttt    14580
atacattgat ttattagatc acttcttttt aattttcaat cagatttcta ccataaactt    14640
aaaattattt catctttgga ccttccaatt atttatctcc tgtaccatat ctgcatgaaa    14700
gtttctcttc aagctcttg tcatcctggg agtttgaaat agatcattga tttttccttg    14760
tgttcatgga gtatgtttgc aatacaacac tgggtttgag cacatcaata ggatttaata    14820
ggtctccacc aaagtaatct ctttgcccctt ccttgtgtgt ttccttttttg gttttctgtt    14880 agaaacaaaa cgaaaacagt gttttgtaaa acaccagatt gtatttaccc tttctttcct    14940
ttcaatcagg aagaagctcc tgttactgat agcagattgt tttaggtgct ttgttttttag    15000 gtgcttccta aaccttccat aaagcataaa ggtgttttca tatttcacat ttttttaataa    15060 ggaatttgaa ttttatcttg tatacactta aaatcattat tttttccttg gaaccattga    15120
gttatatatt attatatgct ttaaaatcaa atttagcaat gaatgtataa catctattag    15180
gtgtgtataa taactcagag gagggttcag ttaatttagg ccctaatcag atttccacaa    15240
attctgactt aatatttgcc cgcttatata acagctcttc tttaacaaaa acaagtactt    15300
ttctcaatag aattttacta agaaagctct ttagtaaaac atcgacatta tacatacaac    15360
atatctcagt atctgctgat gaagaacacc aaaaagaacc cagatgtgac tgctccggaa    15420
gttgaatcct cagtattttt gcaaagtttg tctttcagta ttttatttgt gtgtgtgtgt    15480
gtgtgtgtgt gtgtgtgtgt ctatatatat atatattttt ttttttttaa agacaggatc    15540
tcactctgtc acctaggctg gagtgcagtg gcatgatcat ggctcactgt aaccttgaac    15600
tcctgagctt gagctatcct cccacctcag cctcccgagt agctgggact ataggcacat    15660
accactgcac ctaattttt tttttttta ataatttgtt gtaaagatca ggtcttacct    15720
tgttgcccag gctgctcttg aagtcctggc ctgaagcagt gctcccacct cagcctccca    15780
aagctctggg attataggct tgagccaccg catcctaata ttttatattt ttatggatat    15840
aaaaaataat ttggtatctt tcagagttgt ttaatatcat tttaaattta aaacataggg    15900
caacttaaac tcctataggc tgtctccatc gggtttctgt ggtttaggag accccaccat    15960
cccagtgcat gctgataacg tcatactgat cagcatccag ctacccacag caagaattga    16020
ccacctcgtg ggatctaaaa tttaaggggg gaaagtgag ttgtgaattg ctaatgtgct    16080
gatagcccca ttttgcttgg gaattagagg gcagttttttg tggtccttgg aatgtggtta    16140
aaattcttct gcaagtggaa gcatatttat attactaaca attactggta ctaatattca    16200
aatattgaag gaaatttctg ttgtggactt atgtttaaag ctcttagaag ttgaaattat    16260
tggaaagaag acttgttttg aaaatcataa tgttgctgta ttgtgtttag agaaatattc    16320
```

```
caaacgggag taggctgctg tgctgcatgc agactttgct gaaatgttac tatattgccg   16380
ttatgtccca ctcagcaaaa actgatgatt ttaaagcttt tgcttcttga aactagaaaa   16440 agagggtca gccttaacca aaagttgatg gcagagtggt cattatttca gttaaacatg    16500
aaaagcatgt taaataattg tatgtttgct tatttacagc tggcagcctg ataggcagat   16560
tccatttcat gatgtcagat tcccacctcc tgtaggttat aataaagata taaatgaaag   16620
tgatgaagtt gaggtgagtt ttccctgcca taaagtcatt tagcactgaa agagtggggt   16680
taatttatct gtgttttttt ttaatacttt gtctttaaca ctgtttaaat tactttgaga   16740
attacagctg gaatggacac gtgcttttga ctaactcatc ttattaataa ttcaaaatga   16800
tacatgatgc ttacatttgg ctatttgagc agtactcaga gcatgtattt gaaagtcact   16860
gccgcaagtt cctttgccca ctagtaattc tttttctcct ctctcaattt ctgaatcttt   16920
gaatagtatg ttgtttgttt acaactgtgt ccccattgta agcaaaatgg attatgaaaa   16980
ttaattttac acaggaaaga aatcatgctt tattacaaaa tagtatacta gaatttcttt   17040
aagtagcagt gaatcttctt ggtatatttt taaaaaccta caagctttag tttatacata   17100
ttggtaaaat ctctttttca caggttatac cgtgaactac ctgcttatct cccgttgagc   17160
tctttgacca aaatgtgcta tggagatcta acatgtgaac agaaatgttg tgtttgtgat   17220
ttctttctcc attagaaatt ggttttgtat ttaaggcgct tacagtgcct catatagttt   17280
gtgtggtatc ttctctcctt tgtatccttt cacatactcc attttgagct gcttctcttc   17340
tttttctaca ataataagca taatgcctta ctattagtta ataatagttg ccgttccatg   17400
aatatttgta gtatgaagga tgtcgctaag tagacatttg tgcaggtgag gcagagtggt   17460
tctaggtcct gtccttcagt tctttattta tttatttatt tatttttttga gatggagtct   17520 cactcttgtc atccaggagt gcaatggcgc gatcttggct ccctgcaacc tccgcctccc   17580
gggttctagc gattcttctg cctcagcctc ctgagtagct gggattacag tcgcccacca   17640
ccacgcccag ataatttta tatttttagt agagacgggg tttcaccatg ttggtcaggc    17700
tagtctcgaa ctcctgacct caggtgatcc actcgcctcg gcctcccaaa gtgctgggat   17760
tacagatgtg agccaccatg cccagctggt ccttgaattc ttatttgctg cactaggtag   17820
taaaggtgta gcaaaaacag gacagaatct tctgcctttg atgaaatcac attccagtaa   17880
ggatagctaa tatgacagat gtgagtctta aagaaaaaaa aagggagagg atgaaaggtg   17940
atttagggac aggattgctg tttcagagag tagtcaggga agatctctca atgtccaggc   18000
ctgtgttttt ctctctacag ttttaaagtg gacataggat atagtgttat ttattttcca   18060
aaaatgtaac caatctctac taggtgtaag cagctgggct tggttttgca agggatctta   18120
atagggaaca gaaacactgt gtatgcttag ctgtccactt ccccagaaga ctgtaagctc   18180
tctgaaggca agacccaggt ctttggtctg tattaggagt acccagaata gtgtttgatg   18240
gagggatgaa agggactttt tctccccagc ttggtcactt gacagatcgg gaccaatgag   18300
ataccattgc taggatgacc tcactgtctt acacaccgat tcgttgaggt aatttctctg   18360
gctagagtag ttgagaaaga tggaagcaag agggaaaggt atgttaagtt gtattcagtc   18420
actgtattgt gtgatcatta actttggttg taaaagggag acaagttcga gcttttactc   18480
tacttgtcag ccctagactt tgtacctctc ttggcctcat gtctttatcc cccttgtctt   18540
tcttatttct cttttctgct tctgagtatc cctgtctctc tgtccatata tactctgttg   18600
tctcttttcc tattaacctt gatttgctag ggtcttcatg aaaggttcca tgctgtacat   18660
```

-continued

```
cttaagtgaa ctttgaagtg gtcatcaaag agatcagtta gaagaactga tctgcagtgt    18720
gtgacagacc aggaaagtga tatccagagg attgccacca tgaagttgtc attttttagtg   18780 gagaggaagc aggagaccag aaagtgacca aggatctgtc catttagttc caggagatat    18840
gactgccaga gtggtatcct tagtgggctg aatgttcagt ggtcttactt tagtgaccaa    18900
gcaacaagac agtagggcat ggtcagtaac tttcagtcaa ttttttgctta ctaggataaa   18960 gcaaaaataa gcttatacat ttttagatac attttttgta acttgctgag tacccaagga   19020
aagtgtgctt gtatttatgg gcgtctattt tcagagcact aattattgct gaattagaac    19080
agaaatatag gaaaactgat ttttacaagg agcttcaaag caatctcagg tagtttctga    19140
ttatgtatct ctgcctacct cggggtacat agacagggtt acaatttggt tgaggatata    19200
tgacatgtgg ttttttaaaga cacctagggg cattttaaga aaatttcctc gatatctgaa   19260
aatctgtaga tttcaaaatt atgttaatca tgaaatattc tgtgttgtaa ttttttgtgta   19320 ggtgtattcc agagcaaatg aaaaagagcc ttgctgttgg tggttagcta aagtgaggat    19380
gataaagggt gaggtaggaa aatgcctatt taaatttttt tcttatattg tttccttttt    19440
ttaaacccag gttgtacatt cccgtgtgga tttctatttt gaagtaatat ctaattttga    19500
gtaatttaat taaaatgttt tcactatgtg ttcagtatgt ttctgttggt cataaatttt    19560
ttcacataga ttatttattt taaaataact gaatagggag aacttcttat tcttacttta    19620
aaaattgtga ttagaagtga cttttattta tttctcagtt ttatgtgata gaatatgcag    19680
catgtgatgc aacttacaat gaaattgtca caattgaacg tctaagatct gttaatccca    19740
acaaacctgc cacaaaagat actttccata agatcaagct ggatgtgcca gaagacttac    19800
ggcaaatgta agttgataca caagaaatgc tgagaacttg gaagtgatat gcaattagtt    19860
tagaagaatt tctagtagtt taaaattttt taaactacta gaaattgatt ttaaatttgg    19920
tggactttgg caaaatggt ttggtttgca agagcaatgg agaaaaaact tatttaactt     19980
ttcctactta tagaatcaag gcagccttgc gcttgtttaa acttacttgg ctatacacgt    20040
gtctgatgta cataatgtac atttgttttc taaactaact ttgttcattc taagatttaa    20100
aaactgatca aacaaatgtg ataattctgt cataagtcac aaactataaa cgatttctcc    20160 gttttttttct cttttaccta aaatgttttc agataaatgt gtaataagta gagccaaaga    20220
agctttaaaa agtcatctca tcttacaatc cttgatctgg aataatgctt aaagactata    20280
gaagagacgc attttttattt tttacagatt ttattaagtg aatacagtac gtttgatttg    20340
gacatgttgt tgaacattaa attgcagttc agaatacata gaaatcctcc cttttctaga    20400
gattgtgtat gtgtgtaaat ttttgtgcct tctggttcat gtacgtttcc ttctctccct    20460
caaatcgttt agcagtttct taccccattc tccgtgatgt gcttatttca tattgcatgc    20520
ctgtatcaaa acatctcata tgccccataa atatatatac ctactatgta cccacaaaac    20580
taaaaattaa aaaaaaagga aaaaaaaagg cctgcaacaa gagaagaaga aagaaatcag    20640 atacccctgta ggtagctatc tccaaaagtt ttcaatagtt gacttaagaa aactactgac   20700
ttgtatgtaa ctgaaatcag gaaacctgta gtgtagagtg gttcccctga atatgtctct    20760
tttggtaatc taagctgtat ttcagaaatg tacagaaaag gagctaagct tctaaatgga    20820
tatagcatat tttgcataaa tcaaatttaa tatgaatcca tgattcttgt atgtgtaaat    20880
ctgcctgcat ttatttatgt cagtagttgg taattattca tcttaatttt ttttttttaaa   20940 tttctaggtg tgccaaagag gcggcacata aggattttaa aaaggcagtt ggtgcctttt    21000
ctgtaactta tgatccagaa aattatcagc ttgtcatttt ggtgagcatt tttgagttgt    21060
```

```
ttattttag tttaattcat ctggggcaat tgccttgata ataatgttgt taatttaaat   21120
catttagtcc atcaatgaag tcacctcaaa gcgagcacat atgctgattg acatgcactt   21180
tcggagtctg cgcactaagt tgtctctgat aatgagaaat gaagaagcta gtaagcagct   21240
ggaggtatgt cactttccct agcactgctt gtaagggtac ctaggaacga ttaactgtat   21300
cattccacaa cttgaatatg gggagcttgt catttatta  ctgcttctta acaattcctt   21360
aggttctata gttggaaaat tgtacaaagc ataatcatac taaagtttcc atgcctgagg   21420
tttcaaaatt aaacagcagc ttatgtatat taagggactt ctggtactt  cacttttact   21480 agaagtttat caaagttgct aataaaatgc ggcaatgctt cttccatata acatgttgtc   21540
attaaaaata ctagagaata tttaaatatc taatcatatt cctctcatta tgtatgttta   21600
tctttgttta aagggtata  gaacttcttc attctaattg gttgtcattc tttaaaactc   21660
ctgtcttcag attcccgcca gaggctattt ccctaactta ctattttgtc tcttaaggtg   21720
cattttatct acttttatta atcctccaat aattttcatc accatatatt tgttttcatt   21780
gataactatc aagtacgtcc atccattact atagaaacta agtggatctt agatgaatgt   21840
gccagctcta ctatattcct gtcaaattcc agagttcgtc atcattattc attagaagga   21900
aaacaccaca catttgaaat agtaaagaaa aaaggagtt  ccaaactgca ttttaggaga   21960 aaggtagtc  aagactgtgt tcttataaaa accctgtgaa atttgccacc tgtcaacttg   22020
atgtatgatg ctgaactctt agcagaaggg gaaaagttta atctccttt  gccactttgt   22080 tttttcttaa ggccatggag gtctgtttaa ttggtctttg ctctcattct ttcttgatgt   22140
ccctgtgttc atgattttgt ggttccttca gtgattctct cataactttt agcccagagc   22200
tgcctcctta ctttgattgt gagtattatg aaaatatact catatgcctc ttaaacatcg   22260
aattattctt aaatgatcta tcatactttt ggctaaccat ttatcagtga attatcaatg   22320
aaaaagaacg aaccagatta atgaaccagg actcaaaaaa catgacttct tgaaaagtcc   22380
tagaattatt ttatagattt tattactcta gtctaaaaaa aatgggtatt gcacttttaa   22440
attatttatg ctagttgtat tcattcattc aaattatcag gtctgttgaa caatgagaaa   22500
ctagtatgca tgcctatctt tcttcactac taatattaaa gagatttaca tgttcctata   22560
agaaattccc attttcaac  atgagccact aatacgtttg gttttcatta atggcatgct   22620
agaactgaac actaaatttt gataatggta tttaaagaca gtggttatcc acaagtttgg   22680
gatgtcagtg taacttagtt tcgtcatcac tggatattta caagtgctca tcataattgt   22740
ggatccagat cacaaggtct tacggactct ggtctcatgt tagctttcag atgcttacta   22800 agttttaat ttttgacatt ttttgattat tcagtttaac tactgtacca acaattttg    22860 attccttagg ttttgaggga ggtgtcattt taatgtcatt tcaacagagg aatgtttaga   22920
ccacagtacc taatgatgtt ataaaaaatg gcactgtttc cagaaaatat atactgatac   22980
cttttaataa aaatgaagcg aataaaattt tctataaaga tgatatttaa acatttttt    23040 acctaaataa gtaacattga gtttgtcaga ccgagtgagc tggtttttac tggggaacat   23100
ttgacctgct tcttagttat tatattgctg atgtcattgg ttaactaagg cagccttgtg   23160
ataagttttc agcagttacc ttggaaaatg tcaacaagtt ctttcctatt aacaaaaaca   23220
tataaaatgt catagacctt tagtaaccta aaaagtactt aggctgtgag aggtattttc   23280
taaaacctgt tagttttaac ctaaaactat taataattta tggaccccctc atatacaggg   23340 tcaagataat ttacatggct ggcctaaata cagttgtcgt aatagttgat aaagtgtatt   23400
```

```
catcagacgt ccatttctct tcagagttca aggcagcttg cctcgagatt tcatgaacag   23460
tttatcgtaa gagaagatct gatgggtcta gctattggta ctcatggtgc taatattcag   23520
caagctagaa aagtacctgg ggtcactgct attgatctag atgaagatac ctgcacattt   23580
catatttatg gagaggtaaa tattttactg catagttttt ttttccccaa acaagtattt   23640
cagctggcta atcttttgtc ttaaaatgtt tcccctttta ttaggatcag gatgcagtga   23700
aaaaagctag aagctttctc gaatttgctg aagatgtaat acaagttcca aggaacttag   23760
taggtaagtc agaagtatct gttgacatat agtacaacaa ctaagtttag gtaaacagtt   23820
tatttatagt gatagaattc cattttttct tactggaggg tatcatttaa ttgaaacata   23880
gtctttgaaa tatgatctgt tcttttttt tattatttaa gttttagggt acatgtgcac   23940
aatgtgcagg ttagttacat atgtatacac gtgacatgct ggtgcgctgc acccactaac   24000
ttgtcatcta gcattaggta tatctcccaa cgctatccct ccccctccc cccacccac   24060 aacagtcccc agagtgtgat gttccccttc ctgtgtccat gtgttctcat tgttcaatcg   24120
atctgttctt acagcataca aaaaaatatt tgttaagtat gatgctcaaa ggttacattt   24180
tcagaaggta ttcaaaagag attgcttttc tagttcaaac ctactaatac ctgaaaggat   24240
aaatcttgcc cagccctcct gactgtatac cttttatatc ttaaaattaa ataatttttc   24300
aaaatgaatg atatttgggg acttttatgat ttgaaataga tttgtatttg atctttctta   24360
tgggactata aaatgatagc attcatttta attatctcag ggttgaagat ctgaacatag   24420
gttacttaaa tctaaaaagt tccaaagcta aagaaaactt cagatgtctc tgggactttc   24480
tgcaaagtca atagtaattc ttcattttga cttgagtagt gttttatcac catcaccatc   24540
gtgagtatca gcaaatattt aggagctctt caccaatact cctaaatgct gcagatatct   24600
ttagtagaac atatcaaaac caggtgcagt tttatcaaga aagctacata tgtttttaat   24660
ttgtaaataa aattgggaca tactgcctat atgtttttta tctttaaaac ttgagatcat   24720
ggccatttta tataaagtaa tacatgttct ttggaaactt taaagaagaa agcaaggact   24780
tctcatacat tctgtttacg tagtttcaat gctaatttag cctgcttttt tgtcagcata   24840
gactcataaa catcttcctt gtcattaaca aacactagaa atgataaatg tatctcccaa   24900
agaaaattag cttgaagata aagtgcaaat agtaggaaaa taatgcagaa gtgttagctc   24960
aactgtgtac tacagacaac tggagaaatg tgtttgtaat gttactaagg taacttgcat   25020
accaattgta tgtgtacaga atgtatgcat agcgcaagat aaagtgctaa tctcaagaca   25080
gttgggtgat gaataatatt tatttttcttc tttacagctt gtcaagcaat tgcatacctt   25140
ttgtagttag aaaggttatt gtaaatttag gaattcttat ggaaaagag ctggtagttg   25200 ttttgttttt ttttttttaat agcaaatgag tagagaatta tgtgtcagat tcattaaagt   25260
tggttttgaa gatggcatga tggtagtggg gaaagtgctt gggcattgga gttggatctg   25320
gatttcagtc ctactttatt ctttggtggc aatgtgagcg tgggtcactg tcttagcccc   25380
cctgagaatt attttctta cctatcaaat gtgataatag gatccacctc atagagttga   25440
tgtgataatt aaattggaag atatagtagg ggacaattct ggacacagta ggggactctg   25500
ttcttcacct tattcaaaac aactccattt cagtagaaca gaatcacagt aaattgctct   25560
ttgggatttg gaaataagtg taatgtagaa ttggattatt tgctattaaa tattaaaagt   25620
agattctacc tgtggttacc tggaaagaag aggatctcag aaataaccag aaagactgct   25680
aaaagtaaat cagccttgtt tttgttttgt tgtttctagt tagtaaaatg agataattct   25740
gttttagaga tggtccactg caacactggg aacgttggaa cttttcagaa agcatttttg   25800
```

```
tgtaagattc tgcaaggcag atctttagag aggtgtcata atcagttttg catgtgtttt   25860
gtttgagtca accaacgtta tttgtgatct ctattttca caaactctct ttggtatgtg    25920
cactaattta tcttttcatt aaaattggat tcttcactca ctaagaatga attggtatga   25980
ctattcagtc agctatagtt aacacacagt acttaggata attaagatat tatcttaata   26040
aaaacatccc caaatctcat tttcattt gttaactcac ttagatcttt attaaagtca     26100
acattaattc atgaaaatgt aagtgttgca gtttaaaatc aaactgtgtg aagactccaa   26160
gtagcttctc tcacctcacc tttcccttt tcgttataga agaacagaaa taattgacag    26220
aaggacctag accaagaatc ctgatttaat ggtgtcagat ctgttctatg accagtcaaa   26280
gagtttctag gggtgaatga ggcagccaca cacagcaaga atgtcaaagc tatgctctga   26340
ttacaagagc cacaagaatt ttttgtgaga aggcttttca ctgagttctt atctagcatt   26400
ggctcaaagc aaattttgc ttccatcttt tcccccaact ttgccttgag ctttgccttt    26460
aaaggcgaaa aggaaaaaat ggaagatgag atggtgaggg caagcacatg gtggatgtgg   26520
ccaatgtaag ggtacttagg taccttgggt gagccctcag aatcagatgt agttcacatg   26580
tacatttcca gaattagtaa ttcttaagtt tgtaatgtct tgctttacca ctcgtgtcat   26640
gatgcaaatg aaagcagtca ttttccagta atgtatatga ttgtaaaata aataaggaaa   26700
tgatcaagta cctattttt actggtactt gaaatcccaa gttttaatag atgttactga    26760
aaaatactta aattggttta aagcttttc attgtggttt tgagttatct taaagtgggt    26820
tttcttaatc ttttactctg tgactaatcc cttcacttt taatacattg ctaaagtttg    26880
taagtaatgc acaggagtga tactctgtta acacattgac cttgaagaat ttgtattcct   26940
tttggatgta tgtatagctg cttaagccac tttcagactt agattatctt ttataaatgt   27000
gccttccata cagaattctg aaaatattta ccatggacaa agaagcagat ttaaatcagg   27060
tacagacaag aattgaaagt gttgaataag tgaatatatt tcccattctc tctactttt    27120 tcttaattct tatagaactt tgcagaaaga atgatacata ccacagtacc agcaagttta   27180
aagcgtaccc ttttgtgcaa aaataagagg ttatctttga actgccttaa aaatccaaaa   27240
ttaccctatc agtttgcaag tattaatcaa ctctggtacc tgaccaaagg agtttaaaca   27300
atgatgtcct aattaaacag aaaaccagat taaccatctt gttgaaaaga gtctctactt   27360
tggttttgaa atcttacaat tcaatacata cacatacaca taaaaatatc tatctatatg   27420
aatgtaatag tttacagtag ggctgtgctt actgctttga ggtatgtgtt tttaaaacca   27480
aacttgattt atttatttct taggcaaagt aataggaaaa aatggaaagc tgattcagga   27540
gattgtggac aagtcaggag ttgtgagggt gaggattgag gctgaaaatg agaaaaatgt   27600
tccacaagaa gaggtatgtt acagtgcgaa tattttgtgg cacatataat aaaagtaaaa   27660
gttttttatg tgatatgttg aggacctcta atatgtgcat aaagtgaatg caaatattct   27720
gattatcaag catgcctgct gtaattaatg ttataattgt agataatggc ccttctctgt   27780
cctctaatgc agtgagtttg gattagtcac tttattgaat tctttttcc tgatctttaa    27840 aatgggtagt tataaattt taaatatgag acatacatca ctgggtcgag tgttaatggc    27900
aatttaataa aataatatat atgtaaatgc ttcgtaaagc actttgtaaa tgttaatgtt   27960
gctgacaaaa gcaaaattgg aacacaggtt ttctggctttt catcttttca ctttttagt   28020 gtggggattg tgtagtatgt gtgttattc tgtgtgcttt aaatttattt ctgtgcttaa    28080
tatctcttcc ccatcctcct tacctttaaa ttctgtaacc cttttatctt cataaatata   28140
```

```
tgcttttttgt agcagctttt aaagtatttg catggggtag agaggtgagg atgcacctttt    28200 ctgtgcaata gtactcttaa gatactgtct catcaaagag ccgtaatttt cacatattgt    28260
ctagctttct ttttgaaaga ttcttttagc taaagttaaa tcttttttttt ctgcgtacaa    28320 tttgtattcg gtaattttat aaaccaaaac tgtttataat aacttacatt ttttaaaaat    28380
atgatgattg ataacactaa tagagctaaa taaagtctta aattggtcct ttttttctct    28440
tttgtgtttt ctgttttttta ccaaggaaat tatgccacca aattcccttc cttccaataa    28500
ttcaagggtt ggacctaatg ccccagaaga aaaaaaacat ttagatataa aggaaaacag    28560
cacccatttt tctcaaccta acagtacaaa agtccagagg gtaagaatta cttgtcactt    28620
tgaattacaa tacaagtaat ttgtctcaga tgtcacaatt ggtattttgg atgttttctc    28680
tggttagact tgtaggctac ttatgttcta ttttttttcc aaatgtaatt gccagcttat    28740
gagatactac aaattagtgt gatacatact tttcaattta ttcacagtaa caactcttat    28800
gccataaaca caaataatg gggttgcatt tagtggtcac attttttcttt tgacagtgga    28860 ctctcttttt tccatgcctt ctctctttaa attttgcagg tatcgtagct caaaatacac    28920
cttctgttag ttgcattagt tactactga accatatttt agaaactaat tttctctgtt    28980
tgaactaatc tgtttagaaa tgggtttaaa agtcctgcag tgaaagtcct gcgttcaggc    29040
ttctgtgtat cgtttgttat agttaatgac atcccttgca ttccttatac tgctttaggt    29100
gttagtggct tcatcagttg tagcagggga atcccagaaa cctgaactca aggcttggca    29160
ggtaggaaaa cattccttga gaaatacact ttcagtttat attttaatgt ttattcccct    29220
tgttaacaaa gattacaaat gatcctcagg attagggact ggagggagga gtgtttgtgg    29280
gtatgtggat ccattgccct ggagttaaag cttaaacacc ttcatgccgc ttgtaaggct    29340
tttcctaatt acttgtctag ttatcatctt taaattatct tctcccttgc actctagaga    29400
accttaagcc atactgaagt actttgagtt ctctgaacat tctcgtgctt attttgcttc    29460
tagacatatg tacaggttta ctctgcctgg aatgcttttt ctcctccaca tgtcacctca    29520
ttttgacctt attccttaca aagctttcct tgtgtacttg ccgaagatcc caccccctt    29580 gactggttca agagccttcc ccttctgttt tgcaatgtgc tcaccccctag catagcactt    29640 aaacatagat gtttatttgt tgatctcctc aaccacattg taagttcttt gagggcaggg    29700
agagctggtg agaactgttt atggaaaaaa atgttgtgga ctcatggatt aaaagcaaag    29760
gtgccatttt acaaagagga ctataacggc aagtggattg gatatgtctc attgccgggc    29820
agcccattat tccagaacac agagtaactt ttttctgggg tccgtactaa aggccatcat    29880
tccattcttg cctttcttca ttttaattta ctattcaggt ctactcgtga agtgcttaaa    29940
ttagagtggc ccttggggta ctccagcagt ttagacatgt tgcaagaaaa gatattcgta    30000
aataatttgc tccgaagtca atctaactaa atctgttaca taggatttta aagctatttt    30060
ggtgatattt gacccagagg gaagggtgta gcattcattc catcacatgg tattttggga    30120
aataatacag ttaaaggctt ttgtaacaaa taaagcttgt tggagaaaaa cccaacatgc    30180
agaaatgaat tgccagttat taatttgcac aattgtttct aggtttccct ataacttgtg    30240
acaagaagta gttgtttttt ttttccctct taatatatat atatatgggc taggagtaca    30300
gacatttagc atatgccttt taaaaatctg ttcttatgtt aagtagtgtc catagagaga    30360
agttcaaact ttccttgtga ttcagccttt taaaatttc agagtacatt attgaaatgt    30420
gtatgggctt gataaaactt aatgcttgtc aatgtaccta ttttttttgtc tcacagatta    30480 ttcagtgcat ttttatcctg atgttttttgt ttgtattttg tgtgtactct atttacttgg    30540
```

```
ttagcagaaa tgatttactt tttacttttg taccettggt atttcatttt gatttttttt    30600
ttaagaattt gatcggccag gcgcgatggc tcatgcctgt agtcccgaca ctttgggagg    30660
ccaaggcagg cagatcgcct gagcccagga attcgagacc agcctgggca atgtggcgaa    30720
accccgtctc tacagaaagt acaaaaattt agctgggtat gatggcatgc acgtgttgtc    30780
ccagctatcc aggaggctga ggtgggagga cacctaggg cctggggagg tcgaggctac    30840
agcgagccat tatcatgcca ctgcactcca gcctggataa cagaataaaa agaccctgtc    30900
tcaaaaaaaa aaaaaaaaaa agaggcggag gcgggcggat cacgaggtca ggagatcgag    30960
accatcccag ctaaaacagt gaaaccctgt ctctactaaa aaaacaaaac attagccggg    31020
cgtagtggcg ggtgcctgta gtcccagcta cttgggaggc tgaggcagga aatggcgtg    31080 aacccgggag gtggagcttg cagtgagccg agatcccgcc actgcactcc agcctgggcg    31140
acagagcgag actccgtctc aaaaaaaaaa aaaaaaaac aaaaagaaa aaaaaaaag    31200 aaaaattt gatcaggata aagcctttca taaatgaatt agagcatctt atactactca    31260
ttttgtttat acatctcatg gtaaagcttg tataatttg aattatacat ttgtgatttt    31320
tgctgatact gaatactagt ctttataata atctgatacg tttaaaaggt tgctattgat    31380
ctattcgtat tcacagtaga tgtgtaaagt agtatatcaa ctactttgt tttcatatat    31440 tgattatat ttacagcaaa catttgtata cctgctgttc accagatcct gtgctaggga    31500
attagtcgtt atttgcattt ttcagattaa tctatcatta cttttatagg atcattgttg    31560
caatttcttt ttcagggtat ggtaccattt gttttgtgg gaacaaagga cagcatcgct    31620
aatgccactg ttcttttgga ttatcacctg aactatttaa aggtgagaac agaaagaact    31680
ttaacttcta atcccttgt actaaaatat acaaacttta tagtagatct ttcagcagtt    31740
aggactcatt ctagcctgtg caaaacactg tatgacttgt caaaggtaat agagaaata    31800 cgttgtttgg cttataattt ttttaaaaat ggaagtcttt ataaatttaa gtaccaatat    31860
accagttttc aataaaattt tatacttccc tttattcttc tcttaaaccc ttacactcag    31920
tttaggcaat cctgtacata gcctgttaat ccattgatc cttctagca tttttggtttt    31980 ttccagacaa aaatctgtgt ctataactct tgcttatt gttccttta tgtcattat    32040 caaggaaatc taagcatttc atgaagttct ttgtttaaat gtttacccta tttttctctt    32100
tactgttatt caaaatacaa actatttgtg tcttctcata aatgttcagt ttagttagtg    32160
tgatgcggtt atgcctcctt aaaatttcaa actggaagat aggaacgagg aggctacaag    32220
gtgtagtgga gcaagcactg gatgggcaat gcagcaattt acttataaga cttcagcaaa    32280
tgaactagct gtgtgacttt aggcaagtca cttccctaca ctagatgctt cttgaaattc    32340
cttttggcca aaatgttcta tactttaatg aaatggaaac tgatctactt cattttcata    32400
atgttttatt tgtatccata catatcaaaa ttataatgta gctggtatta aatgttttta    32460
aaaagcattt caactctatt tatggcatta agaattttt tgctgatttc ttgaaagaaa    32520
taaaaagtac atgattctg cttgtgtgta aataagaatg aaaggaagaa aaagtgtaat    32580
actgggcatg ccattcattc ttatggtggc cagttaatta aaagtggaaa ggtttcatcc    32640
agcaaggttt acatgggtag gatacctctt tgattttttt ttaagtatgt ttatgtgtaa    32700
tctctctgtg tgtgtgtctc tctcgtaatt agcttaaatc atcatgaagg cctggagagt    32760
taggattgca ttgtatcaaa tcccttgttc ttttgactaa tgttcttct tagatccttt    32820 gatttattct caagaatatc ttctttggtt atcagcagct gccctgttgc cattctttcc    32880
```

```
atcaccagaa cttccctcgt ttgggcctgg catctctcac caaaaggtga ctgctttgcc   32940
ccagtgggat aacctggact actcttctgt tttgcaagat attcctattc catgagctat   33000
tactatacct ttgaggaag tcactcactc agctgcagtc tctcctttgc tcaaattcta    33060
tgtaaaacag attctggtgt aactatgtaa attgctaatg atggcagagc acagatgaaa   33120
cggaccaaat ccttacctga cctttctttt ccagaagctg ccacaaccaa gattttagaa   33180
acttagcttt acaggagctt ctccaatgac tgttcatgta gacagtctct atgataacct   33240
ctgcttcact gagacgccta ctactactat agttatgaat ctgattcccc gtagccagta   33300
aatgagatgt ttatgagtgg attggaagga cagtggttag aaatgaggtt tcatctggtt   33360
ttaacagaac ccaacatact ggaagtgctt tttgtaaggg tctgtcattg gaccccaggt   33420
gtatatttct atcaactaaa tgtatactgt ttctcgtact tgttgtagca gagttgtagt   33480
ctttaggaag ttttcaaggc atgatgtaag acctagctgt ctggtcagct attaaatagt   33540
tttgttttcc cctcatgagg aatagtcagc attttcagtt gatgaaaaaa tcattgttcc   33600
ttaaccatag tatatgttct tttaaaacaa aagatggccc aaactcaatg ctttgtaaat   33660
taagatatta actggcaaat ctatttaat caagattatt tacaatgtgt gatttttaag   33720
gttagctggt tataccttga atgtcattta tctatattca tacattttag catgtttat    33780
ttaatatcct atcatgaaga agtccccaaa atagcatatc tgtgccttag cagtagaata   33840
attggataat agtgccaaat tagacaactt taaattttat tcagtataat tttactgctg   33900
agtgttttg ttatatctct aattcttgac atcaataatc tgttatctgt agtaattttc     33960
tttttaagga gatcattcaa tttcctgata attctgtgta acagtgttta ctgtaaattt   34020
agaactgaaa ttgaaatatt ccagtatatt tttatctgat gaaaaggaga aggttttat    34080
taagtaaaat gtcaaattat ttttactgtt atcttgtata ttttaaatag gaagtagacc   34140
agttgcgttt ggagagatta caaattgatg agcagttgcg acagattgga gctagttcta   34200
gaccaccacc aaatcgtaca gataaggaaa aaagctatgt gactgatgat ggtcaaggaa   34260
tgggtcgagg tagtagacct tacagaaata gggggcacgg cagacgcggt cctggatata   34320
cttcaggtac aaaactaagca ttttactcag taactttatc tgttcctaga cttatagctg   34380
ctaatctcta atattcatta gaaccccatt ataacaattt gccgctacat ggtttccaat   34440
tcacagtggg ttaaattgtg ttacaggaga catagagtaa aaacctgatg ataaacacgt   34500
agagttcaca gggccggtgc aagttctgtt catgctctga ttggggtaa atctgcaaag    34560
cccttgtgtg ttgatgattt tcttaaggcc tctcctgatt ttataactgt atagtcaaaa   34620
ctttttcat ttgtgtactg tggctcattt ttattttgtc aggtatgtgc tggtcatact    34680
tgctggatgg actgtgtaaa tcaggggtct gcctcttgtg gctcataagg tgattttgag   34740
tgacatggcc aaagtcagcc ctaggcacag tcaagaagta ggcgaagttt ctctttgcct   34800
tcccagcttt tctgtccgtg cttctttctt ctctcccagt acctttcagt gaacctgatc   34860
cccacctgcc agtgcctact gtctttcttg ctcaacagtg tatctccttt gtaacttgct   34920
aatgatggta taaggtataa tccatttcac gcatatttgc atttcaaaaa ggaactcttt   34980
aagatggaaa agccttcaag atccacagga atgaagctat aatggtgaag ctataattgg   35040
tcattagctc caacagagga agagagaggt agtagagctg atattctgga gttggggaga   35100
gttacctact cctaaggcca accttgaacc taaccccctaa cccctctccc aacagtctgt   35160
tcttttact catgaatttc tgcctcaccg tggagctctt tttctccgct cctgtcctct    35220
aagtcgttaa ccccttcagg cataatgaat ttattatagt aattctttat taatgatcaa   35280
```

```
ttattgtaat gggagtggga gggcaggttg tggaccaaac atcaggcaag catgtatctg    35340
ccttcagcta gatccaatcc atgacccaca agagacccct ccctgaagca gttgccatgg    35400
tggcctcctt tgccaccctc tcagaaatga ccaaaatata tacattcccc tctgtcctgg    35460
gccaaatctt gctaaaagga gctctctttt tagaggtttt gtttatcagg gtatcacact    35520
taactgtcgt ggataatctt ttcctccaga gagtatagat gtttaaagga acacagctat    35580
ttaatgatat ggcacatcaa ggtttgaact taggtggcta ataacatacc ttttttaaaaa    35640 tgagaatgaa acatgtttat aaccaaaatt aacctcaaat attgcaaagc ccttcatttt    35700
gagtttaaaa ttttgtttta tgaaatggaa agtgataata ctctttgtgg gcttataaat    35760
tgggaagagt tttggattac ccctgaaacg tctctggaag cttctgttaa ccctcttttt    35820 tttttttta aagtcagaca atggtatata acttttaact ctcgatagga actaattctg    35880
aagcatcaaa tgcttctgaa acagaatctg accacagaga cgaactcagt gattggtcat    35940
tagctccaac agaggaagag agggagagct tcctgcgcag aggagacgga cggcggcgtg    36000 gaggggagg aagaggacaa ggaggaagag gacgtggagg aggcttcaaa ggtatggaga    36060
tcttcattaa gaaatcaaag tgaattgtaa cagctgtctt gaagttccat gagaaatcct    36120
attgatgcaa tgaactgtta ccaagatccc atctctcccg ttttgtgctg ataccatagg    36180
aaaggatcag ccttccactt gtgtagaaag aaagaatatt aggcagcctt ccttatggtt    36240
catacagata tatgaataaa tgctgataac taattcagca tcttggtggg tctaaacagc    36300
atcccttcat taactcacat tgacctgtag atgcagaatt ataataactg tgaaatattt    36360
tctgttactt agcagcaggc tagattatta gccattgtgt aactggaatc actggggtat    36420
tgattacatt tcagattctg tggttggttt aaatagaggg tgtgggaata aagaacttcc    36480
agtaagcatt tcagaatcag taactgttga acctttgaa aatattctca taggaaacga    36540
cgatcactcc cgaacagata atcgtccacg taatccaaga gaggctaaag gaagaacaac    36600
agatggatcc cttcaggtaa aacctgtctg cctcttttca tcttaattgt ttgaatatgg    36660
tagtttgaga tttatgagtt tattttactt tattaaaaac atgttcaaag attacaaatc    36720
cagtttatgt gaaatatttt accttcaaca ttacaattgt agtcaatctt agttctttgt    36780
gacaagtata caaataagag gatttctcta gagaatatgc agtctgagta tttgtgaaga    36840
ccttgacagc cacactatga ttttattatt tattatttat ttttattttt ttgagacggg    36900
agtttcgctt tgttgcccca ggctggagtg caatggcgca atctcggctc agagcaacct    36960
ctgcctcccg ggttcaagtg attctcctgc ctcagcctcc tgagtagctg gaattacagg    37020
catccactac catgcccagc taattttgt attttagta gagacggggt ttcaccatgt    37080
tggtcaggct ggtcttgaac tcccaacctc aggtgatctg cccaccttgg cctcccagtg    37140
tgctgggatt acaggcgtga gcactgtgcc cagccacact atgattttaa taccacattg    37200
gtagacctgc aatcccccag agaaggaaca tcctgggatg tacttagaga cctcagtaaa    37260
ccttatgtgt ctttgctccc ccaaattaac agggatagg tattctcttt gaatagaaaa    37320
taaggaaaag aaggtgtctg tcttacaact aataatcatg atagacagag ctgatgatat    37380
tcagctagtc tccatgcttg gtcagtcatc tgcttattta cagccaggac ctagtccgag    37440
gatctcttct caattggctg tcaccagtgc taaaccaatt gttaaataat tttaaaatta    37500
tctcctgagc acatccaggc acctttgcta agtgctttgt gtatgtttta tctcatttaa    37560
tcttacagca acccactgag gtagttttat tattccactt tataggtgag tgcactgtag    37620
```

```
cttcagtcct ttgcccacag tcacatagct agcatatgtc caaatgatag tcaaaccttta   37680 gtgtctgatt ctctgaatct atgttgtcgt ctactttttc tgtaactttt aattattaag   37740
tagttagggt tccttcctga ctatggattc atttgggacc atcacccaag attagtgaga   37800
gatacttttt aagacaaagt ttatgatgga atatttcttg gaattcatag cagctcaaag   37860
taagtgttaa ctattggtgg gttcttaagg accagcatgt ccaagggata gatagattgg   37920
taaattactg tatgtacctg tcttttacaa agctataaga tatttaagta cccgttttgt   37980
aattttccac ttaaactgat atgtttgatg aacttggcag tctaactgca ttggttaaaa   38040
ggatgcacat ttatatttct aaatgaaatg gaatactgaa tttaaaaggt gatgttttct   38100
ctattaagta tgaaaataga tacaaatctg gccaggcgcg gtgctcacgc ctgtagtccc   38160
agcgctttgg gaggccaagg tggtcagatc acctgaggtc aggagttcga ccagcctg    38220 gctaacatgg tgaaacccca tttctactaa aaatacaaaa aattagccag acgtgttggc   38280
gggcacctgt aatctcagct actcgggagg ctgaggcagg agaatcgctt gaacccaggt   38340
ggcagaggtt gcagtgagcc aagatcttgc cattgcactc cagcctgagc aacaagagca   38400
aaacaccatc tcaaaaaaaa aaaaaagg ccaggcacgg tggcgcacgc ctgtaatccc     38460
agcactttgg gaggccaagg cgggtggatc acaaggtcag gagatcgaga ccatcctggc   38520
taacatggtg aaaccccatc tctactaaaa atacaaaaaa ttagccgggc atggtggcgg   38580
gcacctatag tcccagctac tcaggaggct gaggcaggag gatggcgtga acctgggagg   38640
cggagcttgc agtgagccaa gatcgcgcca ctgcactcca gcctgggcga cagagcgaga   38700
ctgtctggga aaaaaaaaa aaagataca aatcaaagta ctgaatcctt ggtaacgaga     38760
catttaaaac acatgcacat acccactact taaacatact ttgaaattac aaccatttgg   38820
ggatgttttt agcatttgtg cttgaagtag atcaatattt gtagttgttt tagttccatt   38880
tgtcactgtt aactttcatt tgtacctctg gaattagcag tgctgtattc agcattggca   38940
cttaaaatat tttatagctc ttagaacact atttttttaaa ttacattgat ctttatactc  39000
tcctaggatt ccagtccttc cacaaattat tatatgcagt tttctttata ctgttccatt   39060
cttcagacag agttcaggtt gtaggatcat ctgaattttc ttagtgaaat acaagccagt   39120
agaaaccaaa gctcgtgttt ttctactgta tgactatggg agctctcagt atagagaaac   39180
ttgatcatac ctgtgataga tataaagatg taaattaaag tctagttagt gagttatttg   39240
agggtaaagc cagaatagga aaacattttg tttctctttt cctgggcttc acaatctttg   39300
gagaataact aatttttattt taactctagt gttagaggca tgtatgtctt ctggtaatca  39360
gtaatagtaa ttcattttac ctgtttgttt ctcactgttt tattctactt agaagaagac   39420
atgataggat tgtgagtttt tctctaactt tggatgcagt gagatgacca gtgtgttcca   39480
gttaaagaag aagagtgttt taaaatcata aaccaaataa agaatcctac cttacattaa   39540
tttcttgcac ttcttctgtt ctcatctcca tttctctttt taacatgtgg aatttacact   39600
tcaggtttaa atttcttgtc aggccaatta cagattacag taggatatgg tctgtgtata   39660
taacaactat aacttgtttt agatcagagt tgactgcaat aatgaaagga gtgtccacac   39720
taaaacatta cagaatacct ccagtgaagg tagtcggctg cgcacgggta agatcgtaa    39780 ccagaagaaa gagaagccag acagcgtgga tggtcagcaa ccactcgtga atggagtacc   39840
ctaaactgca taattctgaa gttatatttc ctataccatt tccgtaattc ttattccata   39900
ttagaaaact ttgttaggcc aaagacaaat agtaggcaag atggcacagg gcatgaaatg   39960
aacacaaatt atgctaagaa ttttttatttt tttggtattg gccataagca acaattttca  40020
```

```
gatttgcaca aaaagatacc ttaaaatttg aaacattgct tttaaaacta cttagcactt   40080
cagggcagat tttagttttattttctaaag tactgagcag tgatattctt tgttaatttg    40140
gaccattttc ctgcattggg tgatcattca ccagtacatt ctcagttttt cttaatatat   40200
agcatttatg gtaatcatat tagacttctg ttttcaatct cgtatagaag tcttcatgaa   40260
atgctatgtc atttcatgtc ctgtgtcagt ttatgttttg gtccacttttccagtatttt   40320
agtggaccct gaaatgtgtg tgatgtgaca tttgtcattt tcattagcaa aaaaagttgt   40380
atgatctgtg cctttttat atcttggcag gtaggaatat tatatttgga tgcagagttc    40440
agggaagata agttggaaac actaaatgtt aaagatgtag caaaccctgt caaacattag   40500
tactttatag aagaatgcat gctttccata ttttttcct tacataaaca tcaggttagg    40560
cagtataaag aataggactt gttttgtttt ttgttttgtt gcactgaagt ttgataaata   40620
gtgttattga gagagatgtg taattttttct gtatagacag gagaagaaag aactatcttc  40680
atctgagaga ggctaaaatg ttttcagcta ggaacaaatc ttcctggtcg aaagttagta   40740
ggatatgcct gctctttggc ctgatgacca attttaactt agagcttttt tttttaatt    40800
ttgtctgccc caagttttgt gaaatttttc atatttaat ttcaagctta ttttggagag    40860
ataggaaggt catttccatg tatgcataat aatcctgcaa agtacaggta ctttgtctaa   40920
gaaacattgg aagcaggtta aatgttttgt aaactttgaa atatatggtc taatgtttaa   40980
gcagaattgg aaaagactaa gatcggttaa caaataacaa cttttttttc ttttttctt   41040
ttgtttttttg aagtgttggg gtttggtttt gttttttgag tctttttttt ttaagtgaaa  41100
tttattgagg aaaaatatgt gaaggacctt cactctaaga tgttatattt ttcttaaaaa   41160
gtaactccta gtagggtac cactgaatct gtacagagcc gtaaaaactg aagttctgcc    41220
tctgatgtat tttgtgagtt tgtttctttg aattttcatt ttacagttac ttttccttgc   41280
atacaaacaa gcatataaaa tggcaacaaa ctgcacatga tttcacaaat attaaaaagt   41340
cttttaaaaa gtattgccaa acattaatgt tgatttctag ttatttattc tgggaatgta   41400
tagtattga aaacagaaat tggtaccttg cacacatcat ctgtaagctg tttggttttta   41460
aaatactgta gataattaac caaggtagaa tgaccttgta atgtaactgc tcttgggcaa   41520
tattctctgt acatattagc gacaacagat tggattttat gttgacattt gtttggttat   41580
agtgcaatat attttgtatg caagcagttt caataaagtt tgatcttcct ctgctaaatt   41640
gatgttgatg caatccttac aaatgattgc ttttaaaatt ttaagctagg aaaagaaatc   41700
tatagaaagt gttctgttac aaaatgtaac tgttaccatt ggaaatttca cgtcatagga   41760
agttagcctt tatctaccaa ctttcaagaa cttgtttaat aaagcgaaaa actcaaccaa   41820
atggtacaaa accacagtgt accattaaaa tatgcactaa gtctcttttt tacaaaggct   41880
gtattcagca aggcgctaac ttgcttaaat gtgaattact aacttctaaa actgtacttt   41940
gattcacatg ttttcaaatg gagttggagt tcattcatat tacaatatt gtgtgctaaa    42000
cgtgtatgtt tttcagttca aagtcatgat gttttttaaaa tcttattaaa gtttcaaaaa  42060
tctgaagatt gtttatctag atgtaaattt ttattaaaaa gttgcactta tgaaaaagca   42120
aaaaattagt ctgacagatg tttgctcctg gttttaaatt tctacatttg acaaaaacta   42180
atgatatgtg gggggaaagt tgtgcaaagt aaatgtatgt tgcaaataat cttttatgag   42240
cccttaaaag gcaaaacga agacacttga aaataattct ccatattccc agacataaaa   42300
tttcaacaca tttattacat agggtgccac taaaccatat taaacatata ctcctatttg   42360
```

-continued

```
tgcacacatg aacataccct gccctttgga aaaaagtatg tctatgaagt aaaaaaaaaa  42420
aattgattta aacgtctcag taataaaata aatgagaggt ttgtaggtag aatgtgcctg  42480
ggaattgact actgtaatca cttcaaggaa ctctggcaca gcctacccgc ctaaaaggta  42540
caaatggaga ggtgacagtg tcagtgttct acccagggtt agaatccaaa atgatgctag  42600
acagcctcct ctgcattgat gagttttttt ccccagaaaa ataactattt tctgcttttc  42660

ттgттттттca ttctgatgct tttgtggttc tttgctaccc attctgtcta actgggcatc  42720
attagtggtg ggtaggctga aaccatactc aagtaacttg tttggatttt ccttgtttca  42780
cagtagtttt cagcactaca catgaacagc ctgttggagg cagccagctt aacactcaac  42840

ttggctctct cagagccatc tctctcatct gatgatggtc ttagaattcc tggtggctcg  42900
gaatatacgt cttttagagg cagcaaaatg attctgaccc ttttgagcca gtttcagttt  42960
catggccata aacagccttg tgaacctcta tgcctctgat aaccagttat tctgaaatag  43020

tcattaccat gtgctagtct tgattgttca taaggcttaa tgtaccagaa tttaaatctt  43080
gagcatcttg ttttctctgt tatctgagg  tcatttaaaa agttttattt catttctct  43140 ctatgtacca taatgaaact gggaaaatcc attttatttt aatttttttt agtatactaa  43200
ggggttttct gttagtgaga gaggcttgct ctgtgttaaa ctcacaggga agaattatcc  43260

ttcccctgga atacagaccc agggtgcagc tagcagtgct ctggcctttg catgagagaa  43320

taatatccat gtgtctcttc ctgacctttt gctgacaagt ttccctcatt aaaaccactt  43380

tcttctgtgt ggctttgtgc agtttgccat aacccattac ctcaaaaatg gtgcccaaca  43440

tgaggtaaaa tccgcttatt tcacctctgg ctttttggaa actgcaaaag ggatcaacta  43500
agctatacta gggatggaca gcatccctgc tggggctggt gatgggaaac ccagccaagc  43560

taacatctgc aaagcatgct agtgtggtgc ttattggtgt tcatgtgcca cagaggtcct  43620
gggaagtttg tgtaagggag attgagacaa ttaaatcctt tggcactcca agtctggcag  43680
cctctgtgag acctaaggaa aaagaagttg ggagaaaacc ctcagcacct aagtgccatt  43740
agaatagttg atgcagtcta aacgtttttt tgtttgtttt ggtttttttt tttttttgag  43800
acagggtctc tgtcacccag gctggagtgc agtggcatga tctcagctca ctgtggcctc  43860
cgcctcccag gttcaagcga ttcctgtgcc tcagcctccc tagtagctgg gactacaggc  43920
acctgtcacc atgcccaact aaттттттgтa ттттттттgтa gagatgcagt ttcgccatgt  43980

tggccaggct ggtcttaaac tcctaacctc aggtgatctg tctgccttgg cctcccaaag  44040

tgctgggatt acaggcctga ccactgcac acagccacaa cttttagatt tgagacttgt  44100
cattgtgcag tgtgccaccc aggggccttt ggtaggaatt gaggtatatc ctgtgggatt  44160

tcaaagacac taacagggaa ttggactccc agcaatggtc acaagagtaa cctgaggctt  44220

taattgttta tatgatgacg aggctacacc tacaaagtag tgaagctgaa tggcaagcac  44280

tttgggttta tcacgggatt tcttctgcc agatgaattt gctaggctga ccaatgggga  44340
gggagcaaat ggacctgcct tgttcttgaa ttggatgttc agggcaatca gattcacata  44400
accaccaaga ggagacttcc tgagaaactg agtgccaagt gaaccattct actgaggtta  44460
aagctgtttt gagacaactt ggcattttt catacttgca tgaaaatcct aggcatctag  44520
gataagtagt aaccaaatga ccttaattca gagaatgctg gaaaagttga tggtttctta  44580

tacggagaca tccctaactt tgctccttct gccagagtgt aaaggatgaa ataatccttt  44640
ggagctgata tatgccccac ccaaagtggg ggtaatgaga taaggggccc tggaaagaat  44700
atgtctcagc aaaaatgaaa agtcaaggga agagcatcaa ctctagactt ttcctaggct  44760
```

```
tgcacaggca gtacatcatg actcttggtc tgcaacaaag tgatgactag ctaaggagat    44820
agataggaaa ggtagaatca ctctaaggag cttgcagaga gaaggatgca ggaaacaaca    44880
ctgatattag agtaggcatt aagaaccccc ctatggagag ctgatgcaag gaggttctgg    44940
atgggagggt tccctttgga gatggaggca gttagctttc cccactgctt ggccagcaaa    45000
```

<210> SEQ ID NO 2
<211> LENGTH: 23
<212> TYPE: DNA
<213> ORGANISM: Artificial sequence
<220> FEATURE:
<223> OTHER INFORMATION: Primer

<400> SEQUENCE: 2

```
catgaagatt caataacagt tgc                                             23
```

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3

```
cactttagct aaccaccaac a                                               21
```

<210> SEQ ID NO 4
<211> LENGTH: 6328
<212> TYPE: DNA
<213> ORGANISM: Artificial sequence
<220> FEATURE:
<223> OTHER INFORMATION: Plasmid

<400> SEQUENCE: 4

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattcgtt    960
aacagatctg ctcagctccg tttcggtttc acttccggtg gagggccgcc tctgagcggg   1020
cggcgggccg acggcgagcg cgggcggcgg cggtgacgga ggcgccgctg ccaggggcg   1080
```

| | |
|---|---:|
| tgcggcagcg cggcggcggc ggcggcggcg gcggaggcgg cggcggcggc ggcggcggcg | 1140 |
| gcggcggcgg cggcggcggc ggcggctggg cctcgagcgc ccgcagccca cctctcgggg | 1200 |
| gcgggctccc ggcgctagca gggctgaaga gaagatggag gagctggtgg tggaagtgcg | 1260 |
| gggctccaat ggcgctttct acaaggcatt tgaaagcggc cgcggggtct tcacactcga | 1320 |
| agatttcgtt ggggactggc gacagacagc cggctacaac ctggaccaag tccttgaaca | 1380 |
| gggaggtgtg tccagtttgt ttcagaatct cggggtgtcc gtaactccga tccaaaggat | 1440 |
| tgtcctgagc ggtgaaaatg ggctgaagat cgacatccat gtcatcatcc cgtatgaagg | 1500 |
| tctgagcggc gaccaaatgg gccagatcga aaaaattttt aaggtggtgt accctgtgga | 1560 |
| tgatcatcac tttaaggtga tcctgcacta tggcacactg gtaatcgacg gggttacgcc | 1620 |
| gaacatgatc gactatttcg gacggccgta tgaaggcatc gccgtgttcg acggcaaaaa | 1680 |
| gatcactgta acagggaccc tgtggaacgg caacaaaatt atcgacgagc gcctgatcaa | 1740 |
| ccccgacggc tccctgctgt tccgagtaac catcaacgga gtgaccggct ggcggctgtg | 1800 |
| cgaacgcatt ctggcggact acaaagacga tgacggtgat tataaagatc atgacatcga | 1860 |
| ttacaaggat gacgatgaca gcgatcgta atctagaggc ccgtttaaac ccgctgatca | 1920 |
| gcctcgactg tgccttctag ttgccagcca tctgttgttt gccctccccc gtgccttcc | 1980 |
| ttgaccctgg aagtgccac tcccactgtc ctttcctaat aaaatgagga aattgcatcg | 2040 |
| cattgtctga gtaggtgtca ttctattctg ggggtgggg tggggcagga cagcaagggg | 2100 |
| gaggattggg aagacaatag caggcatgct ggggatgcgg tgggctctat ggcttctgag | 2160 |
| gcggaaagaa ccagctgggg ctctaggggg tatccccacg cgccctgtag cggcgcatta | 2220 |
| agcgcggcgg gtgtggtggt tacgcgcagc gtgaccgcta cacttgccag cgccctagcg | 2280 |
| cccgctcctt tcgctttctt cccttccttt ctcgccacgt tcgccggctt tccccgtcaa | 2340 |
| gctctaaatc gggggctccc tttagggttc cgatttagtg ctttacggca cctcgacccc | 2400 |
| aaaaaacttg attagggtga tggttcacgt agtgggccat cgccctgata gacggttttt | 2460 |
| cgccctttga cgttggagtc acgttctttt aatagtggac tcttgttcca aactggaaca | 2520 |
| acactcaacc ctatctcggt ctattctttt gatttataag gattttgcc gatttcggcc | 2580 |
| tattggttaa aaatgagct gatttaacaa aaatttaacg cgaattaatt ctgtggaatg | 2640 |
| tgtgtcagtt agggtgtgga agtccccag gctcccagc aggcagaagt atgcaaagca | 2700 |
| tgcatctcaa ttagtcagca accaggtgtg gaaagtcccc aggctcccca gcaggcagaa | 2760 |
| gtatgcaaag catgcatctc aattagtcag caaccatagt cccgccccta actccgccca | 2820 |
| tcccgcccct aactccgccc agttccgccc attctccgcc ccatggctga ctaattttt | 2880 |
| ttatttatgc agaggccgag gccgcctctg cctctgagct attccagaag tagtgaggag | 2940 |
| gcttttttgg aggcctaggc ttttgcaaaa agctcccggg agcttgtata tccatttcg | 3000 |
| gatctgatca agagacagga tgaggatcgt ttcgcatgat tgaacaagat ggattgcacg | 3060 |
| caggttctcc ggccgcttgg gtggagaggc tattcggcta tgactgggca acagacaa | 3120 |
| tcggctgctc tgatgccgcc gtgttccggc tgtcagcgca ggggcgcccg gttcttttg | 3180 |
| tcaagaccga cctgtccggt gccctgaatg aactgcagga cgaggcagcg cggctatcgt | 3240 |
| ggctggccac gacgggcgtt ccttgcgcag ctgtgctcga cgttgtcact gaagcgggaa | 3300 |
| gggactggct gctattgggc gaagtgccgg gcaggatct cctgtcatct caccttgctc | 3360 |
| ctgccgagaa agtatccatc atggctgatg caatgcggcg gctgcatacg cttgatccgg | 3420 |
| ctacctgccc attcgaccac caagcgaaac atcgcatcga gcgagcacgt actcggatgg | 3480 |

```
aagccggtct tgtcgatcag gatgatctgg acgaagagca tcagggggctc gcgccagccg    3540
aactgttcgc caggctcaag gcgcgcatgc ccgacggcga ggatctcgtc gtgacccatg    3600
gcgatgcctg cttgccgaat atcatggtgg aaaatggccg cttttctgga ttcatcgact    3660
gtggccggct gggtgtggcg gaccgctatc aggacatagc gttggctacc cgtgatattg    3720
ctgaagagct tggcggcgaa tgggctgacc gcttcctcgt gctttacggt atcgccgctc    3780
ccgattcgca gcgcatcgcc ttctatcgcc ttcttgacga gttcttctga gcgggactct    3840
ggggttcgaa atgaccgacc aagcgacgcc caacctgcca tcacgagatt tcgattccac    3900
cgccgccttc tatgaaaggt tgggcttcgg aatcgttttc cgggacgccg gctggatgat    3960
cctccagcgc ggggatctca tgctggagtt cttcgcccac cccaacttgt ttattgcagc    4020
ttataatggt tacaaataaa gcaatagcat cacaaatttc acaaataaag catttttttc    4080
actgcattct agttgtggtt tgtccaaact catcaatgta tcttatcatg tctgtatacc    4140
gtcgacctct agctagagct tggcgtaatc atggtcatag ctgtttcctg tgtgaaattg    4200
ttatccgctc acaattccac acaacatacg agccggaagc ataaagtgta aagcctgggg    4260
tgcctaatga gtgagctaac tcacattaat tgcgttgcgc tcactgcccg ctttccagtc    4320
gggaaacctg tcgtgccagc tgcattaatg aatcggccaa cgcgcgggga gaggcggttt    4380
gcgtattggg cgctcttccg cttcctcgct cactgactcg ctgcgctcgg tcgttcggct    4440
gcggcgagcg gtatcagctc actcaaaggc ggtaatacgg ttatccacag aatcagggga    4500
taacgcagga aagaacatgt gagcaaaagg ccagcaaaag gccaggaacc gtaaaaaggc    4560
cgcgttgctg gcgttttttcc ataggctccg ccccctgac gagcatcaca aaaatcgacg    4620
ctcaagtcag aggtggcgaa acccgacagg actataaaga taccaggcgt ttccccctgg    4680
aagctccctc gtgcgctctc ctgttccgac cctgccgctt accggatacc tgtccgcctt    4740
tctcccttcg ggaagcgtgg cgctttctca tagctcacgc tgtaggtatc tcagttcggt    4800
gtaggtcgtt cgctccaagc tgggctgtgt gcacgaaccc cccgttcagc ccgaccgctg    4860
cgccttatcc ggtaactatc gtcttgagtc caacccggta agacacgact tatcgccact    4920
ggcagcagcc actggtaaca ggattagcag agcgaggtat gtaggcggtg ctacagagtt    4980
cttgaagtgg tggcctaact acggctacac tagaagaaca gtatttggta tctgcgctct    5040
gctgaagcca gttaccttcg gaaaaagagt tggtagctct tgatccggca acaaaccac    5100
cgctggtagc ggtttttttg tttgcaagca gcagattacg cgcagaaaaa aaggatctca    5160
agaagatcct ttgatctttt ctacggggtc tgacgctcag tggaacgaaa actcacgtta    5220
agggattttg gtcatgagat tatcaaaaag gatcttcacc tagatccttt taaattaaaa    5280
atgaagtttt aaatcaatct aaagtatata tgagtaaact tggtctgaca gttaccaatg    5340
cttaatcagt gaggcaccta tctcagcgat ctgtctattt cgttcatcca tagttgcctg    5400
actccccgtc gtgtagataa ctacgatacg ggagggctta ccatctggcc ccagtgctgc    5460
aatgataccg cgagacccac gctcaccggc tccagattta tcagcaataa accagccagc    5520
cggaagggcc gagcgcagaa gtggtcctgc aactttatcc gcctccatcc agtctattaa    5580
ttgttgccgg gaagctagag taagtagttc gccagttaat agtttgcgca acgttgttgc    5640
cattgctaca ggcatcgtgg tgtcacgctc gtcgtttggt atggcttcat tcagctccgg    5700
ttcccaacga tcaaggcgag ttacatgatc ccccatgttg tgcaaaaaag cggttagctc    5760
cttcggtcct ccgatcgttg tcagaagtaa gttggccgca gtgttatcac tcatggttat    5820
```

```
ggcagcactg cataattctc ttactgtcat gccatccgta agatgctttt ctgtgactgg    5880
tgagtactca accaagtcat tctgagaata gtgtatgcgg cgaccgagtt gctcttgccc    5940
ggcgtcaata cgggataata ccgcgccaca tagcagaact ttaaaagtgc tcatcattgg    6000
aaaacgttct cgggggcgaa aactctcaag gatcttaccg ctgttgagat ccagttcgat    6060
gtaacccact cgtgcaccca actgatcttc agcatctttt actttcacca gcgtttctgg    6120
gtgagcaaaa acaggaaggc aaaatgccgc aaaaaaggga ataagggcga cacggaaatg    6180
ttgaatactc atactcttcc tttttcaata ttattgaagc atttatcagg gttattgtct    6240
catgagcgga tacatatttg aatgtattta gaaaaataaa caaataggggg ttccgcgcac    6300 atttccccga aaagtgccac ctgacgtc                                        6328
```

<210> SEQ ID NO 5
<211> LENGTH: 6523
<212> TYPE: DNA
<213> ORGANISM: Artificial sequence
<220> FEATURE:
<223> OTHER INFORMATION: Plasmid

<400> SEQUENCE: 5

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattcgtt     960
aacagatctg ctcagctccg tttcggtttc acttccggtg agggccgcc tctgagcggg    1020 cggcgggccg acggcgagcg cgggcggcgg cggtgacgga ggcgccgctg ccaggggggcg    1080 tgcggcagcg cggcgcggc ggcggcggc gcggaggcgg cggcggcggc ggcggcggcg    1140
gcggcggcgc cggcggcggc ggcggcggcg gcggcggcg cggcggcggc ggcggcggcg    1200
gcggcggcgg cggcggcggc ggcggcggcg gcggcggcgg cggcggcggc ggcggcggcg    1260
gcggcggcgg cggcggcggc ggcggcggcg gcggcggcgg cggcggcggc ggcggcggcg    1320
gcggcggcgg cggcggcggc ggcggcggcg gcggcggcgg ctgggcctcg agcgcccgca    1380
gcccacctct cggggggcggg ctcccggcgc tagcagggct gaagagaaga tggaggagct    1440
ggtggtggaa gtgcggggct ccaatggcgc tttctacaag gcatttgaaa gcggccgcgg    1500
ggtcttcaca ctcgaagatt tcgttgggga ctggcgacag acagccggct acaacctgga    1560
```

```
ccaagtcctt gaacagggag gtgtgtccag tttgtttcag aatctcgggg tgtccgtaac   1620
tccgatccaa aggattgtcc tgagcggtga aaatgggctg aagatcgaca tccatgtcat   1680
catcccgtat gaaggtctga gcggcgacca aatgggccag atcgaaaaaa ttttttaaggt  1740 ggtgtaccct gtggatgatc atcactttaa ggtgatcctg cactatggca cactggtaat   1800
cgacggggtt acgccgaaca tgatcgacta tttcggacgg ccgtatgaag gcatcgccgt   1860
gttcgacggc aaaaagatca ctgtaacagg gaccctgtgg aacggcaaca aaattatcga   1920
cgagcgcctg atcaaccccg acggctccct gctgttccga gtaaccatca acggagtgac   1980
cggctggcgg ctgtgcgaac gcattctggc ggactacaaa gacgatgacg gtgattataa   2040
agatcatgac atcgattaca aggatgacga tgacaagcga tcgtaatcta gaggcccgtt   2100
taaacccgct gatcagcctc gactgtgcct tctagttgcc agccatctgt tgtttgcccc   2160
tcccccgtgc cttccttgac cctggaaggt gccactccca ctgtcctttc ctaataaaat   2220
gaggaaattg catcgcattg tctgagtagg tgtcattcta ttctgggggg tggggtgggg   2280
caggacagca agggggagga ttgggaagac aatagcaggc atgctgggga tgcggtgggc   2340
tctatggctt ctgaggcgga agaaccagct ggggctcta gggggtatcc ccacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg ttttttcgcc ctttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
taattctgtg gaatgtgtgt cagttagggt gtggaaagtc ccaggctcc ccagcaggca    2880 gaagtatgca aagcatgcat ctcaattagt cagcaaccag gtgtggaaag tccccaggct   2940
ccccagcagg cagaagtatg caaagcatgc atctcaatta gtcagcaacc atagtcccgc   3000
ccctaactcc gcccatcccg cccctaactc cgcccagttc cgcccattct ccgccccatg   3060
gctgactaat ttttttttatt tatgcagagg ccgaggccgc ctctgcctct gagctattcc   3120
agaagtagtg aggaggcttt tttggaggcc taggcttttg caaaaagctc ccgggagctt   3180
gtatatccat tttcggatct gatcaagaga caggatgagg atcgtttcgc atgattgaac   3240
aagatggatt gcacgcaggt tctccggccg cttgggtgga gaggctattc ggctatgact   3300
gggcacaaca gacaatcggc tgctctgatg ccgccgtgtt ccggctgtca gcgcaggggc   3360
gcccggttct ttttgtcaag accgacctgt ccggtgccct gaatgaactg caggacgagg   3420
cagcgcggct atcgtggctg gccacgacgg gcgttccttg cgcagctgtg ctcgacgttg   3480
tcactgaagc gggaagggac tggctgctat tgggcgaagt gccggggcag gatctcctgt   3540
catctcacct tgctcctgcc gagaaagtat ccatcatggc tgatgcaatg cggcggctgc   3600
atacgcttga tccggctacc tgcccattcg accaccaagc gaaacatcgc atcgagcgag   3660
cacgtactcg gatggaagcc ggtcttgtcg atcaggatga tctggacgaa gagcatcagg   3720
ggctcgcgcc agccgaactg ttcgccaggc tcaaggcgcg catgcccgac ggcgaggatc   3780
tcgtcgtgac ccatggcgat gcctgcttgc cgaatatcat ggtggaaaat ggccgctttt   3840
ctggattcat cgactgtggc cggctgggtg tggcggaccg ctatcaggac atagcgttgg   3900
```

```
ctacccgtga tattgctgaa gagcttggcg gcgaatgggc tgaccgcttc ctcgtgcttt    3960
acggtatcgc cgctcccgat tcgcagcgca tcgccttcta tcgccttctt gacgagttct    4020
tctgagcggg actctggggt tcgaaatgac cgaccaagcg acgcccaacc tgccatcacg    4080
agatttcgat tccaccgccg ccttctatga aggttgggc ttcggaatcg ttttccggga     4140
cgccggctgg atgatcctcc agcgcgggga tctcatgctg gagttcttcg cccacccaa    4200
cttgtttatt gcagcttata atggttacaa ataaagcaat agcatcacaa atttcacaaa    4260
taaagcattt ttttcactgc attctagttg tggtttgtcc aaactcatca atgtatctta    4320
tcatgtctgt ataccgtcga cctctagcta gagcttggcg taatcatggt catagctgtt    4380
tcctgtgtga aattgttatc cgctcacaat tccacacaac atacgagccg aagcataaa     4440
gtgtaaagcc tggggtgcct aatgagtgag ctaactcaca ttaattgcgt tgcgctcact    4500
gcccgctttc cagtcgggaa acctgtcgtg ccagctgcat taatgaatcg gccaacgcgc    4560
ggggagaggc ggtttgcgta ttgggcgctc ttccgcttcc tcgctcactg actcgctgcg    4620
ctcggtcgtt cggctgcggc gagcggtatc agctcactca aaggcggtaa tacgttatc    4680
cacagaatca ggggataacg caggaaagaa catgtgagca aaaggccagc aaaaggccag    4740
gaaccgtaaa aaggccgcgt tgctggcgtt tttccatagg ctccgccccc ctgacgagca    4800
tcacaaaaat cgacgctcaa gtcagaggtg gcgaaacccg acaggactat aaagatacca    4860
ggcgtttccc cctggaagct ccctcgtgcg ctctcctgtt ccgaccctgc cgcttaccgg    4920
atacctgtcc gcctttctcc cttcgggaag cgtggcgctt tctcatagct cacgctgtag    4980
gtatctcagt tcggtgtagg tcgttcgctc caagctgggc tgtgtgcacg aaccccccgt    5040
tcagcccgac cgctgcgcct tatccggtaa ctatcgtctt gagtccaacc cggtaagaca    5100
cgacttatcg ccactggcag cagccactgg taacaggatt agcagagcga ggtatgtagg    5160
cggtgctaca gagttcttga agtggtggcc taactacggc tacactagaa gaacagtatt    5220
tggtatctgc gctctgctga agccagttac cttcggaaaa agagttggta gctcttgatc    5280
cggcaaacaa accaccgctg gtagcggttt ttttgtttgc aagcagcaga ttacgcgcag    5340
aaaaaaagga tctcaagaag atcctttgat cttttctacg gggtctgacg ctcagtggaa    5400
cgaaaactca cgttaaggga ttttggtcat gagattatca aaaaggatct tcacctagat    5460
ccttttaaat taaaaatgaa gttttaaatc aatctaaagt atatatgagt aaacttggtc    5520
tgacagttac caatgcttaa tcagtgaggc acctatctca gcgatctgtc tatttcgttc    5580
atccatagtt gcctgactcc ccgtcgtgta gataactacg atacgggagg gcttaccatc    5640
tggccccagt gctgcaatga taccgcgaga cccacgctca ccggctccag atttatcagc    5700
aataaaccag ccagccggaa gggccgagcg cagaagtggt cctgcaactt tatccgcctc    5760
catccagtct attaattgtt gccgggaagc tagagtaagt agttcgccag ttaatagttt    5820
gcgcaacgtt gttgccattg ctacaggcat cgtggtgtca cgctcgtcgt ttggtatggc    5880
ttcattcagc tccggttccc aacgatcaag gcgagttaca tgatccccca tgttgtgcaa    5940
aaaagcggtt agctccttcg gtcctccgat cgttgtcaga agtaagttgg ccgcagtgtt    6000
atcactcatg gttatggcag cactgcataa ttctcttact gtcatgccat ccgtaagatg    6060
cttttctgtg actggtgagt actcaaccaa gtcattctga atagtgtata gcggcgacc     6120
gagttgctct tgcccggcgt caatacggga taataccgcg ccacatagca gaactttaaa    6180
agtgctcatc attggaaaac gttcttcggg gcgaaaactc tcaaggatct taccgctgtt    6240
gagatccagt tcgatgtaac ccactcgtgc acccaactga tcttcagcat cttttacttt    6300
```

```
caccagcgtt tctgggtgag caaaaacagg aaggcaaaat gccgcaaaaa agggaataag    6360
ggcgacacgg aaatgttgaa tactcatact cttccttttt caatattatt gaagcattta    6420
tcagggttat tgtctcatga gcggatacat atttgaatgt atttagaaaa ataaacaaat    6480
aggggttccg cgcacatttc cccgaaaagt gccacctgac gtc                      6523
```

<210> SEQ ID NO 6
<211> LENGTH: 6263
<212> TYPE: DNA
<213> ORGANISM: Artificial sequence
<220> FEATURE:
<223> OTHER INFORMATION: Plasmid

<400> SEQUENCE: 6

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattcgtt    960
aacagatctg ctcagctccg tttcggtttc acttccggtg gagggccgcc tctgagcggg   1020
cggcgggccg acggcgagcg cgggcggcgg cggtgacgga ggcgccgctg ccaggggggcg   1080 tgcggcagcg cggcggcggc ggcggcggcg gcggaggcgg cggcggcggc ggcggcggcg   1140 gcggcggcg cggcggcggc ggcggctggg cctcgaggat atcaagatct ggcctcggcg   1200
gccaagcttg gcaatccggt actgttggta aagccaccgg ggtcttcaca ctcgaagatt   1260
tcgttgggga ctggcgacag acagccggct acaacctgga ccaagtcctt gaacaggag   1320 gtgtgtccag tttgtttcag aatctcgggg tgtccgtaac tccgatccaa aggattgtcc   1380
tgagcggtga aaatgggctg aagatcgaca tccatgtcat catcccgtat gaaggtctga   1440
gcggcgacca aatgggccag atcgaaaaaa tttttaaggt ggtgtaccct gtggatgatc   1500
atcactttaa ggtgatcctg cactatggca cactggtaat cgacgggggtt acgccgaaca   1560 tgatcgacta tttcggacgg ccgtatgaag gcatcgccgt gttcgacggc aaaaagatca   1620
ctgtaacagg gaccctgtgg aacggcaaca aaattatcga cgagcgcctg atcaaccccg   1680
acggctccct gctgttccga gtaaccatca acggagtgac cggctggcgg ctgtgcgaac   1740
gcattctggc ggactacaaa gaccatgacg gtgattataa agatcatgac atcgattaca   1800
```

```
aggatgacga tgacaagcga tcgtaatcta gaggcccgtt taaacccgct gatcagcctc    1860
gactgtgcct tctagttgcc agccatctgt tgtttgcccc tcccccgtgc cttccttgac    1920
cctggaaggt gccactccca ctgtcctttc ctaataaaat gaggaaattg catcgcattg    1980
tctgagtagg tgtcattcta ttctgggggg tggggtgggg caggacagca aggggaggga    2040
ttgggaagac aatagcaggc atgctgggga tgcggtgggc tctatggctt ctgaggcgga    2100
aagaaccagc tggggctcta gggggtatcc ccacgcgccc tgtagcggcg cattaagcgc    2160
ggcgggtgtg gtggttacgc gcagcgtgac cgctacactt gccagcgccc tagcgcccgc    2220
tcctttcgct ttcttccctt cctttctcgc cacgttcgcc ggctttcccc gtcaagctct    2280
aaatcggggg ctccctttag ggttccgatt tagtgcttta cggcacctcg accccaaaaa    2340
acttgattag ggtgatggtt cacgtagtgg gccatcgccc tgatagacgg ttttcgccc     2400 tttgacgttg gagtccacgt tctttaatag tggactcttg ttccaaactg gaacaacact    2460
caaccctatc tcggtctatt cttttgattt ataagggatt ttgccgattt cggcctattg    2520
gttaaaaaat gagctgattt aacaaaaatt taacgcgaat taattctgtg gaatgtgtgt    2580
cagttagggt gtggaaagtc cccaggctcc ccagcaggca gaagtatgca aagcatgcat    2640
ctcaattagt cagcaaccag gtgtggaaag tccccaggct ccccagcagg cagaagtatg    2700
caaagcatgc atctcaatta gtcagcaacc atagtcccgc ccctaactcc gcccatcccg    2760
cccctaactc cgcccagttc cgcccattct ccgccccatg ctgactaat ttttttatt      2820 tatgcagagg ccgaggccgc ctctgcctct gagctattcc agaagtagtg aggaggcttt    2880
tttggaggcc taggcttttg caaaaagctc ccgggagctt gtatatccat tttcggatct    2940
gatcaagaga caggatgagg atcgtttcgc atgattgaac aagatggatt gcacgcaggt    3000
tctccggccg cttgggtgga gaggctattc ggctatgact gggcacaaca gacaatcggc    3060
tgctctgatg ccgccgtgtt ccggctgtca gcgcagggg cccggttct ttttgtcaag      3120 accgacctgt ccggtgccct gaatgaactg caggacgagg cagcgcggct atcgtggctg    3180
gccacgacgg gcgttccttg cgcagctgtg ctcgacgttg tcactgaagc gggaagggac    3240
tggctgctat tgggcgaagt gccggggcag gatctcctgt catctcacct tgctcctgcc    3300
gagaaagtat ccatcatggc tgatgcaatg cggcggctgc atacgcttga tccggctacc    3360
tgcccattcg accaccaagc gaaacatcgc atcgagcgag cacgtactcg gatgaagcc    3420 ggtcttgtcg atcaggatga tctggacgaa gagcatcagg gctcgcgcc agccgaactg    3480 ttcgccaggc tcaaggcgcg catgcccgac ggcgaggatc tcgtcgtgac ccatggcgat    3540
gcctgcttgc cgaatatcat ggtggaaaat ggccgctttt ctggattcat cgactgtggc    3600
cggctgggtg tggcggaccg ctatcaggac atagcgttgg ctacccgtga tattgctgaa    3660
gagcttggcg gcgaatgggc tgaccgcttc ctcgtgcttt acggtatcgc cgctcccgat    3720
tcgcagcgca tcgccttcta tcgccttctt gacgagttct tctgagcggg actctgggt     3780 tcgaaatgac cgaccaagcg acgcccaacc tgccatcacg agatttcgat tccaccgccg    3840
ccttctatga aaggttgggc ttcggaatcg ttttccggga cgccggctgg atgatcctcc    3900
agcgcgggga tctcatgctg gagttcttcg cccacccaa cttgtttatt gcagcttata    3960
atggttacaa ataaagcaat agcatcacaa atttcacaaa taaagcattt ttttcactgc    4020
attctagttg tggtttgtcc aaactcatca atgtatctta tcatgtctgt ataccgtcga    4080
cctctagcta gagcttggcg taatcatggt catagctgtt cctgtgtga aattgttatc     4140 cgctcacaat tccacacaac atacgagccg gaagcataaa gtgtaaagcc tggggtgcct    4200
```

```
aatgagtgag ctaactcaca ttaattgcgt tgcgctcact gcccgctttc cagtcgggaa    4260
acctgtcgtg ccagctgcat taatgaatcg gccaacgcgc ggggagaggc ggtttgcgta    4320
ttgggcgctc ttccgcttcc tcgctcactg actcgctgcg ctcggtcgtt cggctgcggc    4380
gagcggtatc agctcactca aaggcggtaa tacggttatc cacagaatca ggggataacg    4440
caggaaagaa catgtgagca aaaggccagc aaaaggccag gaaccgtaaa aaggccgcgt    4500
tgctggcgtt tttccatagg ctccgccccc ctgacgagca tcacaaaaat cgacgctcaa    4560
gtcagaggtg gcgaaacccg acaggactat aaagatacca ggcgtttccc cctggaagct    4620
ccctcgtgcg ctctcctgtt ccgaccctgc cgcttaccgg atacctgtcc gcctttctcc    4680
cttcgggaag cgtggcgctt tctcatagct cacgctgtag gtatctcagt tcggtgtagg    4740
tcgttcgctc caagctgggc tgtgtgcacg aaccccccgt tcagcccgac cgctgcgcct    4800
tatccggtaa ctatcgtctt gagtccaacc cggtaagaca cgacttatcg ccactggcag    4860
cagccactgg taacaggatt agcagagcga ggtatgtagg cggtgctaca gagttcttga    4920
agtggtggcc taactacggc tacactagaa gaacagtatt tggtatctgc gctctgctga    4980
agccagttac cttcggaaaa agagttggta gctcttgatc cggcaaacaa accaccgctg    5040
gtagcggttt ttttgtttgc aagcagcaga ttacgcgcag aaaaaaagga tctcaagaag    5100
atcctttgat cttttctacg gggtctgacg ctcagtggaa cgaaaactca cgttaaggga    5160
ttttggtcat gagattatca aaaaggatct tcacctagat ccttttaaat taaaaatgaa    5220
gttttaaatc aatctaaagt atatatgagt aaacttggtc tgacagttac caatgcttaa    5280
tcagtgaggc acctatctca gcgatctgtc tatttcgttc atccatagtt gcctgactcc    5340
ccgtcgtgta gataactacg atacgggagg gcttaccatc tggccccagt gctgcaatga    5400
taccgcgaga cccacgctca ccggctccag atttatcagc aataaaccag ccagccggaa    5460
gggccgagcg cagaagtggt cctgcaactt tatccgcctc catccagtct attaattgtt    5520
gccgggaagc tagagtaagt agttcgccag ttaatagttt gcgcaacgtt gttgccattg    5580
ctacaggcat cgtggtgtca cgctcgtcgt ttggtatggc ttcattcagc tccggttccc    5640
aacgatcaag gcgagttaca tgatccccca tgttgtgcaa aaaagcggtt agctccttcg    5700
gtcctccgat cgttgtcaga agtaagttgg ccgcagtgtt atcactcatg gttatggcag    5760
cactgcataa ttctcttact gtcatgccat ccgtaagatg cttttctgtg actggtgagt    5820
actcaaccaa gtcattctga gaatagtgta tgcggcgacc gagttgctct tgcccggcgt    5880
caatacggga taataccgcg ccacatagca gaactttaaa agtgctcatc attggaaaac    5940
gttcttcggg gcgaaaactc tcaaggatct taccgctgtt gagatccagt tcgatgtaac    6000
ccactcgtgc acccaactga tcttcagcat cttttacttt caccagcgtt tctgggtgag    6060
caaaaacagg aaggcaaaat gccgcaaaaa agggaataag ggcgacacgg aaatgttgaa    6120
tactcatact cttccttttt caatattatt gaagcattta tcagggttat tgtctcatga    6180
gcggatacat atttgaatgt atttagaaaa ataaacaaat aggggttccg cgcacatttc    6240
cccgaaaagt gccacctgac gtc                                            6263
```

<210> SEQ ID NO 7
<211> LENGTH: 6460
<212> TYPE: DNA
<213> ORGANISM: Artificial sequence
<220> FEATURE:
<223> OTHER INFORMATION: Plasmid

<400> SEQUENCE: 7

```
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccactagt ccagtgtggt ggaattcgtt   960
aacagatctg ctcagctccg tttcggtttc acttccggtg agggccgcc tctgagcggg  1020
cggcgggccg acggcgagcg cgggcggcgg cggtgacgga ggcgccgctg ccaggggcg   1080
tgcggcagcg cggcggcggc ggcggcggcg gaggcggcgg cggcggcggc ggcggcggcg   1140
gcggcggcgg cggcggcggc ggcggcgggg cggcggcggc ggcggcggcg gcggcggcgg   1200
cggcggcggc ggcggcggcg gcggcggcg gcggcggcgg cggggcggcg   1260
gcggcggcgg cggcggcggc ggcggcggcg gcggcggcgg cggcggggcg gcggcggcgg   1320
cggcggcggc ggcggcggcg gcggcggcgg cggcggcggc ggctgggcct cgaggatatc   1380
aagatctggc ctcggcggcc aagcttggca atccggtact gttggtaaag ccaccggggt   1440
cttcacactc gaagatttcg ttggggactg gcgacagaca gccggctaca acctggacca   1500
agtccttgaa cagggaggtg tgtccagttt gtttcagaat ctcggggtgt ccgtaactcc   1560
gatccaaagg attgtcctga gcggtgaaaa tgggctgaag atcgacatcc atgtcatcat   1620
cccgtatgaa ggtctgagcg gcgaccaaat gggccagatc gaaaaaattt ttaaggtggt   1680
gtaccctgtg gatgatcatc actttaaggt gatcctgcac tatggcacac tggtaatcga   1740
cggggttacg ccgaacatga tcgactattt cggacggccg tatgaaggca tcgccgtgtt   1800
cgacggcaaa aagatcactg taacagggac cctgtggaac ggcaacaaaa ttatcgacga   1860
gcgcctgatc aaccccgacg gctccctgct gttccgagta accatcaacg gagtgaccgg   1920
ctggcggctg tgcgaacgca ttctggcgga ctacaaagac catgacggtg attataaaga   1980
tcatgacatc gattacaagg atgacgatga caagcgatcg taatctagag gccgtttaa   2040
acccgctgat cagcctcgac tgtgccttct agttgccagc catctgttgt ttgcccctcc   2100
cccgtgcctt ccttgaccct ggaaggtgcc actcccactg tcctttccta ataaaatgag   2160
gaaattgcat cgcattgtct gagtaggtgt cattctattc tggggggtgg ggtggggcag   2220
gacagcaagg gggaggattg ggaagacaat agcaggcatg ctggggatgc ggtgggctct   2280
atggcttctg aggcggaaag aaccagctgg ggctctaggg ggtatcccca cgcgccctgt   2340
```

```
agcggcgcat taagcgcggc gggtgtggtg gttacgcgca gcgtgaccgc tacacttgcc      2400
agcgccctag cgcccgctcc tttcgctttc ttcccttcct ttctcgccac gttcgccggc      2460
tttccccgtc aagctctaaa tcgggggctc cctttagggt tccgatttag tgctttacgg      2520
cacctcgacc ccaaaaaact tgattagggt gatggttcac gtagtgggcc atcgccctga      2580
tagacggttt ttcgcccttt gacgttggag tccacgttct ttaatagtgg actcttgttc      2640
caaactggaa caacactcaa ccctatctcg gtctattctt ttgatttata agggattttg      2700
ccgatttcgg cctattggtt aaaaaatgag ctgatttaac aaaaatttaa cgcgaattaa      2760
ttctgtggaa tgtgtgtcag ttagggtgtg aaagtccccc aggctcccca gcaggcagaa      2820
gtatgcaaag catgcatctc aattagtcag caaccaggtg tggaaagtcc caggctccc       2880 cagcaggcag aagtatgcaa agcatgcatc tcaattagtc agcaaccata gtcccgcccc      2940
taactccgcc catcccgccc ctaactccgc ccagttccgc ccattctccg ccccatggct      3000
gactaatttt ttttatttat gcagaggccg aggccgcctc tgcctctgag ctattccaga      3060
agtagtgagg aggctttttt ggaggcctag gcttttgcaa aaagctcccg ggagcttgta      3120
tatccatttt cggatctgat caagagacag gatgaggatc gtttcgcatg attgaacaag      3180
atggattgca cgcaggttct ccggccgctt gggtggagag gctattcggc tatgactggg      3240
cacaacagac aatcggctgc tctgatgccg ccgtgttccg gctgtcagcg caggggcgcc      3300
cggttctttt tgtcaagacc gacctgtccg gtgccctgaa tgaactgcag gacgaggcag      3360
cgcggctatc gtggctggcc acgacgggcg ttccttgcgc agctgtgctc gacgttgtca      3420
ctgaagcggg aagggactgg ctgctattgg gcgaagtgcc ggggcaggat ctcctgtcat      3480
ctcaccttgc tcctgccgag aaagtatcca tcatggctga tgcaatgcgg cggctgcata      3540
cgcttgatcc ggctacctgc ccattcgacc accaagcgaa acatcgcatc gagcgagcac      3600
gtactcggat ggaagccggt cttgtcgatc aggatgatct ggacgaagag catcaggggc      3660
tcgcgccagc cgaactgttc gccaggctca aggcgcgcat gcccgacggc gaggatctcg      3720
tcgtgaccca tggcgatgcc tgcttgccga atatcatggt ggaaaatggc cgcttttctg      3780
gattcatcga ctgtggccgg ctgggtgtgg cggaccgcta tcaggacata gcgttggcta      3840
cccgtgatat tgctgaagag cttggcggcg aatgggctga ccgcttcctc gtgctttacg      3900
gtatcgccgc tcccgattcg cagcgcatcg ccttctatcg ccttcttgac gagttcttct      3960
gagcgggact ctggggttcg aaatgaccga ccaagcgacg cccaacctgc catcacgaga      4020
tttcgattcc accgccgcct tctatgaaag gttgggcttc ggaatcgttt tccgggacgc      4080
cggctggatg atcctccagc gcggggatct catgctggag ttcttcgccc accccaactt      4140
gtttattgca gcttataatg gttacaaata aagcaatagc atcacaaatt tcacaaataa      4200
agcatttttt tcactgcatt ctagttgtgg tttgtccaaa ctcatcaatg tatcttatca      4260
tgtctgtata ccgtcgacct ctagctagag cttggcgtaa tcatggtcat agctgtttcc      4320
tgtgtgaaat tgttatccgc tcacaattcc acacaacata cgagccggaa gcataaagtg      4380
taaagcctgg ggtgcctaat gagtgagcta actcacatta attgcgttgc gctcactgcc      4440
cgctttccag tcgggaaacc tgtcgtgcca gctgcattaa tgaatcggcc aacgcgcggg      4500
gagaggcggt ttgcgtattg ggcgctcttc cgcttcctcg ctcactgact cgctgcgctc      4560
ggtcgttcgg ctgcggcgag cggtatcagc tcactcaaag gcggtaatac ggttatccac      4620
agaatcaggg gataacgcag gaaagaacat gtgagcaaaa ggccagcaaa aggccaggaa      4680
```

| | |
|---|---:|
| ccgtaaaaag gccgcgttgc tggcgttttt ccataggctc cgcccccctg acgagcatca | 4740 |
| caaaaatcga cgctcaagtc agaggtggcg aaacccgaca ggactataaa gataccaggc | 4800 |
| gtttccccct ggaagctccc tcgtgcgctc tcctgttccg accctgccgc ttaccggata | 4860 |
| cctgtccgcc tttctccctt cgggaagcgt ggcgctttct catagctcac gctgtaggta | 4920 |
| tctcagttcg gtgtaggtcg ttcgctccaa gctgggctgt gtgcacgaac cccccgttca | 4980 |
| gcccgaccgc tgcgccttat ccggtaacta tcgtcttgag tccaacccgg taagacacga | 5040 |
| cttatcgcca ctggcagcag ccactggtaa caggattagc agagcgaggt atgtaggcgg | 5100 |
| tgctacagag ttcttgaagt ggtggcctaa ctacggctac actagaagaa cagtatttgg | 5160 |
| tatctgcgct ctgctgaagc cagttacctt cggaaaaaga gttggtagct cttgatccgg | 5220 |
| caaacaaacc accgctggta gcggtttttt tgtttgcaag cagcagatta cgcgcagaaa | 5280 |
| aaaaggatct caagaagatc ctttgatctt ttctacgggg tctgacgctc agtggaacga | 5340 |
| aaactcacgt taagggattt tggtcatgag attatcaaaa aggatcttca cctagatcct | 5400 |
| tttaaattaa aaatgaagtt ttaaatcaat ctaaagtata tatgagtaaa cttggtctga | 5460 |
| cagttaccaa tgcttaatca gtgaggcacc tatctcagcg atctgtctat ttcgttcatc | 5520 |
| catagttgcc tgactccccg tcgtgtagat aactacgata cgggagggct taccatctgg | 5580 |
| ccccagtgct gcaatgatac cgcgagaccc acgctcaccg gctccagatt tatcagcaat | 5640 |
| aaaccagcca gccggaaggg ccgagcgcag aagtggtcct gcaactttat ccgcctccat | 5700 |
| ccagtctatt aattgttgcc gggaagctag agtaagtagt tcgccagtta atagtttgcg | 5760 |
| caacgttgtt gccattgcta caggcatcgt ggtgtcacgc tcgtcgtttg gtatggcttc | 5820 |
| attcagctcc ggttcccaac gatcaaggcg agttacatga tcccccatgt tgtgcaaaaa | 5880 |
| agcggttagc tccttcggtc ctccgatcgt tgtcagaagt aagttggccg cagtgttatc | 5940 |
| actcatggtt atggcagcac tgcataattc tcttactgtc atgccatccg taagatgctt | 6000 |
| ttctgtgact ggtgagtact caaccaagtc attctgagaa tagtgtatgc ggcgaccgag | 6060 |
| ttgctcttgc ccggcgtcaa tacgggataa taccgcgcca catagcagaa ctttaaaagt | 6120 |
| gctcatcatt ggaaaacgtt cttcggggcg aaaactctca aggatcttac cgctgttgag | 6180 |
| atccagttcg atgtaaccca ctcgtgcacc caactgatct tcagcatctt ttactttcac | 6240 |
| cagcgtttct gggtgagcaa aaacaggaag gcaaaatgcc gcaaaaaagg gaataagggc | 6300 |
| gacacggaaa tgttgaatac tcatactctt cctttttcaa tattattgaa gcatttatca | 6360 |
| gggttattgt ctcatgagcg gatacatatt tgaatgtatt tagaaaaata aacaaatagg | 6420 |
| ggttccgcgc acatttcccc gaaaagtgcc acctgacgtc | 6460 |

<210> SEQ ID NO 8
<211> LENGTH: 7707
<212> TYPE: DNA
<213> ORGANISM: Artificial sequence
<220> FEATURE:
<223> OTHER INFORMATION: Plasmid

<400> SEQUENCE: 8

| | |
|---|---:|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |

```
tggagttccg cgttacataa cttacggtaa atggcccgcc tggctgaccg cccaacgacc      360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattcgtt    960
aacagatctg ctcagctccg tttcggtttc acttccggtg gagggccgcc tctgagcggg   1020
cggcgggccg acggcgagcg cgggcggcgg cggtgacgga ggcgccgctg ccaggggcg    1080
tgcggcagcg cggcggcggc ggcggcggcg gcggaggcgg cggcggcggc ggcggcggcg   1140
gcggcggcgg cggcggcggc ggcggcggcg gcggcggcgg cggcggcggc ggcggcggcg   1200
gcggcggcgg cggcggcggc ggcggcggcg gcggcggcgg cggcggcggc ggcggcggcg   1260
gcggcggcgg cggcggcggc ggcggcggcg gcggcggcgg cggcggcggc ggcggcggcg   1320
gcggcggcgg cggcggcggc ggcggcggcg gcggcggcg ctgggcctcg aggatatcaa    1380
gatctggcct cggcggccaa gcttggcaat ccggtactgt tggtaaagcc accggggtct   1440
tcacactcga agatttcgtt ggggactggc gacagacagc cggctacaac ctggaccaag   1500
tccttgaaca gggaggtgtg tccagtttgt ttcagaatct cggggtgtcc gtaactccga   1560
tccaaaggat tgtcctgagc ggtgaaaatg ggctgaagat cgacatccat gtcatcatcc   1620
cgtatgaagg tctgagcggc gaccaaatgg gccagatcga aaaaattttt aaggtggtgt   1680
accctgtgga tgatcatcac tttaaggtga tcctgcacta tggcacactg gtaatcgacg   1740
gggttacgcc gaacatgatc gactatttcg gacgccgta tgaaggcatc gccgtgttcg    1800
acggcaaaaa gatcactgta acagggaccc tgtgaacgg caacaaaatt atcgacgagc    1860
gcctgatcaa ccccgacggc tccctgctgt tccgagtaac catcaacgga gtgaccggct   1920
ggcggctgtg cgaacgcatt ctggcggact acaaagacga tgacggtgat tataaagatc   1980
atgacatcga ttacaaggat gacgatgaca gcgatcgaa ttctcacggc tttccgcctg    2040
aggttgaaga gcaagccgcc ggtacattgc ctatgtcctg cgcacaagaa agcggtatgg   2100
accggcaccc agccgcttgt gcttcagctc gcatcaacgt cttaatctag aactgcataa   2160
tctagaactg cataattctg aagttatatt tcctatacca tttccgtaat tcttattcca   2220
tattagaaaa ctttgttagg ccaaagacaa atagtaggca agatggcaca gggcatgaaa   2280
tgaacacaaa ttatgctaag aatttttat tttttggtat tggccataag caacaatttt    2340
cagatttgca caaaaagata ccttaaaatt tgaaacattg cttttaaaac tacttagcac    2400
ttcagggcag attttagttt tatttttctaa agtactgagc agtgatattc tttgttaatt   2460
tggaccattt tcctgcattg ggtgatcatt caccagtaca ttctcagttt ttcttaatat    2520
atagcattta tggtaatcat attagacttc tgttttcaat ctcgtataga agtcttcatg    2580
aaatgctatg tcatttcatg tcctgtgtca gtttatgttt tggtccactt ttccagtatt    2640
```

```
ttagtggacc ctgaaatgtg tgtgatgtga catttgtcat tttcattagc aaaaaaagtt    2700
gtatgatctg tgccttttt  atatcttggc aggtaggaat attatatttg gatgcagagt    2760
tcagggaaga taagttggaa acactaaatg ttaaagatgt agcaaaccct gtcaaacatt    2820
agtactttat agaagaatgc atgctttcca tattttttc  cttacataaa catcaggtta    2880
ggcagtataa agaataggac ttgttttgt  ttttgttttg ttgcactgaa gtttgataaa    2940
tagtgttatt gagagagatg tgtaattttt ctgtatagac aggagaagaa agaactatct    3000
tcatctgaga gaggctaaaa tgttttcagc taggaacaaa tcttcctggt cgaaagttag    3060
taggatatgc ctgctctttg gcctgatgac caatttaac  ttagagcttt tttttttaa     3120
ttttgtctgc cccaagtttt gtgaaatttt tcatatttta atttcaagct tattttggag    3180
agataggaag gtcatttcca tgtatgcata ataatcctgc aaagtacagg actttgtct     3240
aagaaacatt ggaagcaggt taaatgtttt gtaaactttg aaatatatgg tctaatgttt    3300
aagcagaatt ggaaaagact aagatcggtt aacaaataac aacttttttt tcttttttc     3360
ttttgttttt tgaagtgttg gggttggtt  ttgtttttg  agtcttttt  ttttaagtga    3420
aatttattga ggaaaaatat gtgaaggacc ttcactctaa gatgttatat ttttcttaaa    3480
aagtaactcc tagtaggggt accactgaat ctgtacagag ccgtaaaaac tgaagttctg    3540
cctctgatgt attttgtgag tttgtttctt tgaattttca ttttacagtt acttttcctt    3600
gcatacaaac aagcatataa aatggcaaca aactgcacat gatttcacaa atattaaaaa    3660
gtcttttaaa aagtattgcc aaacattaat gttgattct  agttatttat tctgggaatg    3720
tatagtattt gaaaacagaa attggtacct tgcacacatc atctgtaagc tgtttggttt    3780
taaaatactg tagataatta accaaggtag aatgaccttg taatgtaact gctcttgggc    3840
aatattctct gtacatatta gcgacaacag attggatttt atgttgacat ttgtttggtt    3900
atagtgcaat atattttgta tgcaagcagt ttcaataaag tttgatcttc ctctgctaaa    3960
ttgatgttga tgcaatcctt acaaatgatt gcttttaaaa ttttaagcta ggaaaagaaa    4020
tctatagaaa gtgttctgtt acaaaatgta actgttacca ttggaaattt cacgtcatag    4080
gaagttagcc tttatctacc aactttcaag aacttgttta ataaagcgaa aaactcaacc    4140
aaatggtaca aaaccacagt gtaccattaa aatatgcact aagtctcttt tttacaaagg    4200
ctgtattcag caaggcgcta acttgcttaa atgtgaatta ctaacttcta aaactgtact    4260
ttgattcaca tgttttcaaa tggagttgga gttcattcat attacaatat ttgtgtgcta    4320
aacgtgtatg ttttcagtt  caaagtcatg atgcccggga gcttgtatat ccattttcgg    4380
atctgatcaa gagacaggat gaggatcgtt tcgcatgatt gaacaagatg gattgcacgc    4440
aggttctccg gccgcttggg tggagaggct attcggctat gactgggcac aacagacaat    4500
cggctgctct gatgccgccg tgttccggct gtcagcgcag gggcgcccgg ttcttttgt     4560
caagaccgac ctgtccggtg ccctgaatga actgcaggac gaggcagcgc ggctatcgtg    4620
gctggccacg acgggcgttc cttgcgcagc tgtgctcgac gttgtcactg aagcgggaag    4680
ggactggctg ctattgggcg aagtgccggg gcaggatctc ctgtcatctc accttgctcc    4740
tgccgagaaa gtatccatca tggctgatgc aatgcggcgg ctgcatacgc ttgatccggc    4800
tacctgccca ttcgaccacc aagcgaaaca tcgcatcgag cgagcacgta ctcggatgga    4860
agccggtctt gtcgatcagg atgatctgga cgaagagcat caggggctcg cgccagccga    4920
actgttcgcc aggctcaagg cgcgcatgcc cgacggcgag gatctcgtcg tgacccatgg    4980
cgatgcctgc ttgccgaata tcatggtgga aaatggccgc ttttctggat tcatcgactg    5040
```

```
tggccggctg ggtgtggcgg accgctatca ggacatagcg ttggctaccc gtgatattgc    5100
tgaagagctt ggcggcgaat gggctgaccg cttcctcgtg ctttacggta tcgccgctcc    5160
cgattcgcag cgcatcgcct tctatcgcct tcttgacgag ttcttctgag cgggactctg    5220
gggttcgaaa tgaccgacca agcgacgccc aacctgccat cacgagattt cgattccacc    5280
gccgccttct atgaaaggtt gggcttcgga atcgttttcc gggacgccgg ctggatgatc    5340
ctccagcgcg gggatctcat gctggagttc ttcgcccacc ccaacttgtt tattgcagct    5400
tataatggtt acaaataaag caatagcatc acaaatttca caaataaagc attttttca    5460 ctgcattcta gttgtggttt gtccaaactc atcaatgtat cttatcatgt ctgtataccg    5520
tcgacctcta gctagagctt ggcgtaatca tggtcatagc tgtttcctgt gtgaaattgt    5580
tatccgctca caattccaca acatacga gccggaagca taagtgtaa agcctggggt    5640 gcctaatgag tgagctaact cacattaatt gcgttgcgct cactgcccgc tttccagtcg    5700
ggaaacctgt cgtgccagct gcattaatga atcggccaac gcgcggggag aggcggtttg    5760
cgtattgggc gctcttccgc ttcctcgctc actgactcgc tgcgctcggt cgttcggctg    5820
cggcgagcgg tatcagctca ctcaaaggcg gtaatacggt tatccacaga atcaggggat    5880
aacgcaggaa agaacatgtg agcaaaaggc cagcaaaagg ccaggaaccg taaaaaggcc    5940
gcgttgctgg cgtttttcca taggctccgc cccctgacg agcatcacaa aaatcgacgc    6000
tcaagtcaga ggtggcgaaa cccgacagga ctataaagat accaggcgtt ccccctgga    6060 agctccctcg tgcgctctcc tgttccgacc ctgccgctta ccggatacct gtccgccttt    6120
ctcccttcgg gaagcgtggc gctttctcat agctcacgct gtaggtatct cagttcggtg    6180
taggtcgttc gctccaagct gggctgtgtg cacgaacccc ccgttcagcc cgaccgctgc    6240
gccttatccg gtaactatcg tcttgagtcc aacccggtaa gacacgactt atcgccactg    6300
gcagcagcca ctggtaacag gattagcaga gcgaggtatg taggcggtgc tacagagttc    6360
ttgaagtggt ggcctaacta cggctacact agaagaacag tatttggtat ctgcgctctg    6420
ctgaagccag ttaccttcgg aaaaagagtt ggtagctctt gatccggcaa acaaaccacc    6480
gctggtagcg gtttttttgt ttgcaagcag cagattacgc gcagaaaaaa aggatctcaa    6540
gaagatcctt tgatctttc tacggggtct gacgctcagt ggaacgaaaa ctcacgttaa    6600
gggattttgg tcatgagatt atcaaaaagg atcttcacct agatcctttt aaattaaaaa    6660
tgaagtttta aatcaatcta agtatatat gagtaaactt ggtctgacag ttaccaatgc    6720
ttaatcagtg aggcacctat ctcagcgatc tgtctatttc gttcatccat agttgcctga    6780
ctccccgtcg tgtagataac tacgatacgg gagggcttac catctggccc cagtgctgca    6840
atgataccgc gagacccacg ctcaccggct ccagatttat cagcaataaa ccagccagcc    6900
ggaagggccg agcgcagaag tggtcctgca actttatccg cctccatcca gtctattaat    6960
tgttgccggg aagctagagt aagtagttcg ccagttaata gtttgcgcaa cgttgttgcc    7020
attgctacag gcatcgtggt gtcacgctcg tcgtttggta tggcttcatt cagctccggt    7080
tcccaacgat caaggcgagt tacatgatcc cccatgttgt gcaaaaaagc ggttagctcc    7140
ttcggtcctc cgatcgttgt cagaagtaag ttggccgcag tgttatcact catggttatg    7200
gcagcactgc ataattctct tactgtcatg ccatccgtaa gatgcttttc tgtgactggt    7260
gagtactcaa ccaagtcatt ctgagaatag tgtatgcggc gaccgagttg ctcttgcccg    7320
gcgtcaatac gggataatac cgcgccacat agcagaactt taaaagtgct catcattgga    7380
```

```
aaacgttctt cggggcgaaa actctcaagg atcttaccgc tgttgagatc cagttcgatg   7440
taacccactc gtgcacccaa ctgatcttca gcatcttttaa ctttcaccag cgtttctggg   7500
tgagcaaaaa caggaaggca aaatgccgca aaaaagggaa taagggcgac acggaaatgt   7560
tgaatactca tactcttcct tttcaatat tattgaagca tttatcaggg ttattgtctc   7620
atgagcggat acatatttga atgtatttag aaaaataaac aaatagggt tccgcgcaca   7680 tttccccgaa aagtgccacc tgacgtc   7707

<210> SEQ ID NO 9
<211> LENGTH: 5977
<212> TYPE: DNA
<213> ORGANISM: Artificial sequence
<220> FEATURE:
<223> OTHER INFORMATION: Plasmid

<400> SEQUENCE: 9
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccaccccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggca atccggtact gttggtaaat aagccaccat ggtcttcaca   960
ctcgaagatt tcgttgggga ctggcgacag acagccggct acaacctgga ccaagtcctt  1020
gaacagggag gtgtgtccag tttgtttcag aatctcgggg tgtccgtaac tccgatccaa  1080
aggattgtcc tgagcggtga aaatgggctg aagatcgaca tccatgtcat catcccgtat  1140
gaaggtctga gcggcgacca aatgggccag atcgaaaaaa tttttaaggt ggtgtaccct  1200
gtggatgatc atcactttaa ggtgatcctg cactatggca cactggtaat cgacggggtt  1260
acgccgaaca tgatcgacta tttcggacgg ccgtatgaag catcgccgt gttcgacggc  1320 aaaaagatca ctgtaacagg gaccctgtgg aacggcaaca aaattatcga cgagcgcctg  1380
atcaaccccg acggctccct gctgttccga gtaaccatca acggagtgac cggctggcgg  1440
ctgtgcgaac gcattctggc ggactacaaa gaccatgacg gtgattataa agatcatgac  1500
atcgattaca aggatgacga tgacaagtaa ggccgcgact ctagagggcc cgtttaaacc  1560
cgctgatcag cctcgactgt gccttctagt tgccagccat ctgttgtttg cccctcccc  1620 gtgccttcct tgaccctgga aggtgccact cccactgtcc tttcctaata aaatgaggaa  1680
attgcatcgc attgtctgag taggtgtcat tctattctgg ggggtgggt ggggcaggac  1740
```

```
agcaagggggg aggattggga agacaatagc aggcatgctg gggatgcggt gggctctatg    1800
gcttctgagg cggaaagaac cagctgggc tctagggggt atcccacgc gccctgtagc      1860 ggcgcattaa gcgcggcggg tgtggtggtt acgcgcagcg tgaccgctac acttgccagc    1920
gccctagcgc ccgctccttt cgctttcttc ccttcctttc tcgccacgtt cgccggcttt    1980
ccccgtcaag ctctaaatcg ggggctccct ttagggttcc gatttagtgc tttacggcac    2040
ctcgacccca aaaaacttga ttagggtgat ggttcacgta gtgggccatc gccctgatag    2100 acggttttc gcccttgac gttggagtcc acgttcttta atagtggact cttgttccaa       2160 actgaacaa cactcaaccc tatctcggtc tattcttttg atttataagg gattttgccg      2220
atttcggcct attggttaaa aaatgagctg atttaacaaa aatttaacgc gaattaattc    2280
tgtggaatgt gtgtcagtta gggtgtggaa agtccccagg ctccccagca ggcagaagta    2340
tgcaaagcat gcatctcaat tagtcagcaa ccaggtgtgg aaagtcccca ggctccccag    2400
caggcagaag tatgcaaagc atgcatctca attagtcagc aaccatagtc ccgcccctaa    2460
ctccgcccat cccgccccta actccgccca gttccgccca ttctccgccc catggctgac    2520 taatttttt tatttatgca gaggccgagg ccgcctctgc ctctgagcta ttccagaagt     2580
agtgaggagg cttttttgga ggcctaggct tttgcaaaaa gctcccggga gcttgtatat    2640
ccattttcgg atctgatcaa gagacaggat gaggatcgtt tcgcatgatt gaacaagatg    2700
gattgcacgc aggttctccg gccgcttggg tggagaggct attcggctat gactgggcac    2760
aacagacaat cggctgctct gatgccgccg tgttccggct gtcagcgcag gggcgcccgg    2820 ttcttttgt caagaccgac ctgtccggtg ccctgaatga actgcaggac gaggcagcgc     2880
ggctatcgtg gctggccacg acgggcgttc cttgcgcagc tgtgctcgac gttgtcactg    2940
aagcgggaag ggactggctg ctattgggcg aagtgccggg gcaggatctc ctgtcatctc    3000
accttgctcc tgccgagaaa gtatccatca tggctgatgc aatgcggcgg ctgcatacgc    3060
ttgatccggc tacctgccca ttcgaccacc aagcgaaaca tcgcatcgag cgagcacgta    3120
ctcggatgga agccggtctt gtcgatcagg atgatctgga cgaagagcat caggggctcg    3180
cgccagccga actgttcgcc aggctcaagg cgcgcatgcc cgacggcgag gatctcgtcg    3240
tgacccatgg cgatgcctgc ttgccgaata tcatggtgga aaatggccgc ttttctggat    3300
tcatcgactg tggccggctg ggtgtggcgg accgctatca ggacatagcg ttggctaccc    3360
gtgatattgc tgaagagctt ggcggcgaat gggctgaccg cttcctcgtg ctttacggta    3420
tcgccgctcc cgattcgcag cgcatcgcct tctatcgcct tcttgacgag ttcttctgag    3480
cgggactctg gggttcgaaa tgaccgacca agcgacgccc aacctgccat cacgagattt    3540
cgattccacc gccgccttct atgaaaggtt gggcttcgga atcgttttcc gggacgccgg    3600
ctggatgatc ctccagcgcg ggatctcat gctggagttc ttcgcccacc ccaacttgtt     3660
tattgcagct tataatggtt acaaataaag caatagcatc acaaatttca caaataaagc    3720
atttttttca ctgcattcta gttgtggttt gtccaaactc atcaatgtat cttatcatgt    3780
ctgtataccg tcgacctcta gctagagctt ggcgtaatca tggtcatagc tgtttcctgt    3840
gtgaaattgt tatccgctca caattccaca acatacga gccggaagca taaagtgtaa       3900
agcctggggt gcctaatgag tgagctaact cacattaatt gcgttgcgct cactgcccgc    3960
tttccagtcg ggaaacctgt cgtgccagct gcattaatga atcggccaac gcgcggggag    4020
aggcggtttg cgtattgggc gctcttccgc ttcctcgctc actgactcgc tgcgctcggt    4080
```

```
cgttcggctg cggcgagcgg tatcagctca ctcaaaggcg gtaatacggt tatccacaga   4140
atcaggggat aacgcaggaa agaacatgtg agcaaaaggc cagcaaaagg ccaggaaccg   4200
taaaaaggcc gcgttgctgg cgttttttcca taggctccgc cccctgacg agcatcacaa   4260
aaatcgacgc tcaagtcaga ggtggcgaaa cccgacagga ctataaagat accaggcgtt   4320
tccccctgga agctccctcg tgcgctctcc tgttccgacc ctgccgctta ccggatacct   4380
gtccgccttt ctcccttcgg gaagcgtggc gctttctcat agctcacgct gtaggtatct   4440
cagttcggtg taggtcgttc gctccaagct gggctgtgtg cacgaacccc ccgttcagcc   4500
cgaccgctgc gccttatccg gtaactatcg tcttgagtcc aacccggtaa gacacgactt   4560
atcgccactg gcagcagcca ctggtaacag gattagcaga gcgaggtatg taggcggtgc   4620
tacagagttc ttgaagtggt ggcctaacta cggctacact agaagaacag tatttggtat   4680
ctgcgctctg ctgaagccag ttaccttcgg aaaaagagtt ggtagctctt gatccggcaa   4740
acaaaccacc gctggtagcg gtttttttgt ttgcaagcag cagattacgc gcagaaaaaa   4800
aggatctcaa gaagatcctt tgatcttttc tacggggtct gacgctcagt ggaacgaaaa   4860
ctcacgttaa gggattttgg tcatgagatt atcaaaaagg atcttcacct agatcctttt   4920
aaattaaaaa tgaagtttta atcaatcta agtatatat gagtaaactt ggtctgacag   4980
ttaccaatgc ttaatcagtg aggcacctat ctcagcgatc tgtctatttc gttcatccat   5040
agttgcctga ctccccgtcg tgtagataac tacgatacgg gagggcttac catctggccc   5100
cagtgctgca atgataccgc gagacccacg ctcaccggct ccagatttat cagcaataaa   5160
ccagccagcc ggaagggccg agcgcagaag tggtcctgca actttatccg cctccatcca   5220
gtctattaat tgttgccggg aagctagagt aagtagttcg ccagttaata gtttgcgcaa   5280
cgttgttgcc attgctacag gcatcgtggt gtcacgctcg tcgtttggta tggcttcatt   5340
cagctccggt tcccaacgat caaggcgagt tacatgatcc cccatgttgt gcaaaaaagc   5400
ggttagctcc ttcggtcctc cgatcgttgt cagaagtaag ttggccgcag tgttatcact   5460
catggttatg gcagcactgc ataattctct tactgtcatg ccatccgtaa gatgcttttc   5520
tgtgactggt gagtactcaa ccaagtcatt ctgagaatag tgtatgcggc gaccgagttg   5580
ctcttgcccg gcgtcaatac gggataatac cgcgccacat agcagaactt taaaagtgct   5640
catcattgga aaacgttctt cggggcgaaa actctcaagg atcttaccgc tgttgagatc   5700
cagttcgatg taacccactc gtgcacccaa ctgatcttca gcatctttta ctttcaccag   5760
cgtttctggg tgagcaaaaa caggaaggca aaatgccgca aaaaagggaa taagggcgac   5820
acggaaatgt tgaatactca tactcttcct ttttcaatat tattgaagca tttatcaggg   5880
ttattgtctc atgagcggat acatatttga atgtatttag aaaaataaac aaataggggt   5940
tccgcgcaca tttccccgaa aagtgccacc tgacgtc                            5977
```

<210> SEQ ID NO 10
<211> LENGTH: 6487
<212> TYPE: DNA
<213> ORGANISM: Artificial sequence
<220> FEATURE:
<223> OTHER INFORMATION: Plasmid

<400> SEQUENCE: 10

```
atcgcagttt cgatataggt gacagacgat atgaggctat atcgccgata gaggcgacat     60
caagctggca catggccaat gcatatcgat ctatacattg aatcaatatt ggccattagc    120
catattattc attggttata tagcataaat caatattggc tattggccat tgcatacgtt    180
```

```
gtatccatat cataatatgt acatttatat tggctcatgt ccaacattac cgccatgttg    240
acattgatta ttgactagtt attaatagta atcaattacg gggtcattag ttcatagccc    300
atatatggag ttccgcgtta cataacttac ggtaaatggc ccgcctggct gaccgcccaa    360
cgacccccgc ccattgacgt caataatgac gtatgttccc atagtaacgc caatagggac    420
tttccattga cgtcaatggg tggagtattt acggtaaact gcccacttgg cagtacatca    480
agtgtatcat atgccaagta cgccccctat tgacgtcaat gacggtaaat ggcccgcctg    540
gcattatgcc cagtacatga ccttatggga ctttcctact tggcagtaca tctacgtatt    600
agtcatcgct attaccatgg tgatgcggtt ttggcagtac atcaatgggc gtggatagcg    660
gtttgactca cggggatttc caagtctcca ccccattgac gtcaatggga gtttgttttg    720
gcaccaaaat caacgggact ttccaaaatg tcgtaacaac tccgccccat tgacgcaaat    780
gggcggtagg cgtgtacggt gggaggtcta tataagcaga gctcgtttag tgaaccgtca    840
gatcgcctgg agacgccatc cacgctgttt tgacctccat agaagacacc gggaccgatc    900
cagcctccgc ggccgggaac ggtgcattgg aacgcggatt ccccgtgcca agagtgacgt    960
aagtaccgcc tatagagtct ataggcccac cccttggct tcttatgcat gctatactgt    1020
ttttggcttg gggtctatac accccgctt cctcatgtta taggtgatgg tatagcttag    1080
cctataggtg tgggttattg accattattg accactcccc tattggtgac gatactttcc    1140
attactaatc cataacatgg ctctttgcac aactctcttt attggctata tgccaataca    1200
ctgtccttca gagactgaca cggactctgt atttttacag gatggggtct catttattat    1260
ttacaaattc acatatacaa caccaccgtc cccagtgccc gcagttttta ttaaacataa    1320
cgtgggatct ccagcgaatc tcgggtacgt gttccggaca tggggctctt ctccggtagc    1380
ggcggagctt ctacatccag ccctgctccc atcctcccac tcatggtcct cggcagctcc    1440
ttgctcctaa cagtggaggc cagacttagg cacagcacga tgcccaccac caccagtgtg    1500
cccacaaggc cgtggcggta gggtatgtgt ctgaaaatga gctcggggag cgggcttgca    1560
ccgctgacgc atttgaaga cttaaggcag cggcagaaga agatgcaggc agctgagttg    1620
ttgtgttctg ataagagtca gaggtaactc ccgttgcggt gctgttaacg gtggagggca    1680
gtgtagtctg agcagtactc gttgctgccg cgcgcgccac cagacataat agctgacaga    1740
ctaacagact gttcctttcc atgggtcttt tctgcagtca ccgtccttga cacgaagctt    1800
ggtaccgagc tcggatccac tagtccagtg tggtggaatt cgttaacaga tctgctcagc    1860
tccgtttcgg tttcacttcc ggtggagggc gcctctgag cggcggcgg ccgacggcg    1920 agcgcgggcg gcggcggtga cggaggcgcc gctgccaggg ggcgtgcggc agcgcggcgg    1980
cggcggcggc ggcggcggag gcggcggcgg cggcggcggc ggcggcggcg gcggcggcgg    2040
cggcggcggc ggcggcggcg gcggcggcgc ggcggcggcg gcggcggcgg gcggcggcgg    2100
cggcggcggc ggcggcggcg gcggcggcgg cggcggcggc ggcggcggcg gcggcggcgg    2160
cggcggcggc ggcggcggcg gcggcggcgg cggcggcggc ggcggcggcg gcggcggcgg    2220
cggcggcggc ggcggcggcg gcggcggcgg cggcggcggc ggcggcggcg gcggcggcgg    2280
cggcggcggc ggcggcggcg gcggcggcgg cggcggcggc ggcggcggcg gcggcggctg    2280
ggcctcgagc gcccgcagcc cacctctcgg gggcgggctc ccggcgctag cagggctgaa    2340
gagaagatgg aggagctggt ggtggaagtg cggggctcca atggcgcttt ctacaaggca    2400
tttgaaagcg gccgcaccgg tcgccaccat ggtgagcaag ggcgaggagc tgttcaccgg    2460
ggtggtgccc atcctggtcg agctggacgg cgacgtaaac ggccacaagt tcagcgtgtc    2520
```

```
cggcgagggc gagggcgatg ccacctacgg caagctgacc ctgaagttca tctgcaccac    2580
cggcaagctg cccgtgccct ggcccaccct cgtgaccacc ctgacctacg gcgtgcagtg    2640
cttcagccgc taccccgacc acatgaagca gcacgacttc ttcaagtccg ccatgcccga    2700
aggctacgtc caggagcgca ccatcttctt caaggacgac ggcaactaca agacccgcgc    2760
cgaggtgaag ttcgagggcg acaccctggt gaaccgcatc gagctgaagg gcatcgactt    2820
caaggaggac ggcaacatcc tggggcacaa gctggagtac aactacaaca gccacaacgt    2880
ctatatcatg gccgacaagc agaagaacgg catcaaggtg aacttcaaga tccgccacaa    2940
catcgaggac ggcagcgtgc agctcgccga ccactaccag cagaacaccc ccatcggcga    3000
cggccccgtg ctgctgcccg acaaccacta cctgagcacc cagtccgccc tgagcaaaga    3060
ccccaacgag aagcgcgatc acatggtcct gctggagttc gtgaccgccg ccgggatcac    3120
tctcggcatg gacgagctgt acaagtaaag cggccgcgac tctagagggc ccaaccggta    3180
tctagaagat ctagagtcga cctgcaggat atcgaattca ttgatcataa tcagccatac    3240
cacatttgta gaggttttac ttgctttaaa aaacctccca cacctccccc tgaacctgaa    3300
acataaaatg aatgcaattg ttgttgttaa cttgtttatt gcagcttata atggttacaa    3360
ataaagcaat agcatcacaa atttcacaaa taaagcattt ttttcactgc attctagttg    3420
tggtttgtcc aaactcatca atgtatctta tcatgtctgg atccgtaccg agctcgcgta    3480
atcatggtca tagctgtttc ctgtgtgaaa ttgttatccg ctcacaattc cacacaacat    3540
acgagccgga agcataaagt gtaaagcctg gggtgcctaa tgagtgagct aactcacatt    3600
aattgcgttg cgctcactgc ccgctttcca gtcgggaaac ctgtcgtgcc agctgcatta    3660
atgaatcggc caacgcgcgg ggagaggcgg tttgcgtatt gggcgctctt ccgcttcctc    3720
gctcactgac tcgctgcgct cggtcgttcg gctgcggcga gcggtatcag ctcactcaaa    3780
ggcggtaata cggttatcca cagaatcagg ggataacgca ggaaagaaca tgtgagcaaa    3840
aggccagcaa aaggccagga accgtaaaaa ggccgcgttg ctggcgtttt tccataggct    3900
ccgcccccct gacgagcatc acaaaaatcg acgctcaagt cagaggtggc gaaacccgac    3960
aggactataa agataccagg cgtttccccc tggaagctcc ctcgtgcgct ctcctgttcc    4020
gaccctgccg cttaccggat acctgtccgc ctttctccct tcgggaagcg tggcgctttc    4080
tcaatgctca cgctgtaggt atctcagttc ggtgtaggtc gttcgctcca agctgggctg    4140
tgtgcacgaa ccccccgttc agcccgaccg ctgcgcctta tccggtaact atcgtcttga    4200
gtccaacccg gtaagacacg acttatcgcc actggcagca gccactggta acaggattag    4260
cagagcgagg tatgtaggcg gtgctacaga gttcttgaag tggtggccta actacggcta    4320
cactagaagg acagtatttg gtatctgcgc tctgctgaag ccagttacct tcggaaaaag    4380
agttggtagc tcttgatccg gcaaacaaac caccgctggt agcggtggtt ttttgtttg    4440 caagcagcag attacgcgca gaaaaaaagg atctcaagaa gatcctttga tcttttctac    4500
ggggtctgac gctcagtgga acgaaaactc acgttaaggg attttggtca tgagattatc    4560
aaaaaggatc ttcacctaga tccttttaaa ttaaaaatga agttttaaat caatctaaag    4620
tatatatgag taaacttggt ctgacagtta ccaatgctta atcagtgagg cacctatctc    4680
agcgatctgt ctatttcgtt catccatagt tgcctgactc ccgtcgtgt agataactac    4740 gatacgggag ggcttaccat ctggccccag tgctgcaatg ataccgcgag acccacgctc    4800
accggctcca gatttatcag caataaacca gccagccgga agggccgagc gcagaagtgg    4860
tcctgcaact ttatccgcct ccatccagtc tattaattgt tgccgggaag ctagagtaag    4920
```

```
tagttcgcca gttaatagtt tgcgcaacgt tgttgccatt gctacaggca tcgtggtgtc   4980
acgctcgtcg tttggtatgg cttcattcag ctccggttcc caacgatcaa ggcgagttac   5040
atgatccccc atgttgtgca aaaaagcggt tagctccttc ggtcctccga ttgttgtcag   5100
aagtaagttg gccgcagtgt tatcactcat ggttatggca gcactgcata attctcttac   5160
tgtcatgcca tccgtaagat gcttttctgt gactggtgag tactcaacca agtcattctg   5220
agaatagtgt atgcggcgac cgagttgctc ttgcccggcg tcaatacggg ataataccgc   5280
gccacatagc agaactttaa aagtgctcat cattggaaaa cgttcttcgg ggcgaaaact   5340
ctcaaggatc ttaccgctgt tgagatccag ttcgatgtaa cccactcgtg cacccaactg   5400
atcttcagca tcttttactt tcaccagcgt ttctgggtga gcaaaacag gaaggcaaaa    5460 tgccgcaaaa aagggaataa gggcgacacg gaaatgttga atactcatac tcttcctttt   5520
tcaataagcg gccgcggcca tgccggccac tagtctcgag ttattattga agcatttatc   5580
agggttattg tctcatgagc ggatacatat ttgaatgtat ttagaaaaat aaacaaatag   5640
gggttccgcg cacatttccc cgaaaagtgc cacctgacgt ctaagaaacc attattatca   5700
tgacattaac ctataaaaat aggcgtatca cgaggccctt tcgtctcgcg cgtttcggtg   5760
atgacggtga aaacctctga cacatgcagc tcccggagac ggtcacagct tgtctgtaag   5820
cggatgccgg gagcagacaa gcccgtcagg gcgcgtcagc gggtgttggc gggtgtcggg   5880
gctggcttaa ctatgcggca tcagagcaga ttgtactgag agtgcaccat atgaagacgt   5940
cgcctcctca ctacttctgg aatagctcag aggccgaggc ggcctcggcc tctgcataaa   6000
taaaaaaaat tagtcagcgc gccattcgcc attcaggctg cgcaactgtt gggaagggcg   6060
atcggtgcgg gcctcttcgc tattacgcca gctggcgaaa gggggatgtg ctgcaaggcg   6120
attaagttgg gtaacgccag gttttccca gtcacgacgt tgtaaaacga cggccagtgc    6180
catctgcagt gaataataaa atgtgtgttt gtccgaaata cgcgtttgag atttctgtcc   6240
cgactaaatt catgtcgcgc gatagtggtg tttatcgccg atagagatgg cgatattgga   6300
aaaatcgata tttgaaaata tggcatattg aaaatgtcgc cgatgtgagt ttctgtgtaa   6360
ctgatatcgc cattttttcca aaagttgatt tttgggcata cgcgatatct ggcgatacgc   6420
ttatatcgtt tacggggggat ggcgatagac gcctttggtg acttgggcga ttctgtgtgt   6480
cgcaaat                                                             6487

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
cgtcggcccg ccgcccgc                                                   18

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
cgtcggcccg ccgccc                                                     16
```

```
<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
cgtcaccgcc gccgcccg                                                         18

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
cgtcaccgcc gccgcc                                                           16

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15 cacgcccct ggcagcgg                                                          18

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16 cacgcccct ggcagc                                                            16

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
cattgttttt tgtcttcc                                                         18

<210> SEQ ID NO 18
<211> LENGTH: 6678
<212> TYPE: DNA
<213> ORGANISM: Artificial sequence
<220> FEATURE:
<223> OTHER INFORMATION: Synthetic oligonucleotide

<400> SEQUENCE: 18
gacggatcgg gagatctccc gatccctat ggtgcactct cagtacaatc tgctctgatg            60
ccgcatagtt aagccagtat ctgctccctg cttgtgtgtt ggaggtcgct gagtagtgcg          120
cgagcaaaat ttaagctaca acaaggcaag gcttgaccga caattgcatg aagaatctgc          180
ttagggttag gcgttttgcg ctgcttcgcg atgtacgggc cagatatacg cgttgacatt          240
gattattgac tagttattaa tagtaatcaa ttacggggtc attagttcat agcccatata          300
```

-continued

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattcgtt    960
aacagatctg ctcagctccg tttcggtttc acttccggtg gagggccgcc tctgagcggg    1020
cggcgggccg acggcgagcg cgggcggcgg cggtgacgga ggcgccgctg ccaggggggcg   1080
tgcggcagcg cggcggcggc ggcggcggcg cggaggcgg cggcggcggc ggcggcggcg    1140
gcggcggcgg cggcggcggc ggcggcggcg gcggcggcgg cggcggcggc ggcggcggcg    1200
gcggcggcgg cggcggcggc ggcggcggcg gcggcggcgg cggcggcggc ggcggcggcg    1260
gcggcggcgg cggcggcggc ggcggcggcg gcggcggcgg cggcggcggc ggcggcggcg    1320
gcggcggcgg cggcggcggc ggcggcggcg gcggcggcgg cggcggcggc ggcggcggcg    1380
gcggcggcgg cggctgggcc tcgagcgccc gcagcccacc tctcggggc gggctcccgg     1440
cgctagcagg gctgaagaga agatggagga gctggtggtg gaagtgcggg gctccaccgc    1500
ggagcaaggg cgaggagctg ttcaccgggg tggtgcccat cctggtcgag ctggacggcg    1560
acgtaaacgg ccacaagttc agcgtgtccg gcgagggcga gggcgatgcc acctacggca    1620
agctgaccct gaagctgatc tgcaccaccg gcaagctgcc cgtgccctgg cccaccctcg    1680
tgaccaccct gggctacggc ctgcagtgct tcgcccgcta ccccgaccac atgaagcagc    1740
acgacttctt caagtccgcc atgcccgaag gctacgtcca ggagcgcacc atcttcttca    1800
aggacgacgg caactacaag acccgcgccg aggtgaagtt cgagggcgac accctggtga    1860
accgcatcga gctgaagggc atcgacttca aggaggacgg caacatcctg ggcacaagc    1920
tggagtacaa ctacaacagc cacaacgtct atatcaccgc cgacaagcag aagaacggca    1980
tcaaggccaa cttcaagatc cgccacaaca tcgaggacgg cggcgtgcag ctcgccgacc    2040
actaccagca gaacaccccc atcggcgacg gccccgtgct gctgcccgac aaccactacc    2100
tgagctacca gtccgccctg agcaaagacc ccaacgagaa gcgcgatcac atggtcctgc    2160
tggagttcgt gaccgccgcc gggatcactc tcggcatgga cgagctgtac aagccctgca    2220
ggaactgcat aattctgaag tctagagggc cgtttaaac ccgctgatca gcctcgactg    2280
tgccttctag ttgccagcca tctgttgttt gcccctcccc cgtgccttcc ttgaccctgg    2340
aaggtgccac tcccactgtc ctttcctaat aaaatgagga aattgcatcg cattgtctga    2400
gtaggtgtca ttctattctg gggggtgggg tgggcagga cagcaagggg gaggattggg    2460
aagacaatag caggcatgct ggggatgcgg tgggctctat ggcttctgag gcggaaagaa    2520
ccagctgggg ctctagggg tatccccacg cgccctgtag cggcgcatta agcgcggcgg    2580
gtgtggtggt tacgcgcagc gtgaccgcta cacttgccag cgccctagcg cccgctcctt    2640
```

```
tcgctttctt cccttcctttt ctcgccacgt tcgccggctt tccccgtcaa gctctaaatc    2700
gggggctccc tttagggttc cgatttagtg ctttacggca cctcgacccc aaaaaacttg    2760
attagggtga tggttcacgt agtgggccat cgccctgata gacggttttt cgccctttga    2820
cgttggagtc cacgttcttt aatagtggac tcttgttcca aactggaaca acactcaacc    2880
ctatctcggt ctattctttt gattttataag ggattttgcc gatttcggcc tattggttaa    2940
aaaatgagct gatttaacaa aaatttaacg cgaattaatt ctgtggaatg tgtgtcagtt    3000
agggtgtgga aagtccccag gctccccagc aggcagaagt atgcaaagca tgcatctcaa    3060
ttagtcagca accaggtgtg gaaagtcccc aggctcccca gcaggcagaa gtatgcaaag    3120
catgcatctc aattagtcag caaccatagt cccgcccta actccgccca tcccgcccct    3180
aactccgccc agttccgccc attctccgcc ccatggctga ctaatttttt ttatttatgc    3240
agaggccgag gccgcctctg cctctgagct attccagaag tagtgaggag gcttttttgg    3300
aggcctaggc ttttgcaaaa agctcccggg agcttgtata ccatttttcg gatctgatca    3360
agagacagga tgaggatcgt ttcgcatgat tgaacaagat ggattgcacg caggttctcc    3420
ggccgcttgg gtggagaggc tattcggcta tgactgggca caacagacaa tcggctgctc    3480
tgatgccgcc gtgttccggc tgtcagcgca ggggcgcccg gttcttttttg tcaagaccga    3540 cctgtccggt gccctgaatg aactgcagga cgaggcagcg cggctatcgt ggctggccac    3600
gacgggcgtt ccttgcgcag ctgtgctcga cgttgtcact gaagcgggaa gggactggct    3660
gctattgggc gaagtgccgg ggcaggatct cctgtcatct caccttgctc ctgccgagaa    3720
agtatccatc atggctgatg caatgcgcgc gctgcatacg cttgatccgg ctacctgccc    3780
attcgaccac caagcgaaac atcgcatcga gcgagcacgt actcggatgg aagccggtct    3840
tgtcgatcag gatgatctgg acgaagagca tcaggggctc gcgccagccg aactgttcgc    3900
caggctcaag gcgcgcatgc ccgacggcga ggatctcgtc gtgacccatg gcgatgcctg    3960
cttgccgaat atcatggtgg aaaatggccg cttttctgga ttcatcgact gtggccggct    4020
gggtgtggcg gaccgctatc aggacatagc gttggctacc cgtgatattg ctgaagagct    4080
tggcggcgaa tgggctgacc gcttcctcgt gctttacggt atcgccgctc ccgattcgca    4140
gcgcatcgcc ttctatcgcc ttcttgacga gttcttctga gcgggactct ggggttcgaa    4200
atgaccgacc aagcgacgcc caacctgcca tcacgagatt tcgattccac cgccgccttc    4260
tatgaaaggt tgggcttcgg aatcgttttc cgggacgccg gctggatgat cctccagcgc    4320
ggggatctca tgctggagtt cttcgcccac cccaacttgt ttattgcagc ttataatggt    4380
tacaaataaa gcaatagcat cacaaatttc acaaataaag cattttttttc actgcattct    4440 agttgtggtt tgtccaaact catcaatgta tcttatcatg tctgtatacc gtcgacctct    4500
agctagagct tggcgtaatc atggtcatag ctgtttcctg tgtgaaattg ttatccgctc    4560
acaattccac acaacatacg agccggaagc ataaagtgta aagcctgggg tgcctaatga    4620
gtgagctaac tcacattaat tgcgttgcgc tcactgcccg ctttccagtc gggaaacctg    4680
tcgtgccagc tgcattaatg aatcggccaa cgcgcgggga ggcggtttt gcgtattggg    4740 cgctcttccg cttcctcgct cactgactcg ctgcgctcgg tcgttcggct gcggcgagcg    4800
gtatcagctc actcaaaggc ggtaatacgg ttatccacag aatcagggga taacgcagga    4860
aagaacatgt gagcaaaagg ccagcaaaag gccaggaacc gtaaaaaggc cgcgttgctg    4920
gcgtttttcc ataggctccg ccccctgac gagcatcaca aaaatcgacg ctcaagtcag    4980
aggtggcgaa acccgacagg actataaaga taccaggcgt ttccccctgg aagctccctc    5040
```

```
gtgcgctctc ctgttccgac cctgccgctt accggatacc tgtccgcctt tctcccttcg    5100
ggaagcgtgg cgctttctca tagctcacgc tgtaggtatc tcagttcggt gtaggtcgtt    5160
cgctccaagc tgggctgtgt gcacgaaccc cccgttcagc ccgaccgctg cgccttatcc    5220
ggtaactatc gtcttgagtc caacccggta agacacgact tatcgccact ggcagcagcc    5280
actggtaaca ggattagcag agcgaggtat gtaggcggtg ctacagagtt cttgaagtgg    5340
tggcctaact acggctacac tagaagaaca gtatttggta tctgcgctct gctgaagcca    5400
gttaccttcg gaaaaagagt tggtagctct tgatccggca aacaaaccac cgctggtagc    5460
ggtttttttg tttgcaagca gcagattacg cgcagaaaaa aaggatctca agaagatcct    5520
ttgatctttt ctacggggtc tgacgctcag tggaacgaaa actcacgtta agggattttg    5580
gtcatgagat tatcaaaaag gatcttcacc tagatccttt taaattaaaa atgaagtttt    5640
aaatcaatct aaagtatata tgagtaaact tggtctgaca gttaccaatg cttaatcagt    5700
gaggcaccta tctcagcgat ctgtctattt cgttcatcca tagttgcctg actcccgtc    5760 gtgtagataa ctacgatacg ggagggctta ccatctggcc ccagtgctgc aatgataccg    5820
cgagacccac gctcaccggc tccagattta tcagcaataa accagccagc cggaagggcc    5880
gagcgcagaa gtggtcctgc aactttatcc gcctccatcc agtctattaa ttgttgccgg    5940
gaagctagag taagtagttc gccagttaat agtttgcgca acgttgttgc cattgctaca    6000
ggcatcgtgg tgtcacgctc gtcgtttggt atggcttcat tcagctccgg ttcccaacga    6060
tcaaggcgag ttacatgatc ccccatgttg tgcaaaaaag cggttagctc cttcggtcct    6120
ccgatcgttg tcagaagtaa gttggccgca gtgttatcac tcatggttat ggcagcactg    6180
cataattctc ttactgtcat gccatccgta agatgctttt ctgtgactgg tgagtactca    6240
accaagtcat tctgagaata gtgtatgcgg cgaccgagtt gctcttgccc ggcgtcaata    6300
cgggataata ccgcgccaca tagcagaact ttaaaagtgc tcatcattgg aaaacgttct    6360
tcggggcgaa aactctcaag gatcttaccg ctgttgagat ccagttcgat gtaacccact    6420
cgtgcaccca actgatcttc agcatctttt actttcacca gcgtttctgg gtgagcaaaa    6480
acaggaaggc aaaatgccgc aaaaaaggga ataagggcga cacggaaatg ttgaatactc    6540
atactcttcc tttttcaata ttattgaagc atttatcagg gttattgtct catgagcgga    6600
tacatatttg aatgtattta gaaaaataaa caaatagggg ttccgcgcac atttccccga    6660
aaagtgccac ctgacgtc                                                  6678
```